United States Patent
Sayers et al.

(10) Patent No.: US 10,849,912 B2
(45) Date of Patent: Dec. 1, 2020

(54) METHOD OF SENSITIZING CANCER CELLS TO THE CYTOTOXIC EFFECTS OF APOPTOSIS INDUCING LIGANDS IN CANCER TREATMENT

(71) Applicants: The United States of America, as represented by the Secretary, Department of Health and Human Services, Bethesda, MD (US); Arizona Board of Regents on Behalf of the University of Arizona, Tucson, AZ (US)

(72) Inventors: Thomas Joseph Sayers, Boonsboro, MD (US); Alan David Brooks, Frederick, MD (US); Curtis J. Henrich, Rockville, MD (US); Poonam Tewary, Frederick, MD (US); James Brislin McMahon, Frederick, MD (US); Leslie Gunatilaka, Tucson, AZ (US); Ya-Ming Xu, Tucson, AZ (US); Kithsiri Wijeratne, Tucson, AZ (US)

(73) Assignees: The United States of America, as represented by the Secretary, Department of Health and Human Services, Bethesda, MD (US); Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 16/076,954

(22) PCT Filed: Feb. 9, 2017

(86) PCT No.: PCT/US2017/017220
§ 371 (c)(1),
(2) Date: Aug. 9, 2018

(87) PCT Pub. No.: WO2017/139485
PCT Pub. Date: Aug. 17, 2017

(65) Prior Publication Data
US 2019/0046543 A1 Feb. 14, 2019

Related U.S. Application Data

(60) Provisional application No. 62/292,974, filed on Feb. 9, 2016.

(51) Int. Cl.
*C07D 405/14* (2006.01)
*A61K 31/4178* (2006.01)
(Continued)

(52) U.S. Cl.
CPC .......... *A61K 31/585* (2013.01); *A61K 31/351* (2013.01); *A61K 31/366* (2013.01);
(Continued)

(58) Field of Classification Search
CPC .. C07D 405/14; C07D 407/08; C07D 309/32; A61K 31/4178; A61K 31/365
(Continued)

(56) References Cited

U.S. PATENT DOCUMENTS

| 4,235,871 A | 11/1980 | Papahadjopoulos et al. |
| 4,501,728 A | 2/1985 | Geho et al. |

(Continued)

FOREIGN PATENT DOCUMENTS

| WO | WO 98/51793 A1 | 11/1998 |
| WO | WO 2006/017961 A1 | 2/2006 |

(Continued)

OTHER PUBLICATIONS

Xu, Ya-Ming et al.: Discovery of potent 17 beta-hydroxywithanolides for castration-resistant prostate cancer by6 high-throughput screening of a natural products library for androgen-induced gene expression inhibitors. J. Med. Chem., vol. 58, pp. 6984-6993, 2015.*

(Continued)

*Primary Examiner* — Charanjit Aulakh
(74) *Attorney, Agent, or Firm* — Leydig, Voit & Mayer, Ltd.

(57) ABSTRACT

Disclosed is a method of enhancing the response of cancer cells in a mammal to treatment with an apoptosis inducing ligand, which method comprises contacting the cancer cells with an apoptosis inducing ligand in conjunction with an effective amount of a compound of the formula: (I), wherein $R^1$-$R^{14}$ are as described herein. Also disclosed is a method of inducing apoptosis in cancer cells in a mammal, comprising contacting the cancer cells with the compound described herein and also contacting the cancer cells with an apoptosis inducing ligand, whereby apoptosis is induced in the cancer cells.

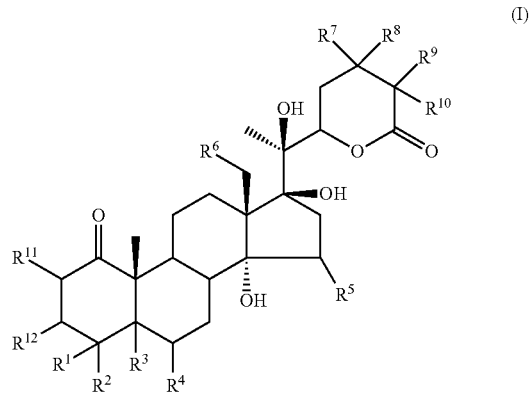

18 Claims, 28 Drawing Sheets

(51) Int. Cl.
| | |
|---|---|
| A61K 31/585 | (2006.01) |
| A61K 31/351 | (2006.01) |
| A61K 31/366 | (2006.01) |
| C07J 71/00 | (2006.01) |
| C07J 17/00 | (2006.01) |
| A61P 35/00 | (2006.01) |
| A61K 45/06 | (2006.01) |

(52) U.S. Cl.
CPC .............. *A61K 45/06* (2013.01); *A61P 35/00* (2018.01); *C07J 17/00* (2013.01); *C07J 71/001* (2013.01)

(58) Field of Classification Search
USPC ............ 548/303.7, 311.1; 549/294; 514/393, 514/397, 460
See application file for complete search history.

(56) References Cited

U.S. PATENT DOCUMENTS

| | | | |
|---|---|---|---|
| 4,837,028 | A | 6/1989 | Allen |
| 5,019,369 | A | 5/1991 | Presant et al. |
| 7,244,429 | B2 | 7/2007 | Zhou et al. |
| 7,893,216 | B2 | 2/2011 | Liu et al. |
| 9,238,069 | B2 | 1/2016 | Sayers et al. |
| 2002/0004227 | A1 | 1/2002 | Ashkenazi et al. |
| 2004/0214235 | A1 | 10/2004 | Mori et al. |
| 2005/0079172 | A1 | 4/2005 | Nasoff et al. |
| 2006/0269554 | A1 | 11/2006 | Adams |
| 2006/0269555 | A1 | 11/2006 | Salcedo et al. |
| 2006/0270837 | A1 | 11/2006 | Salcedo et al. |
| 2007/0179086 | A1 | 8/2007 | Gliniak et al. |
| 2007/0292411 | A1 | 12/2007 | Salcedo et al. |
| 2007/0298039 | A1 | 12/2007 | Zhou et al. |

FOREIGN PATENT DOCUMENTS

| | | |
|---|---|---|
| WO | WO 2010/030395 A2 | 3/2010 |
| WO | WO 2011/084623 A1 | 7/2011 |

OTHER PUBLICATIONS

Bagchi et al., "Withaperuvin E and nicandrin B, withanolides from physalis peruviana and nicandra physaloides," *Phytochemistry*, 23(4):853-855 (1984).

Couzin-Frankel et al., "Breakthrough of the Year 2013 Cancer Immunotherapy," *Science*, 342:1432-1433 (2013).

Estornes et al., "dsRNA Induces Apoptosis Through an Atypical Death Complex Associating TLR3 to caspase-8," *Cell Death Differ.*, 19:1482-1494 (2012).

Fang et al., "Ten new withanolides from Physalis peruviana," *Steroids*, 77:36-44 (2012).

Galluzzi et al., "Classification of Current Anticancer Immunotherapies," *Oncotarget.*, 5(24):12472-12508 (2014).

Gay et al., "Toll-like Receptors as Molecular Switches," *Nat. Rev. Immunol.*, 6:693-698 (2006).

Henrich et al., "Withanolide E Sensitizes Renal Carcinoma Cells to TRAIL-induced Apoptosis by Increasing Cflip Degradation," *Cell Death and Disease*, 1-10 (2015).

Ichikawa et al., "Withanolides Potentiate Apoptosis, Inhibi Invasion, and Abolish Osteoclastogenesis Through Suppression of Nuclear Factor-$_{K}$B (NF-$_{K}$B) Activation and NF-$_{K}$B-regulated Gene Expression," *Mol Cancer Ther*, 5(6): 1434-1445 (2006).

International Preliminary Report on Patentability, The International Bureau of WIPO, dated Aug. 23, 2018, 7 pages.

International Search Report, European Patent Office, PCT/US2017/017220, dated Apr. 24, 2017, 6 pages.

Lee et al., "Withaferin A Sensitizes Trail-induced Apoptosis Through Reactive Oxygen Species-mediated Up-regulation of Death Receptor 5 and Down-regulation of c-FLIP," *Free Radical Biology & Medicine*, 46:1639-1649 (2009).

Salaun et al., "Toll-like Receptor 3 Expressed by Melanoma Cells as a Target for Therapy?," *Clin Cancer Res.*, 13(15):4565-4574 (2007).

Salaun et al., "TLR3 as a Biomarker for the Therapeutic Efficacy of Double-Stranded RNA in Breast Cancer," *Cancer Res.* 71:1607-1614 (2011).

Salaun et al., "TLR3 Can Directly Trigger Apoptosis in Human Cancer Cells," *J Immunol.*, 176:4894-4901 (2006).

Sayers et al., "Targeting the Extrinsic Apoptosis Signaling Pathway for Cancer Therapy," *Cancer Immunol Immunother*, 60:1173-1180 (2011).

Scudiero et al., "Evaluation of a Soluble Tetrazolium/Formazan Assay for Cell Growth and Drug Sensitivity in Culture Using Human and Other Tumor Cell Lines," *Cancer Res.*, 48(17): 4827-4833 (1988).

Skehan et al., "New Colorimetric Cytotoxicity Assay for Anticancer-drug Screening," *J. National Cancer Inst.* 82(13): 1107-1112 (1990).

Szoka et al., "Comparative Properties and Methods of Preparation of Lipid Vesicles (Liposomes)", Ann Rev. Biophys. Bioeng., 9:467-508 (1980).

Takeda et al., "Combination Antibody-based Cancer Immunotherapy," *Cancer Sci*, 98(9)1297-1302 (Sep. 2007).

Wang et al., "Withanolides-Induced Breast Cancer Cell Death is Correlated with Their Ability to Inhibit Heat Protein 90," *PLoSOne*, 7(5):1-10 (May 2012).

Weber et al., "Proapoptotic Signalling Through Toll-like Receptor-3 Involves TRIF-dependent Activation of Caspase-8 and is Under the Control of Inhibitor of Apoptosis Proteins in Melanoma Cells," *Cell Death Differ.*, 17:942-951 (2010).

Written Opinion of the International Searching Authority, European Patent Office, PCT/US2017/017220, dated Apr. 24, 2017, 8 pages.

Yen et al., "413-Hydroxywithanolide E from *Physalis peruviana* (golden berry) Inhibits Growth of Human Lung Cancer Cells through DNA Damage, Apoptosis and G$_2$/M Arrest," *BMC Cancer*, 10:45 (2010).

Yoshida et al., "Relationship Between Chemical Structure and Antitumor Activity of Withaferin A Analogues," *J. Pharm. Dyn.* 2:92-97 (1979).

\* cited by examiner

METHOD OF SENSITIZING CANCER CELLS TO THE CYTOTOXIC EFFECTS OF APOPTOSIS INDUCING LIGANDS IN CANCER TREATMENT

CROSS-REFERENCE TO RELATED APPLICATIONS

This patent application is the national stage of International Patent Application No. PCT/US2017/017220, filed Feb. 9, 2017, which claims the benefit of U.S. Provisional Patent Application No. 62/292,974, filed Feb. 9, 2016, the disclosures of which are incorporated by reference for all purposes.

This invention was made with Government support under Grant Nos. BC 011056 and HHSN261200800001E, awarded by the National Institutes of Health. The Government has certain rights in this invention.

BACKGROUND OF THE INVENTION

One strategy in developing new cancer therapeutics having better toxicity profiles compared with current cytotoxic drugs is to utilize molecularly-targeted therapeutics that selectively target cancer cells versus normal cells. Such molecularly-targeted therapeutics can be used in minimal doses to reduce side effects. Death receptor ligands held initial promise in answering this need because they trigger programmed cell death in their target cancer cells. Two of the best-studied death receptor ligands, Fas ligand and tumor necrosis factor-alpha (TNF-α), have proven to be too toxic for systemic use as anticancer agents in their native forms. However, another death receptor ligand, tumor necrosis factor-α-related apoptosis-inducing ligand, known as TRAIL, and its receptors, has renewed interest in this area of cancer research. Active TRAIL receptors, TR1 (DR4) and TR2 (DR5) are often more highly expressed on cancer cells versus normal cells. Inactive TRAIL "decoy" receptors TR3 (DcR1) and TR4 (DcR2) are sometimes more prevalent on the surface of normal cells. Both DR4 and DR5 transduce death signaling, leading to apoptosis upon binding to TRAIL. Instead, DcR1 and DcR2 lack intact intracellular death domain and therefore cannot signal apoptosis despite binding to TRAIL. Instead, DcR1 or DcR2 protects cells from TRAIL-induced apoptosis by competing with DR4 and DR5 for binding to TRAIL. Interestingly, the expression of DcR1 and DcR2 is either downregulated or lost in many types of cancer cells or tissues while DR4 and DR5 expression are maintained in cancer cells or tissues. This inversely related expression pattern for TRAIL receptors may be partly responsible for the selectivity of TRAIL ligand for tumor cells over normal cells, and its ability to preferentially cause apoptotic cell death in cancer cells, which may also contribute to a more favorable safety profile.

While TRAIL has been reported to successfully target certain tumor cells which are resistant to traditional chemotherapies or radiation, TRAIL resistance has also been widely documented, indeed, many cancer cells are quite resistant to TRAIL as a single agent. Recently it was reported that signaling via Toll-like Receptor (TLR) ligands, particularly TLR3, could also promote apoptosis in certain cancer cells. However, this apoptosis signaling in most cancer cells was relatively weak, and was only significant following longer term incubations of 48-72 h with the RNA double-stranded TLR-3 ligand poly IC (Salaun et al, *J. Immunol.*, 2006, 176: 4894-4901; Salaun et al., *Clin. Cancer Res.*, 2007, 13: 4565-4574)). Nonetheless, some of the same molecular components of the apoptosis signaling pathway are thought to be engaged downstream of both death receptor and TLR ligand signaling (Estornes et al., *Cell Death. Differ.*, 2012, 19: 1482-1494; Weber et al., *Cell Death. Differ.*, 2010, 17: 942-951). However, TLR ligands such as poly IC are also potent adjuvants for enhancing anti-cancer immune responses (Gay et al., *Nat. Rev. Immunol.*, 2006, 6: 693-698).

Thus, there is an unmet need for the development of sensitizers of the cancer cells to apoptosis inducing ligands such as poly IC and TRAIL, especially those that act in a synergistic manner.

BRIEF SUMMARY OF THE INVENTION

The invention provides a method of synergistically enhancing the response of cancer cells in a mammal to treatment with an apoptosis-inducing ligand, which method comprises administering to the mammal an effective amount of a compound of the formula:

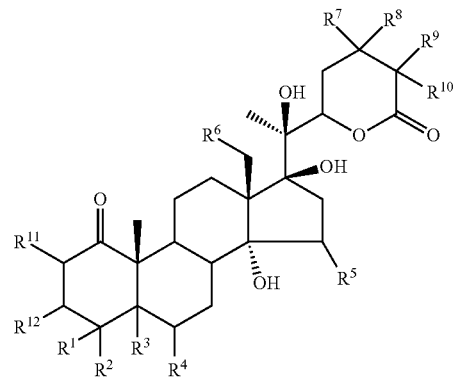

wherein $R^1$ and $R^2$ are independently selected from H, OH, $C_1$-$C_6$ acyloxy, $C_1$-$C_6$ alkylcarbonate, heteroarylcarbonyloxy, a group of the formula:

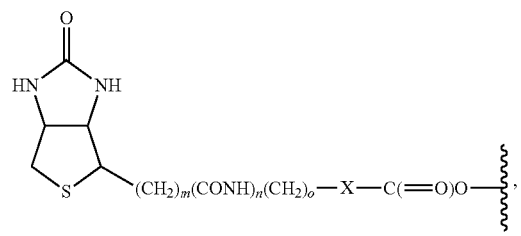

or, $R^1$ and $R^2$ taken together, form =O,

X is NH or is absent, m and o are integers of from 1 to about 10, n is 0 or 1.

$R^3$ and $R^4$ are independently OH or $C_1$-$C_6$ alkoxy or, taken together, form a double bond or an epoxy ring, $R^5$ is H or $C_1$-$C_6$ acyloxy,
$R^6$ is H, OH, or $C_1$-$C_6$ acyloxy,
$R^7$ and $R^9$ are independently $CH_2OH$ or

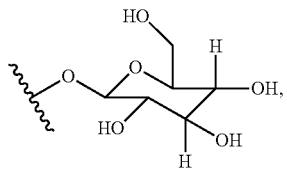

$R^8$ and $R^{10}$, taken together with the carbon atoms to which they are attached, form a double bond or an epoxy ring, and
$R^{11}$ and $R^{12}$ are both H, $R^{11}$ is H and $R^{12}$ is —$OSO_3H$, $R^{11}$ is H and $R^{12}$ is imidazolyl, or $R^{11}$ and $R^{12}$, taken together with the carbon atoms to which they are attached, form a double bond, and administering an effective amount of an apoptosis-inducing ligand, whereby a synergistic enhancement of the response is obtained.

The invention also provides a method of inducing apoptosis in cancer cells in a mammal that are resistant to treatment with an apoptosis-inducing ligand, which method comprises administering to the mammal an effective amount of a compound of the formula:

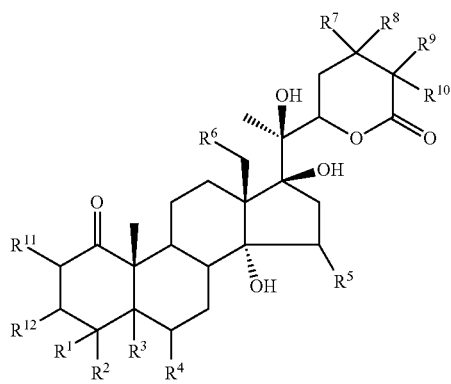

wherein $R^1$ and $R^2$ are independently selected from H, OH, $C_1$-$C_6$ acyloxy, $C_1$-$C_6$ alkylcarbonate, heteroarylcarbonyloxy, a group of the formula:

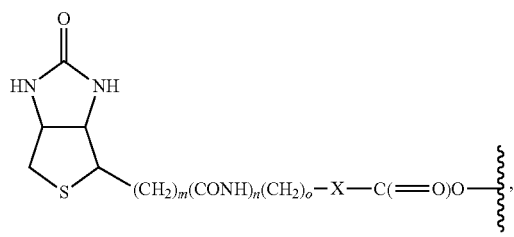

or, $R^1$ and $R^2$ taken together, form =O,
X is NH or is absent,
m and o are integers of from 1 to about 10,
n is 0 or 1,
$R^3$ and $R^4$ are independently OH or $C_1$-$C_6$ alkoxy or, taken together, form a double bond or an epoxy ring, $R^5$ is H or $C_1$-$C_6$ acyloxy,
$R^6$ is H, OH, or $C_1$-$C_6$ acyloxy,
$R^7$ and $R^9$ are independently $CH_2OH$ or

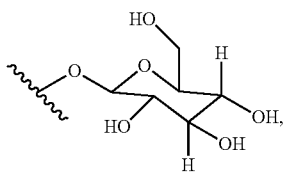

$R^8$ and $R^{10}$, taken together with the carbon atoms to which they are attached, form a double bond or an epoxy ring, and
$R^{11}$ and $R^{12}$ are both H, $R^{11}$ is H and $R^{12}$ is —$OSO_3H$, $R^{11}$ is H and $R^{12}$ is imidazolyl, or $R^{11}$ and $R^{12}$, taken together with the carbon atoms to which they are attached, form a double bond, and administering an effective amount of an apoptosis-inducing ligand, whereby a synergistic enhancement of the response is obtained.

The invention further provides a compound of the formula:

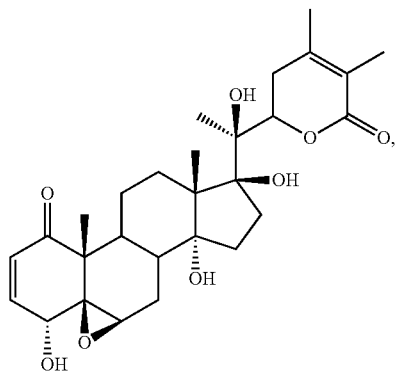

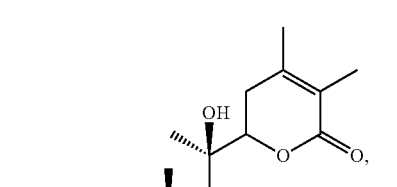

or

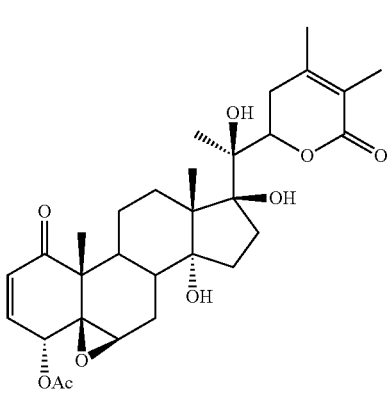

-continued

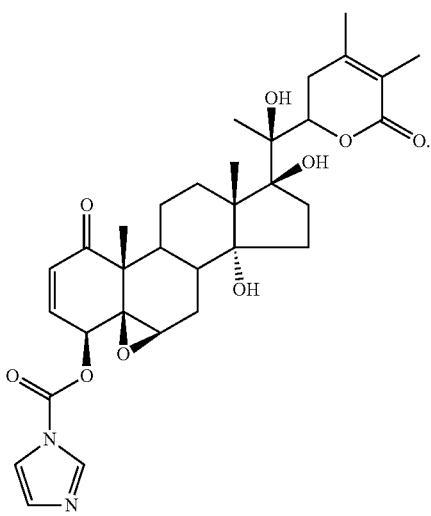

The invention additionally provides a compound of the formula:

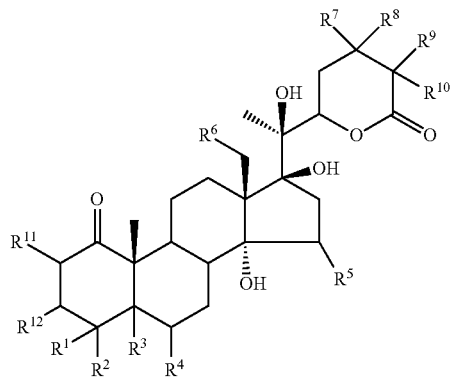

wherein $R^1$ and $R^2$ are independently selected from H and a group of the formula:

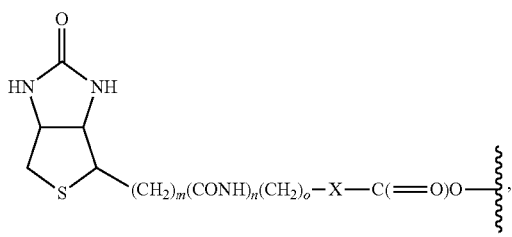

X is NH or is absent, m and o are integers of from 1 to about 10, n is 0 or 1, $R^3$ and $R^4$ are independently OH or $C_1$-$C_6$ alkoxy or, taken together, form a double bond or an epoxy ring, $R^5$ is H or $C_1$-$C_6$ acyloxy, $R^6$ is H, OH, or $C_1$-$C_6$ acyloxy, or $R^7$ and $R^9$ are independently $CH_2OH$ or

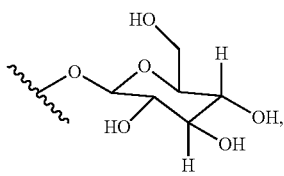

$R^8$ and $R^{10}$, taken together with the carbon atoms to which they are attached, form a double bond or an epoxy ring, and $R^{11}$ and $R^{12}$ are both H, $R^{11}$ is H and $R^{12}$ is —$OSO_3H$, $R^{11}$ is H and $R^{12}$ is imidazolyl, car $R^{11}$ and $R^{12}$, taken together with the carbon atoms to which they are attached, form a double bond.

BRIEF DESCRIPTION OF THE SEVERAL VIEWS OF THE DRAWING(S)

FIGS. 3A-3I depict the percent growth inhibition of ACHN renal cancer cells in the presence of compounds 1, 2, 3, 4, 5, 6, 7, 9, and 10, respectively, at concentrations of 63 nM, 125 nM, 250 nM, and 500 nM, in the presence or absence of 10 μM poly IC.

FIGS. 4A-4I depict the percent growth inhibition of SK MEL28 melanoma cells in the presence of compounds 1, 2, 3, 4, 5, 6, 7, 9, and 10, respectively, at concentrations of 63 nM, 125 nM, 250 nM, and 500 nM, in the presence of absence of 10 μM poly IC.

Figure 1:
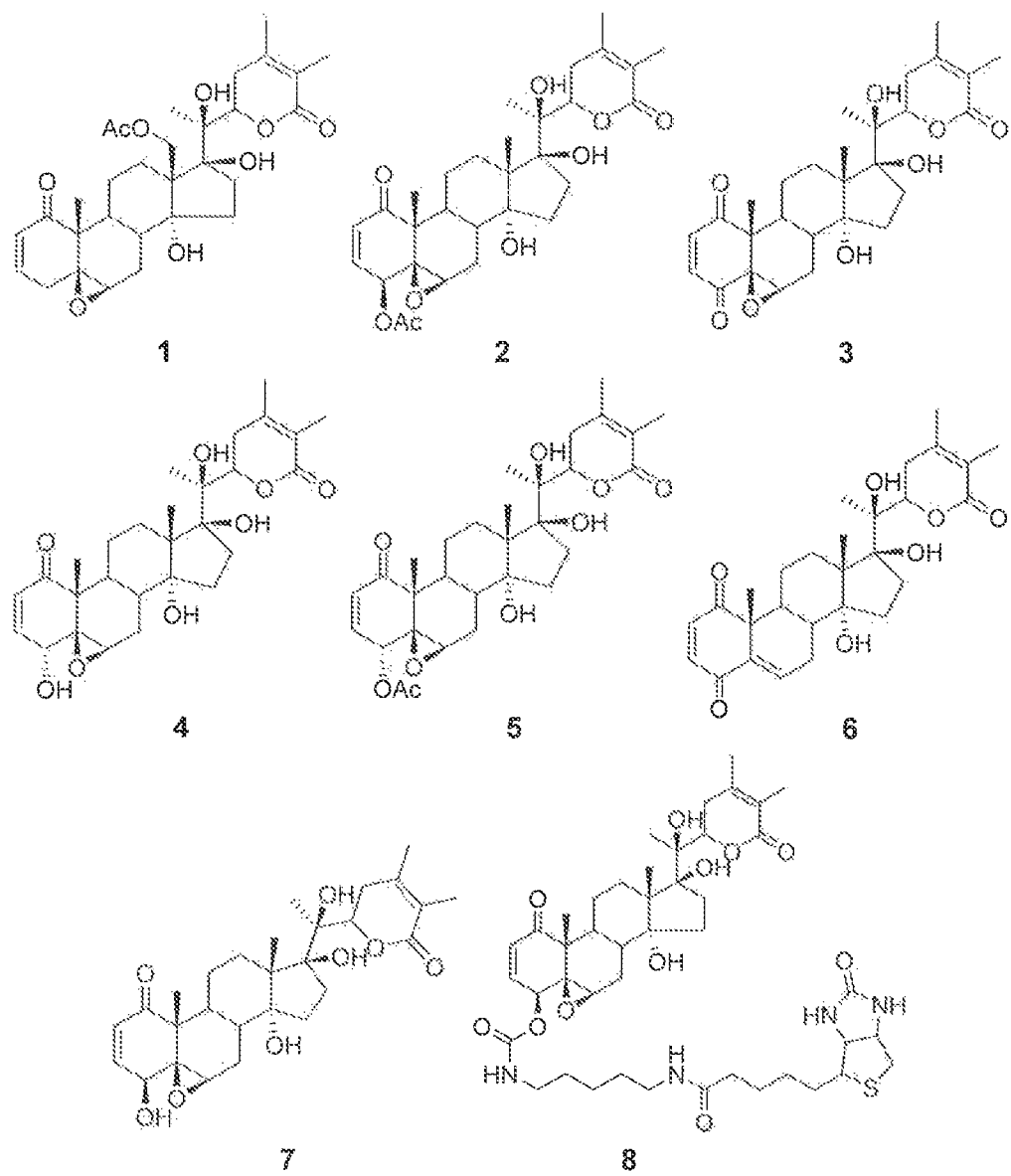
FIG. 1 depicts the structures of compounds 1-8, in accordance with embodiments of the invention.
Figure 2:
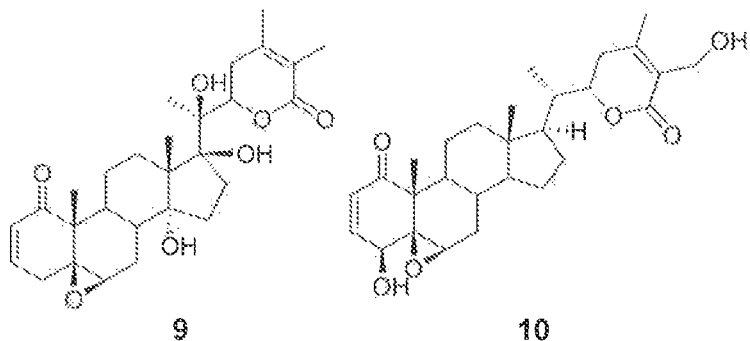
FIG. 2 depicts the structures of withanolide E (9) and withaferin A (10).
Figure 3A:
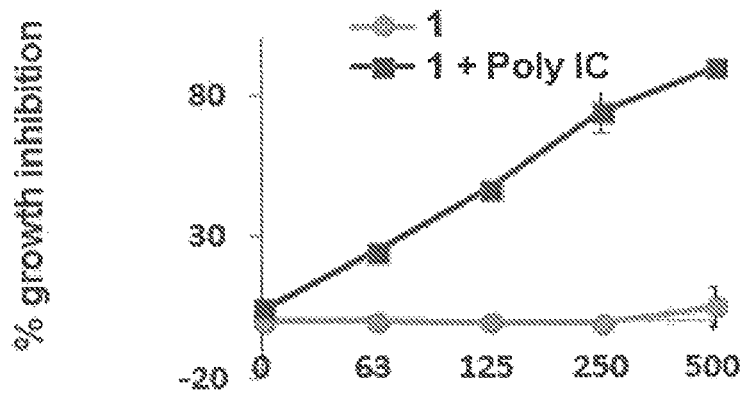
Figure 3B:
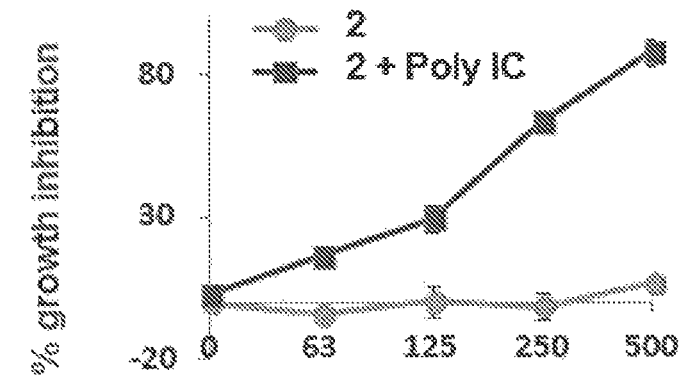
Figure 3C:
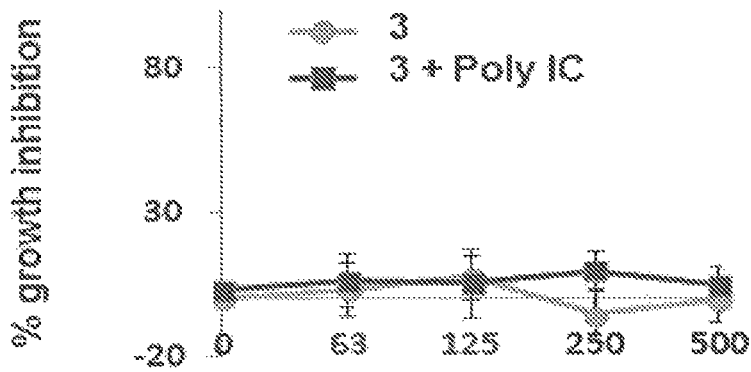
Figure 3D:
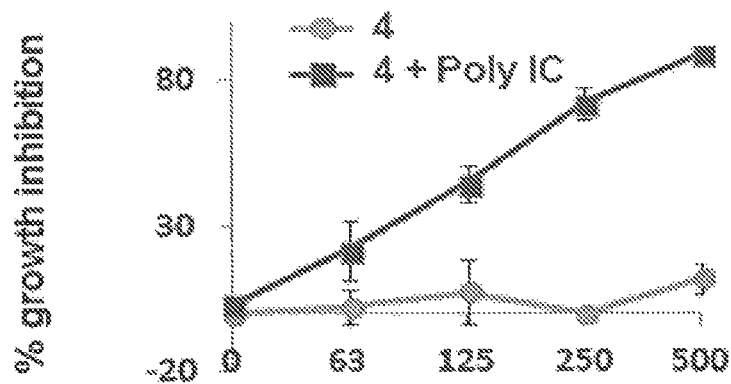
Figure 3E:
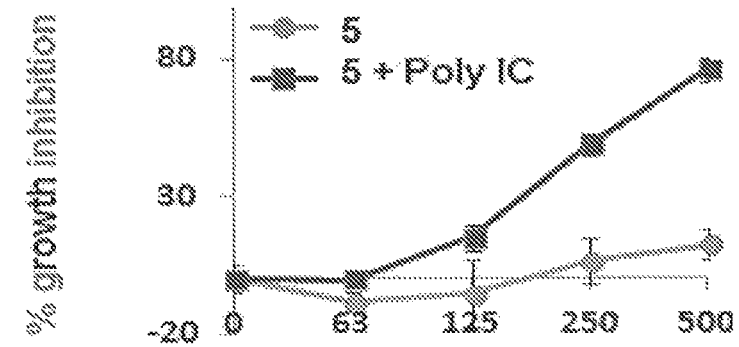
Figure 3F:
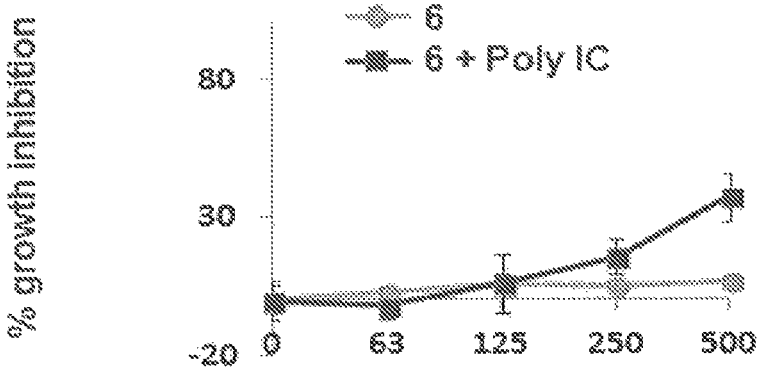
Figure 3G:
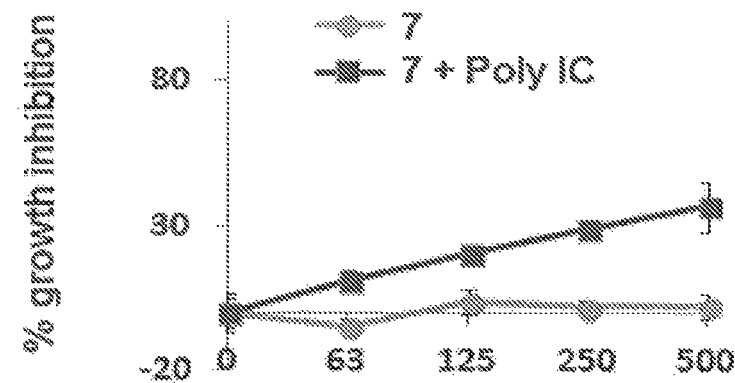
Figure 3H:
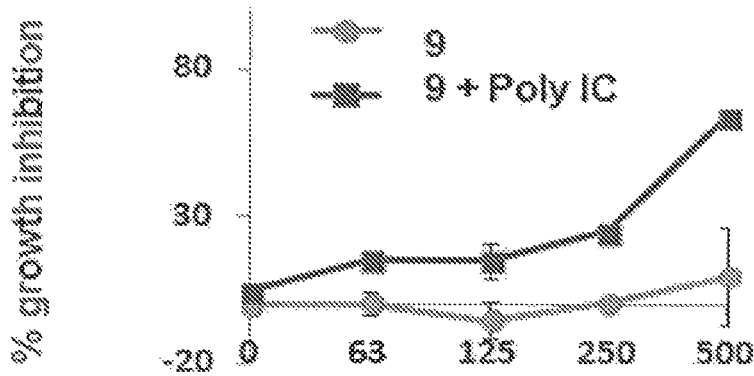
Figure 3I:
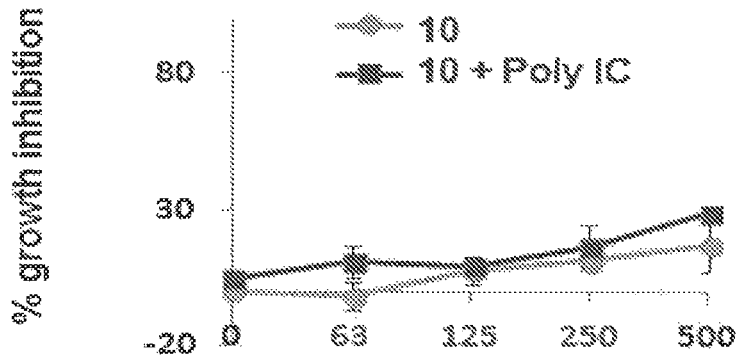
Figure 4A:
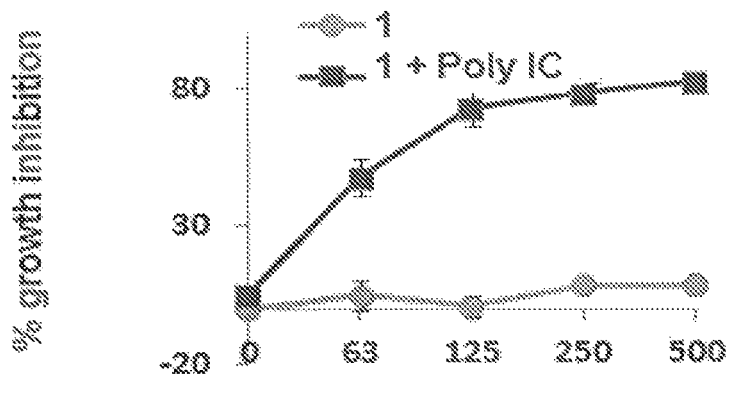
Figure 4B:
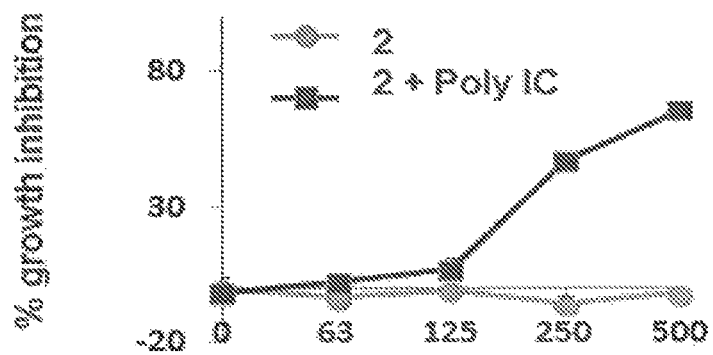
Figure 4C:
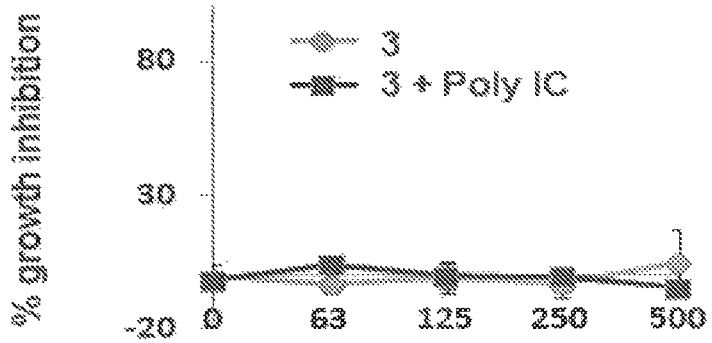
Figure 4D:
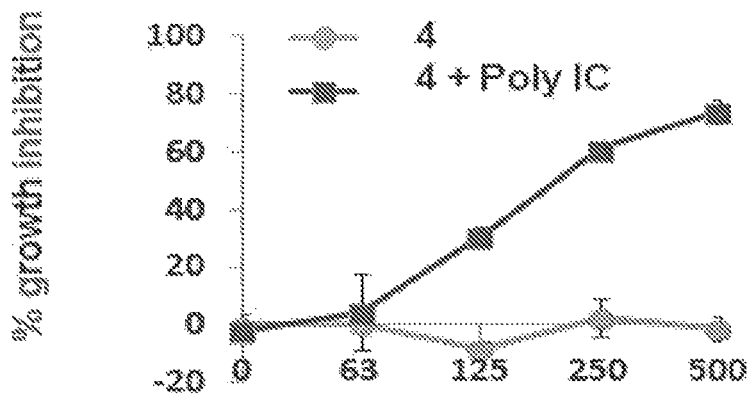
Figure 4E:
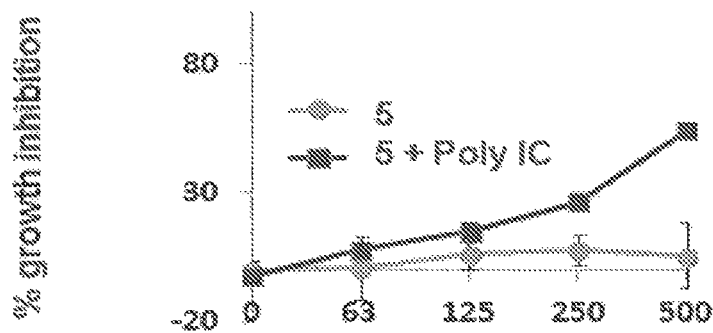
Figure 4F:
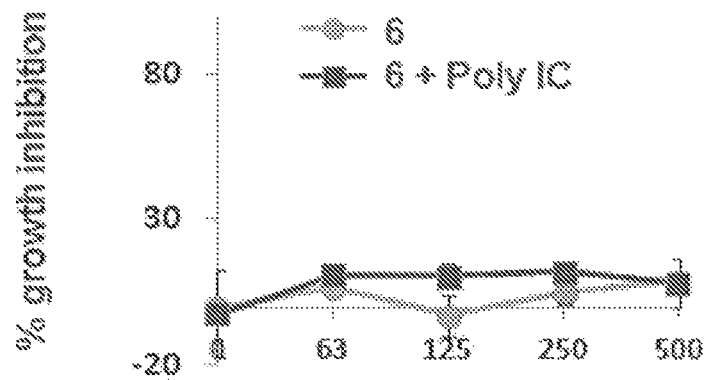
Figure 4G:
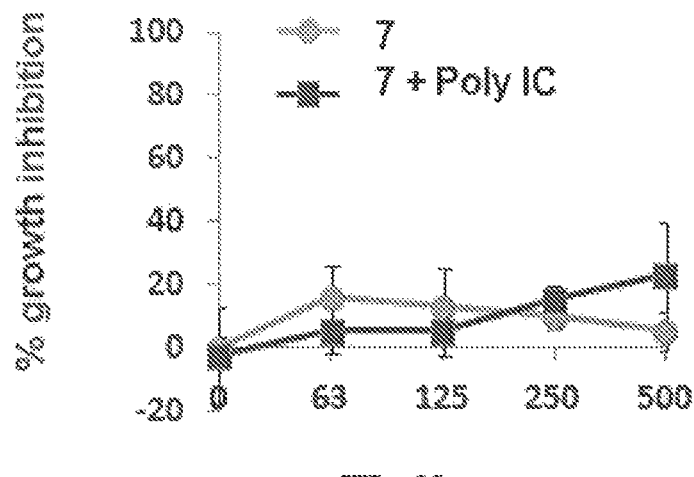
Figure 4H:
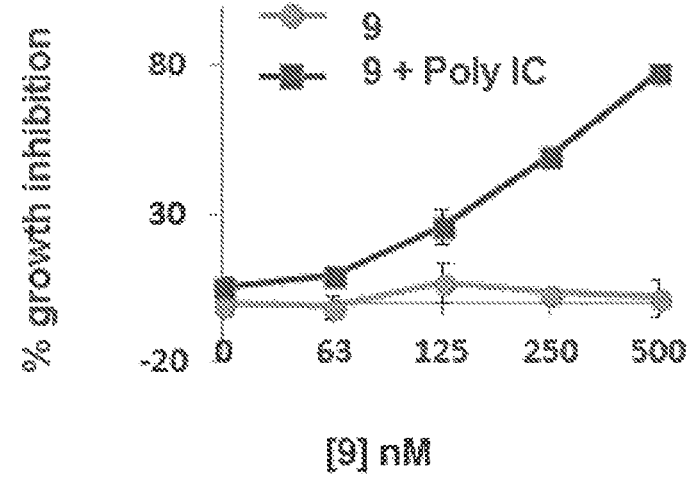
Figure 4I:
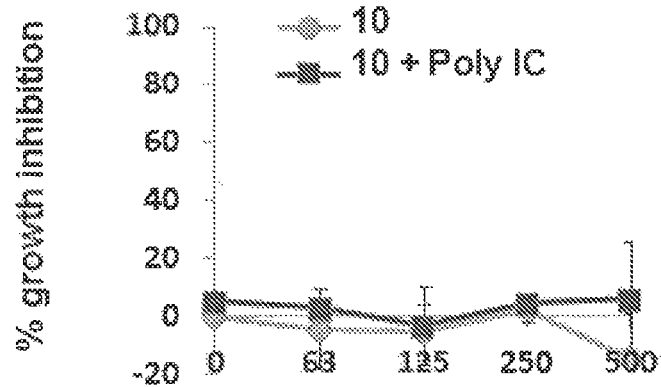
Figure 5A:
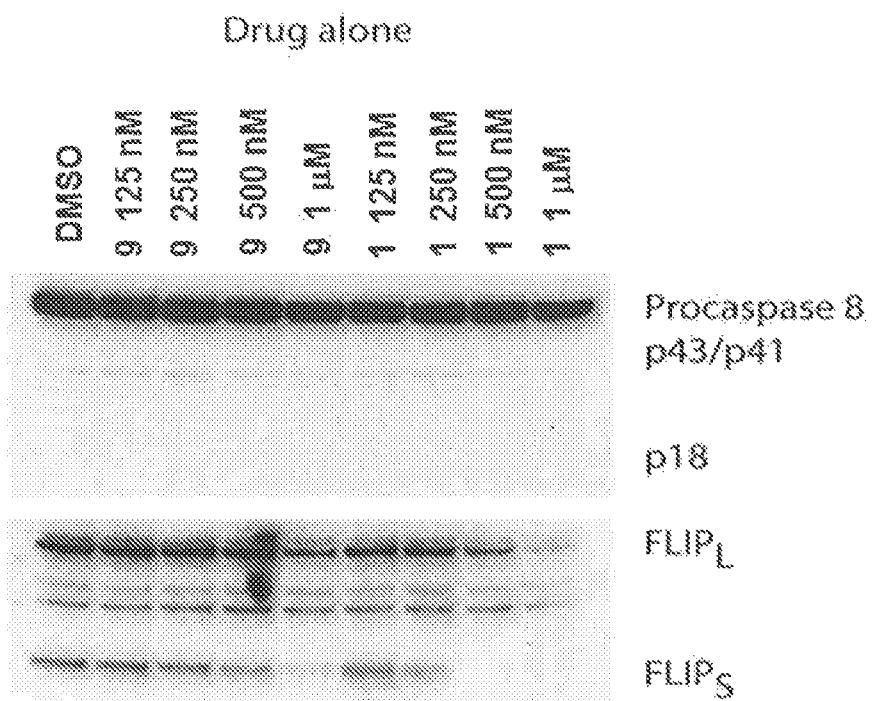
Figure 5B:
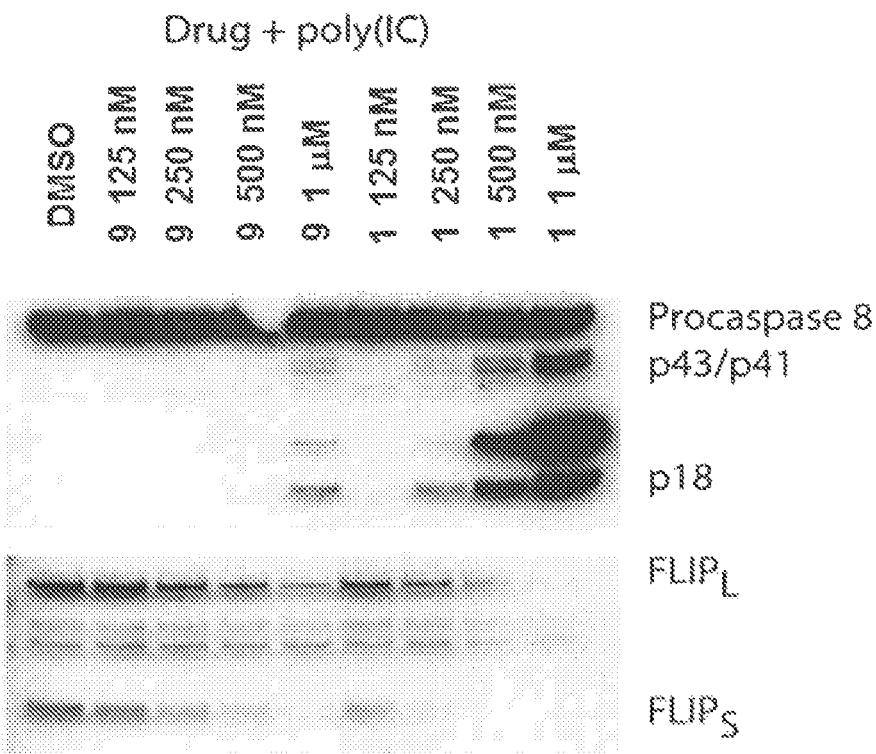

FIGS. 5A and 5B depict the effect of compounds 1 and 9 at concentrations of 125 nM, 250 nM, 500 nM, and 1 μM on caspase-8 activation and cFLIP reduction in ACHN cells in the presence (FIG. 5B) or absence (FIG. 5A) of 10 μM poly IC.

Figure 6:
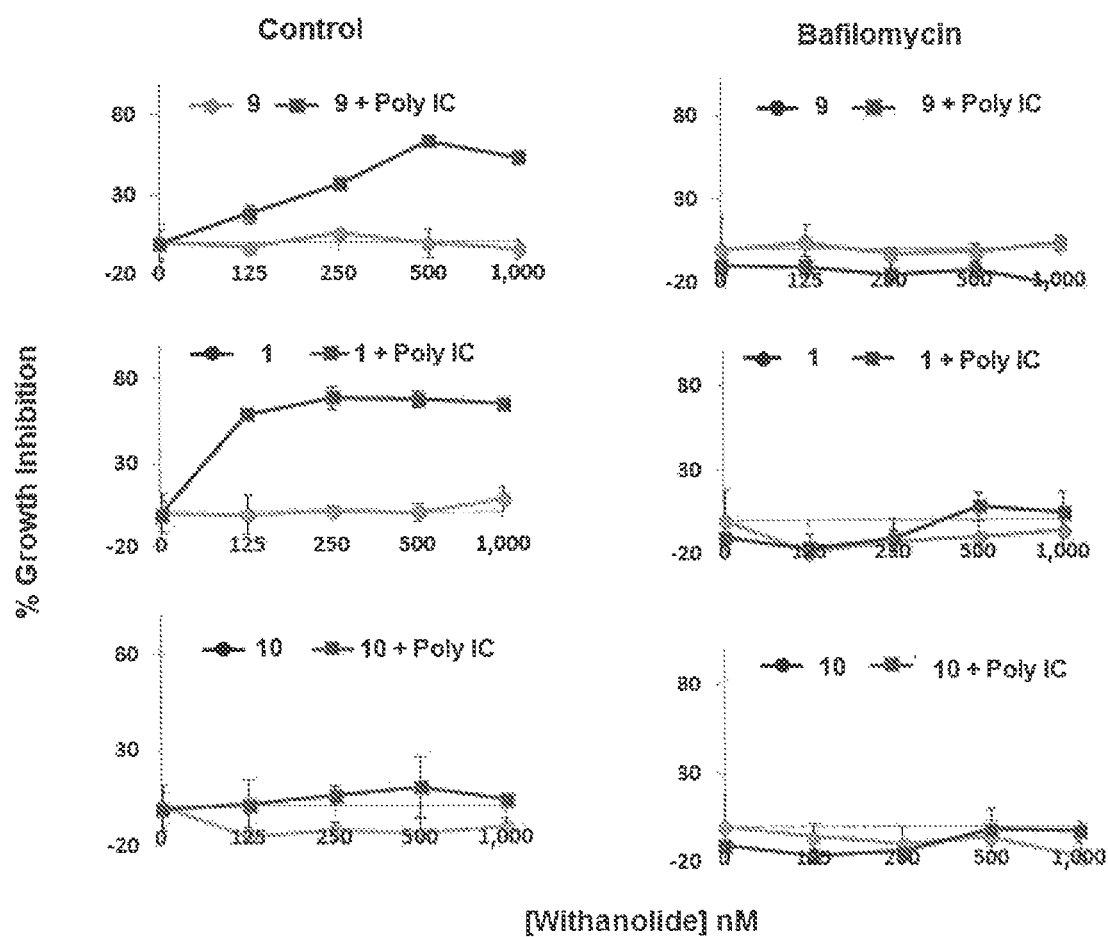

FIG. 6 depicts the effect of bafilomycin on the sensitization of SK MEL28 melanoma cells to poly IC by compound 9, 1, and 10.

Figure 7A:
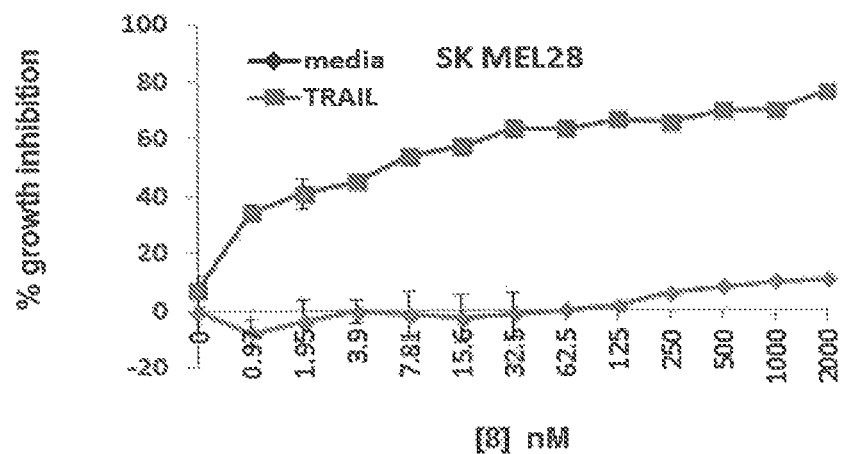
Figure 7B:
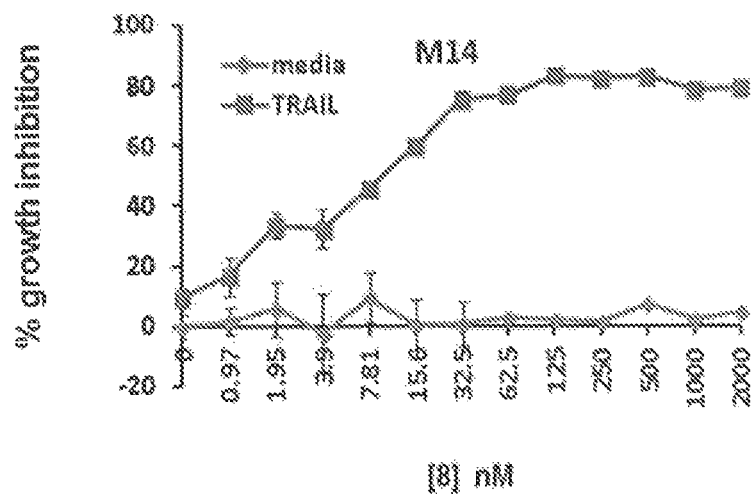
Figure 7C:
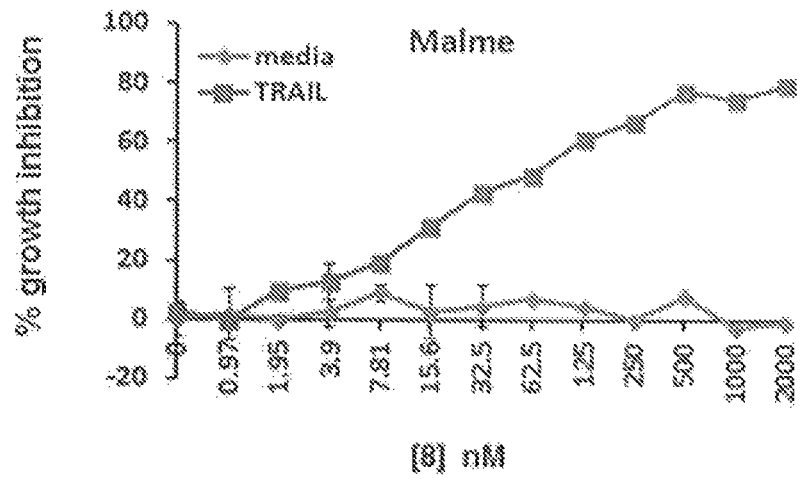

FIG. 7A-7C depicts the results of titration experiments on the sensitization of melamoma cell lines SR MEL28, M14, and Malme, respectively, by compound 8 in the presence or absence of TRAIL.

Figure 8A:
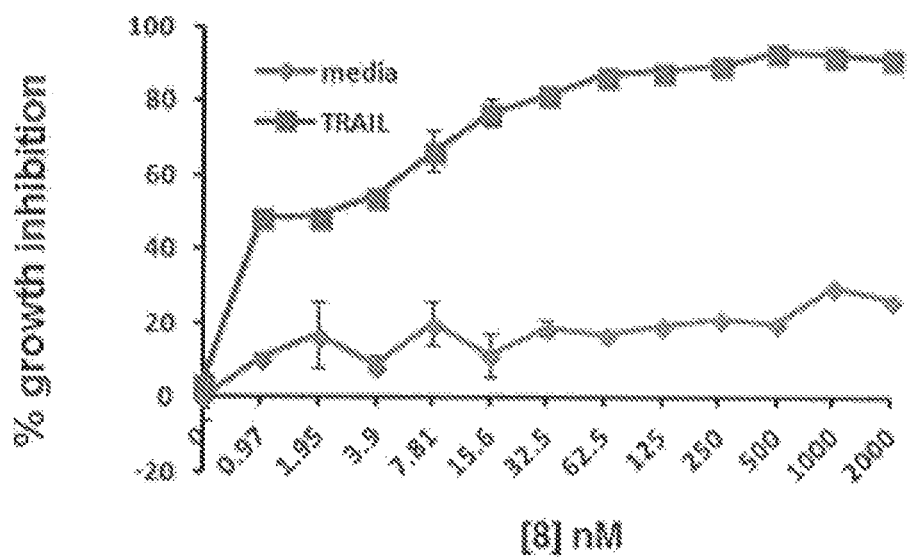
Figure 8B:
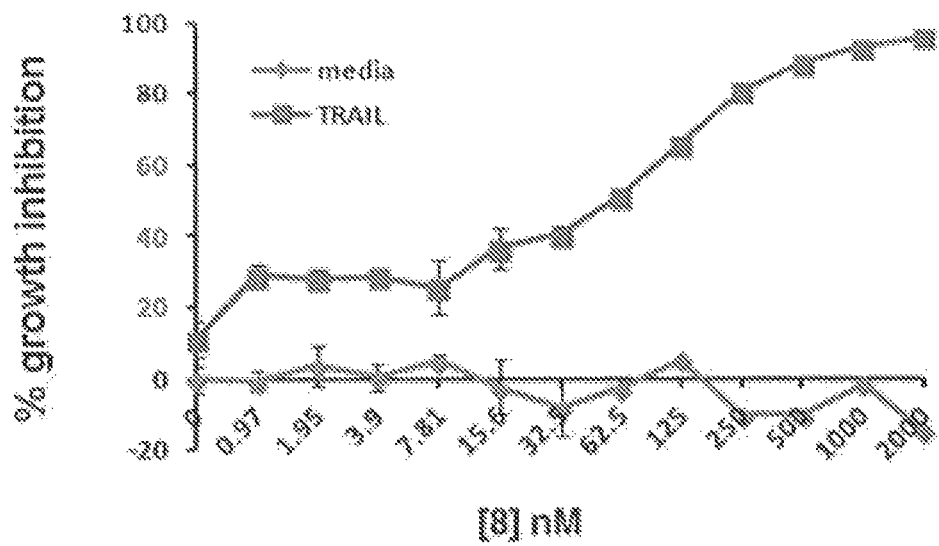

FIGS. 8A and 8B depict the results of titration experiments on the sensitization of melamoma cell lines M14 and Malme 3M, respectively, by compound 8 in the presence or absence of TRAIL.

Figure 8C:
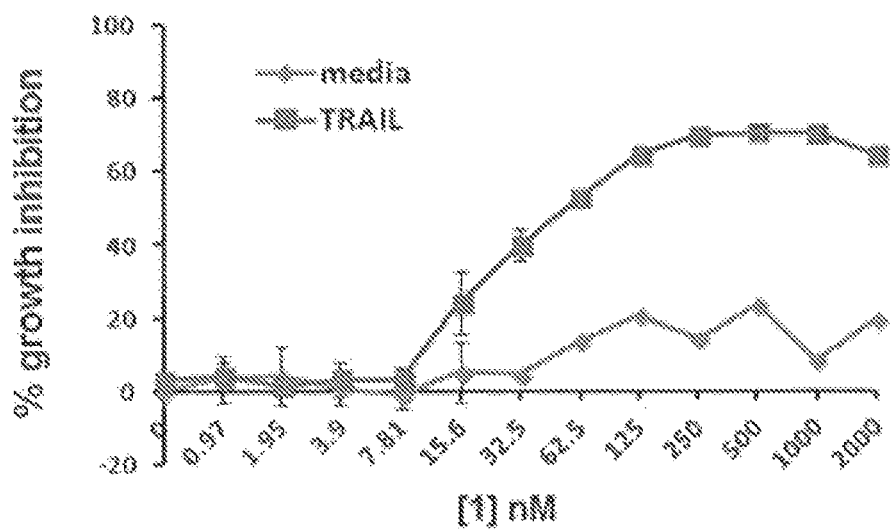
Figure 8D:
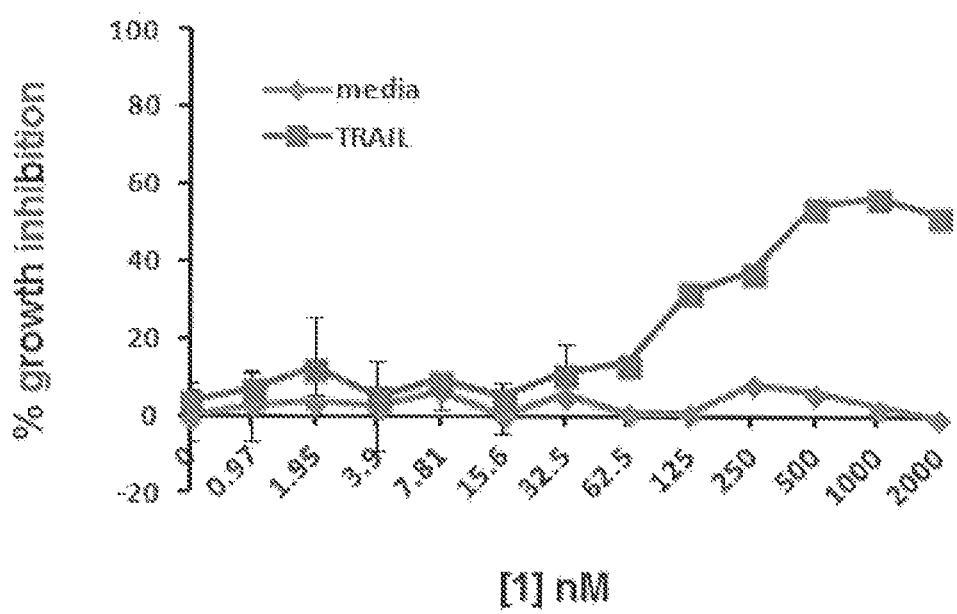

FIGS. 8C and 8D depict the results of titration experiments on the sensitization of melamoma cell lines M14 and Malme 3M, respectively, by compound 1 in the presence or absence of TRAIL.

Figure 9A:
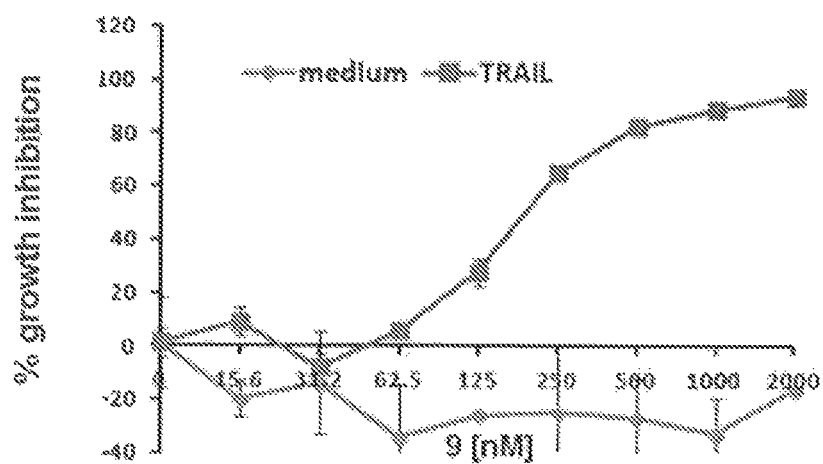
Figure 9B:
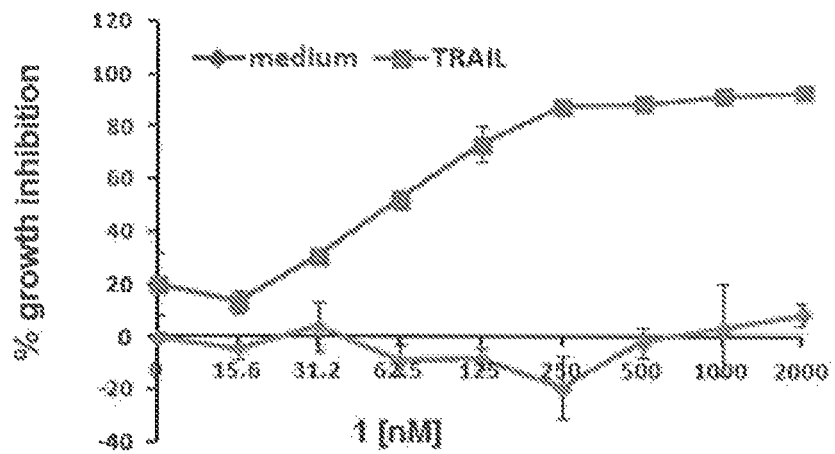
Figure 9C:
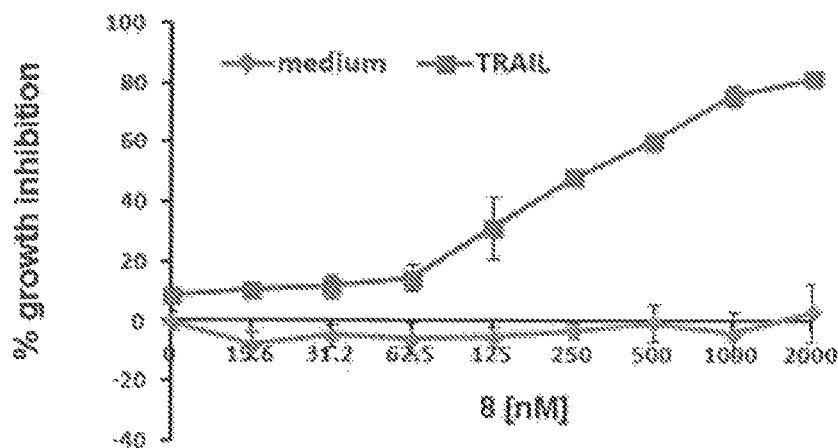

FIGS. 9A-9C depict the results of titration experiments on the sensitization of ACHN renal cancer cell, respectively, by compounds 9, 1, and 8, respectively, in the presence or absence of TRAIL.

Figure 10A:
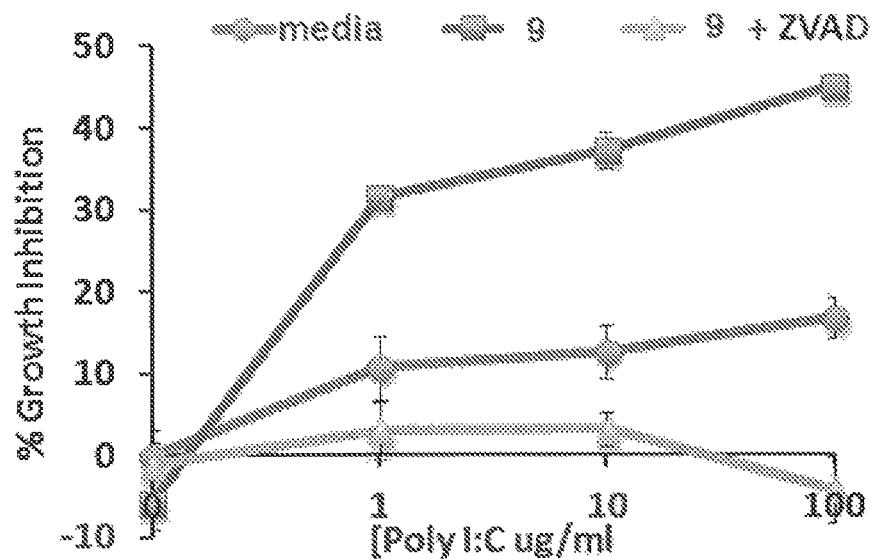
Figure 10B:
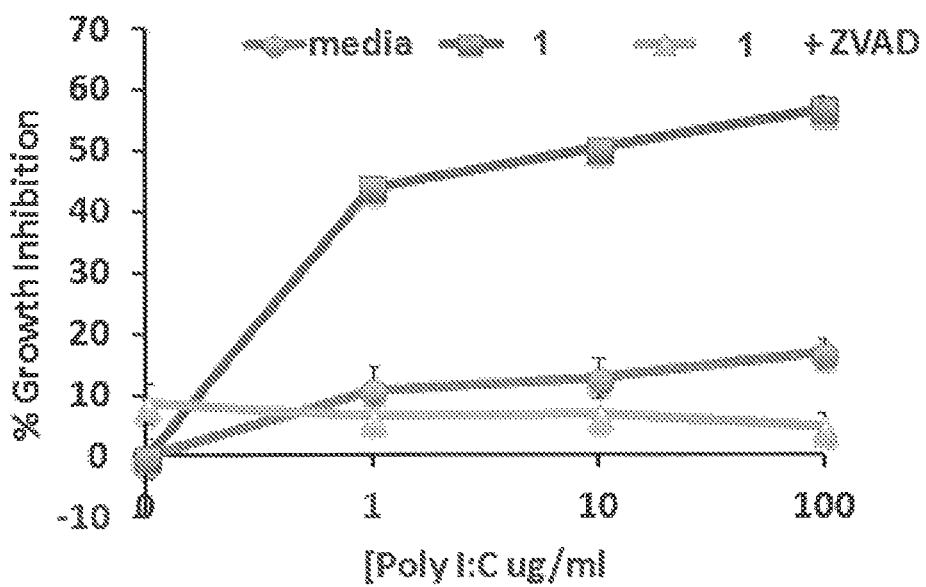

FIGS. 10A and 10B depicts the effect of the caspase inhibitor ZVAD-FMK on cell growth inhibition by poly IC in combination with compounds 9 and 1, respectively.

Figure 11:
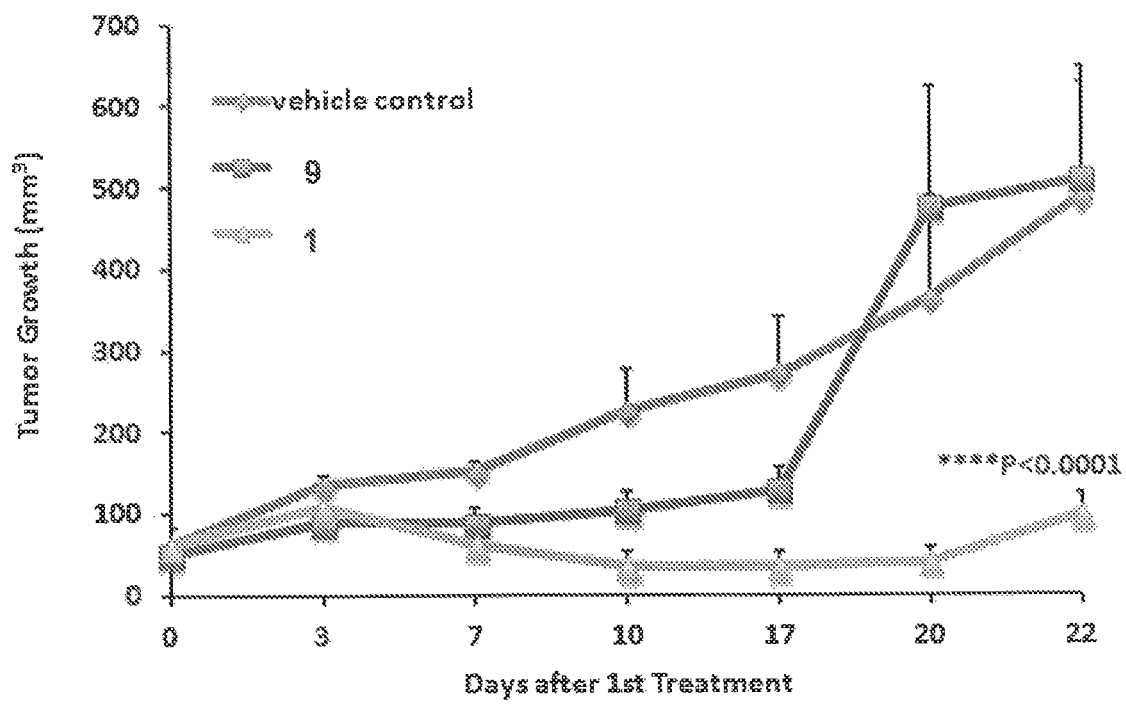

FIG. 11 depicts the effects of the effects of compounds 9 and 1 in a xenograft model of human M14 melanoma in athymic nude mice.

Figure 12:
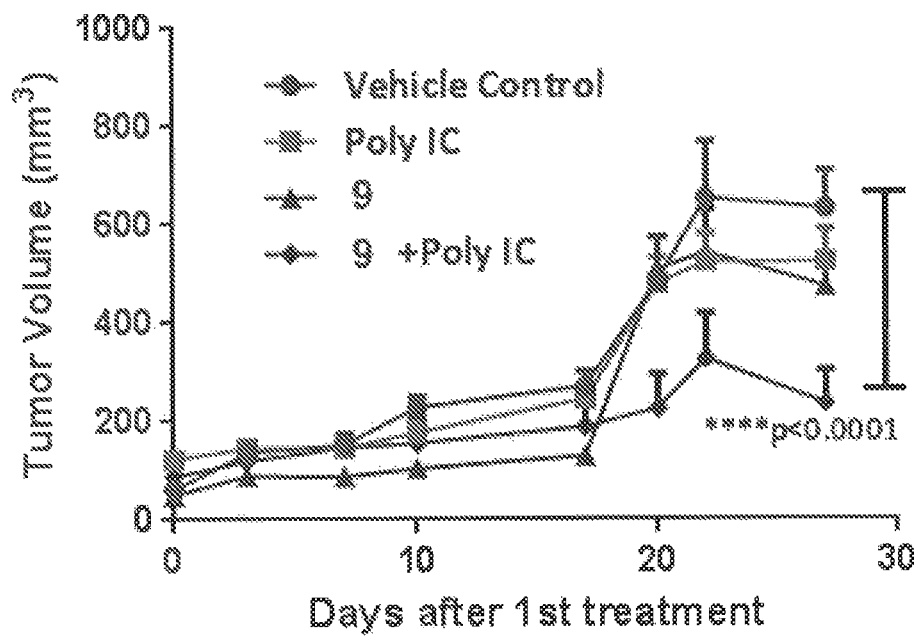

FIG. 12 depicts the effects of compound 9 alone and a combination of compound 9 and poly IC in a xenograft model of human M14 melanoma in athymic nude mice.

Figure 13A:
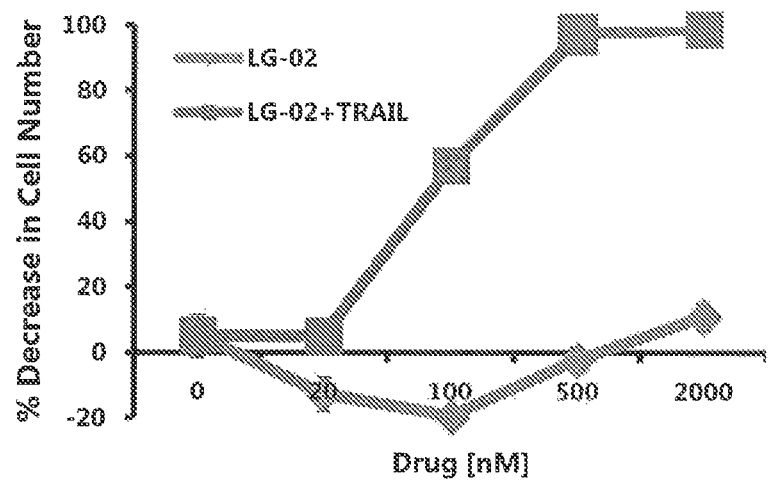

FIG. 13A shows the percentage decrease in cell number of ACHN renal carcinoma cells as a function of concentration in ACHN cells treated with compound 1 (LG-02) alone or in combination with 50 ng/mL of TRAIL.

Figure 13B:
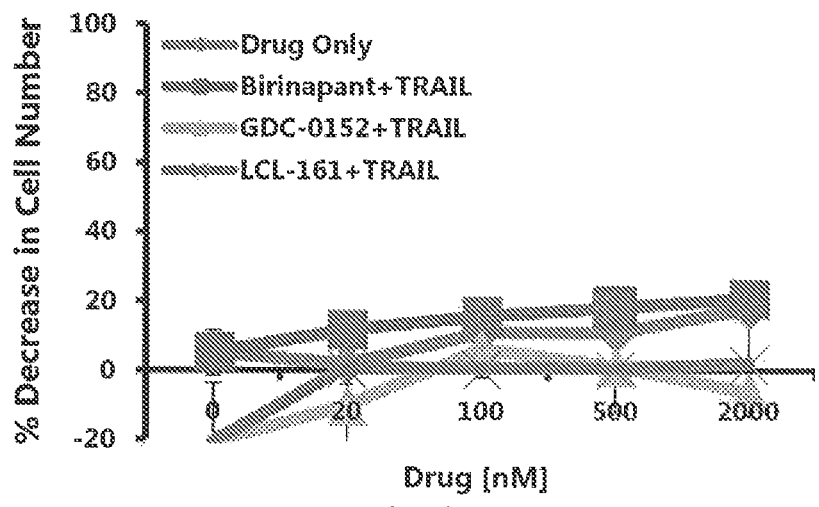

FIG. 13B shows the percentage decrease in cell number of ACHN renal carcinoma cells as a function of concentration in ACHN cells treated with birinapant, GDC-0152, or LCL-161 in combination with 50 ng/mL of TRAIL or with one of the agents alone.

Figure 13C:
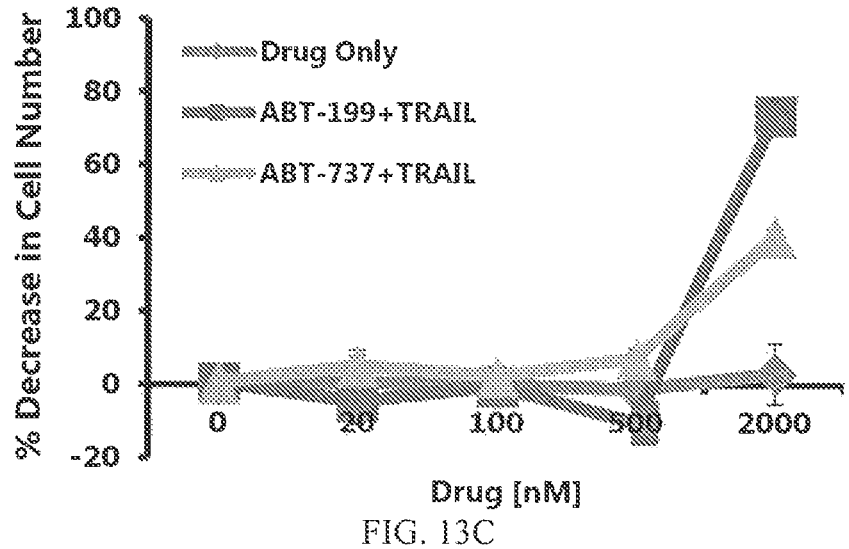

FIG. 13C shows, the percentage decrease in cell number of ACHN renal carcinoma cells as a function of concentration in ACHN cells treated with ABT-199 or ABT-737 in combination with 50 ng/mL of TRAIL or with one of the agents alone.

Figure 14A:
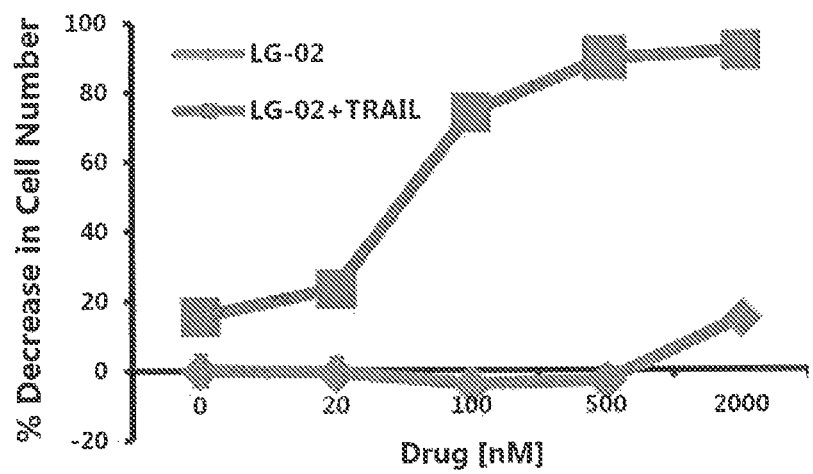

FIG. 14A shows the percentage decrease in cell number of SN12C renal carcinoma cells as a function of concentration in SN12C cells treated with compound 1 (LG-02) alone or in combination with 50 ng/mL of TRAIL.

Figure 14B:
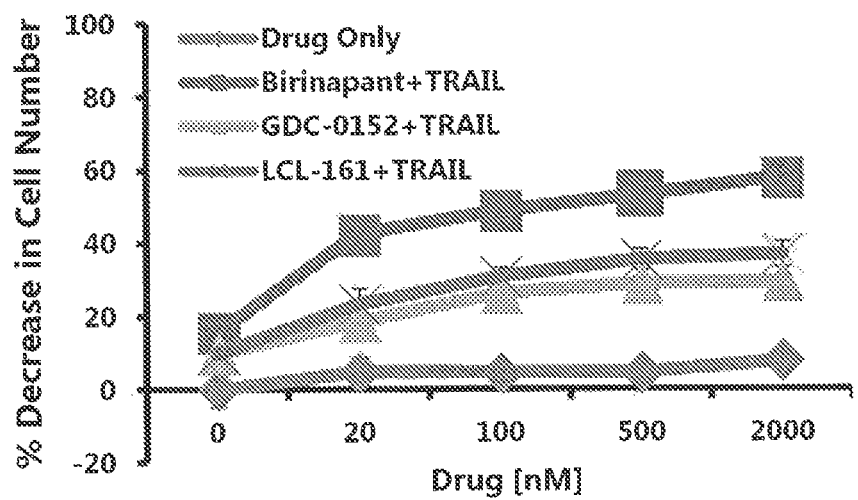

FIG. 14B shows the percentage decrease in cell number of SN12C renal carcinoma cells as a function of concentration in SN12C cells treated with birinapant, GDC-0152, or LCL-161 in combination with 50 ng/mL of TRAIL or with one of the agents alone.

Figure 14C:
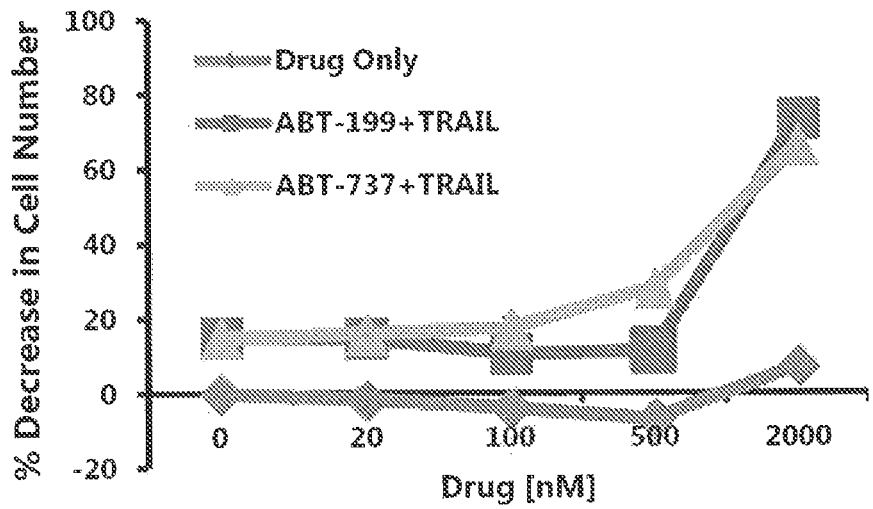

FIG. 14C shows the percentage decrease in cell number of SN12C renal carcinoma cells as a function of concentration in SN12C cells treated with ABT-199 or ABT-737 in combination with 50 ng/mL of TRAIL or with one of the agents alone.

Figure 15A:
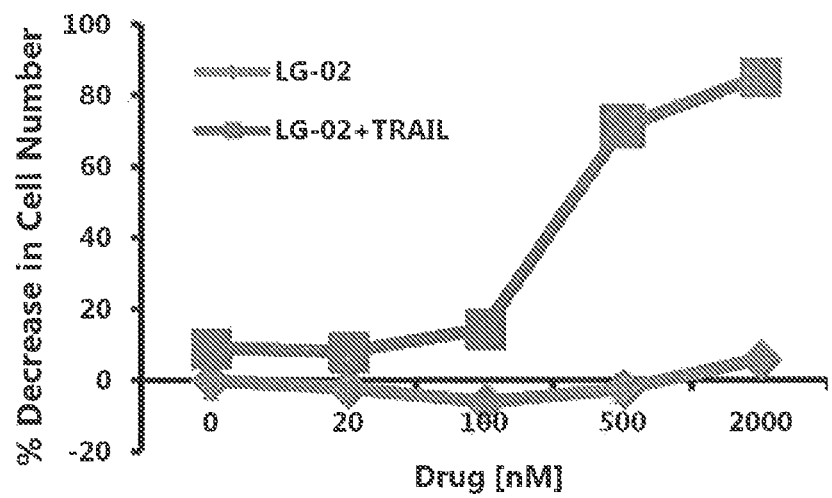

FIG. 15A shows the percentage decrease in cell number of Caki-1 renal carcinoma cells as a function of concentration in Caki-1 cells treated with compound 1 (LG-02) alone or in combination with 50 ng/mL of TRAIL.

Figure 15B:
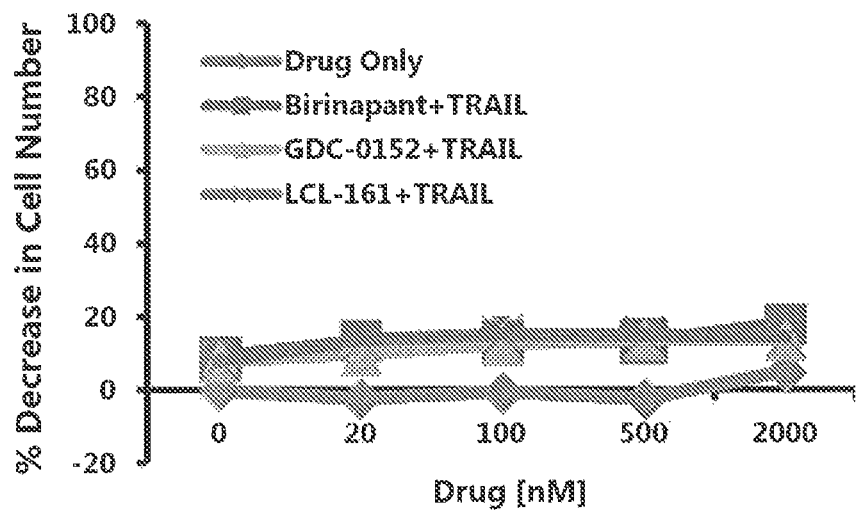

FIG. 15B shows the percentage decrease in cell number of Caki-1 renal carcinoma cells as a function of concentration in Caki-1 cells treated with birinapant, GDC-0152, or LCL-161 in combination with 50 ng/mL of TRAIL or with one of the agents alone.

Figure 15C:
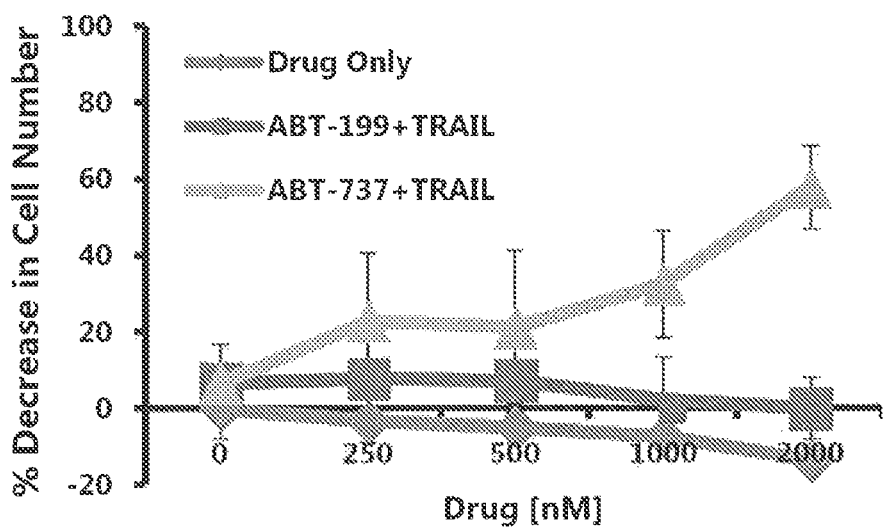

FIG. 15C shows the percentage decrease in cell number of Caki-1 renal carcinoma cells as a function of concentration in Caki-1 cells treated with ABT-199 or ABT-737 in combination with 50 ng/mL of TRAIL or with one of the agents alone.

Figure 16A:
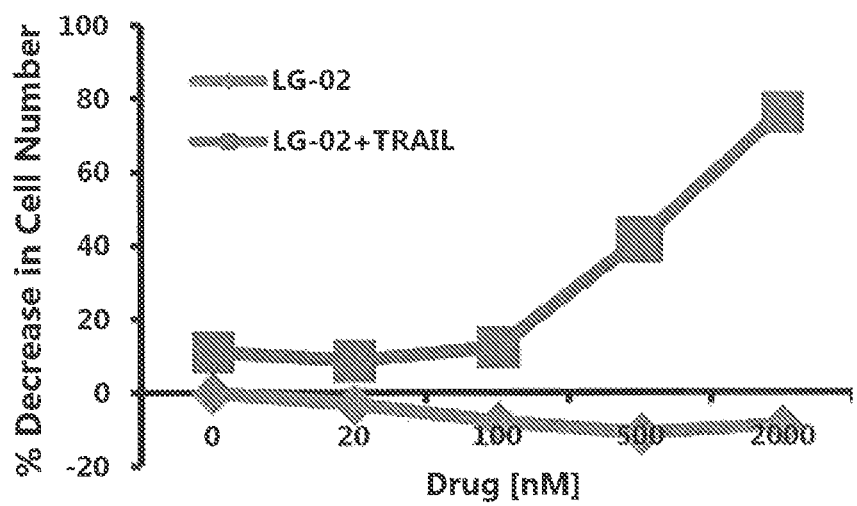

FIG. 16A shows the percentage decrease in cell number of TK-10 renal carcinoma cells as a function of concentration in TK-10 cells treated with compound 1 (LG-02) alone or in combination with 50 ng/mL of TRAIL.

Figure 16B:
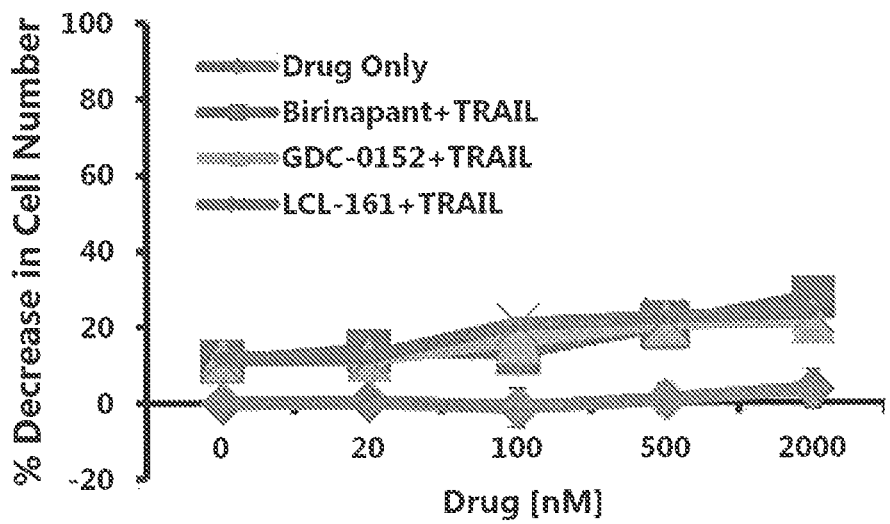

FIG. 16B shows the percentage decrease in cell number of TK-10 renal carcinoma cells as a function of concentration in AC TK-10 HN cells treated with birinapant, GDC-0152, or LCL-161 in combination with 50 ng/mL of TRAIL or with one of the agents alone.

Figure 16C:
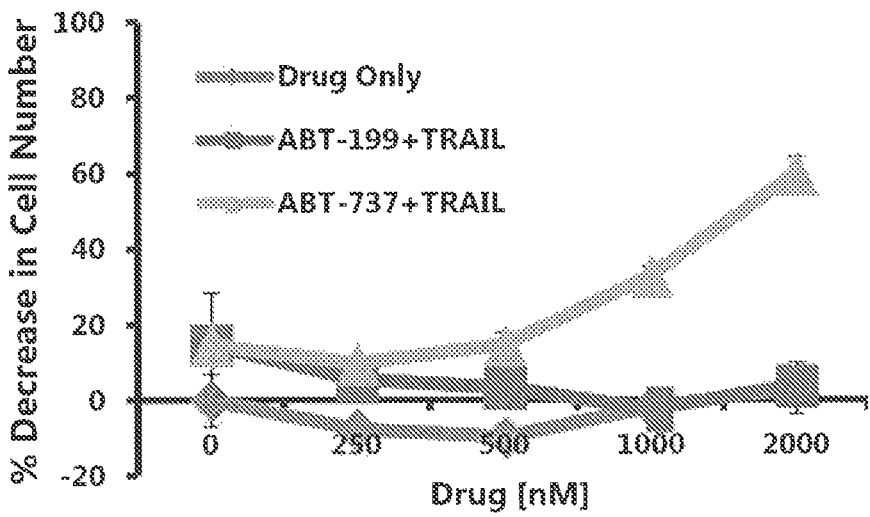

FIG. 16C shows the percentage decrease in cell number of TK-10 renal carcinoma cells as a function of concentration in TK-10 cells treated with ABT-199 or ABT-737 in combination with 50 ng/mL of TRAIL or with one of the agents alone.

Figure 17A:
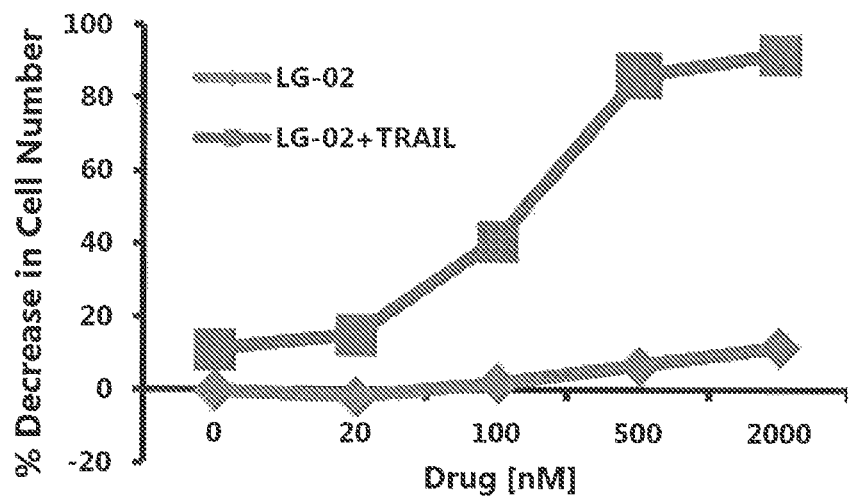

FIG. 17A shows the percentage decrease in cell number of UO-31 renal carcinoma cells as a function of concentration in UO-31 cells treated with compound 1 (LG-02) alone or in combination with 50 ng/mL of TRAIL.

Figure 17B:
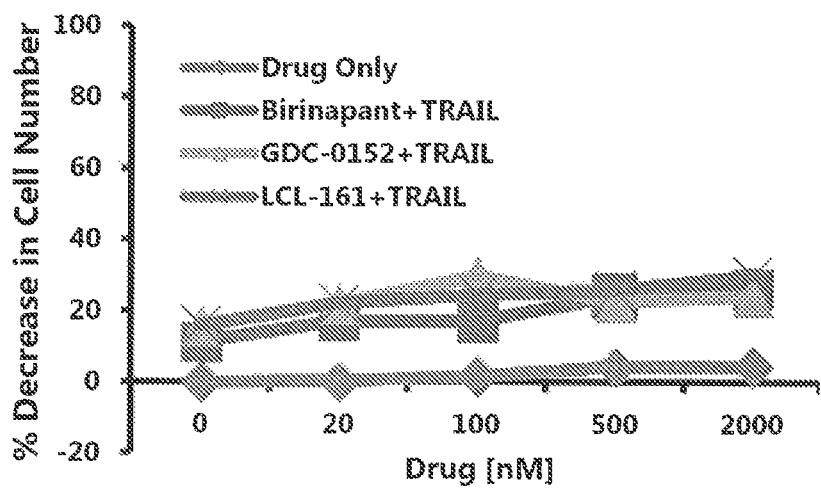

FIG. 17B shows the percentage decrease in cell number of UO-31 renal carcinoma cells as a function of concentration in UO-31 cells treated with birinapant, GDC-0152, or LCL-161 in combination with 50 ng/mL of TRAIL or with one of the agents alone.

Figure 17C:
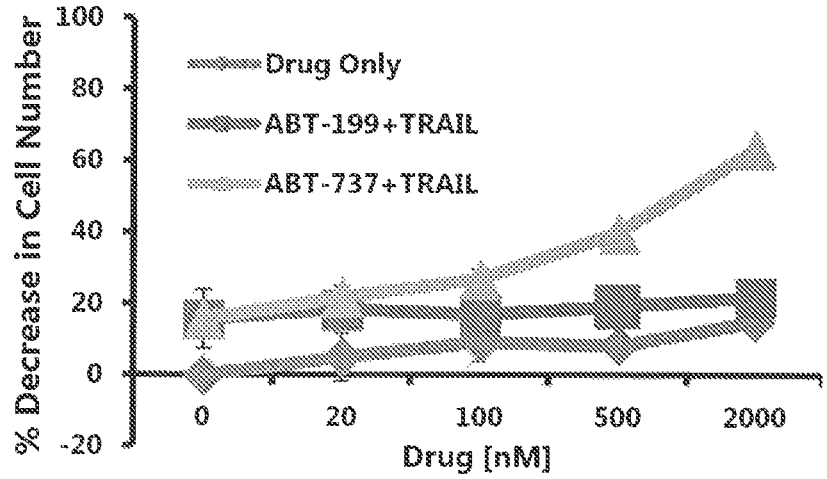

FIG. 17C shows the percentage decrease in cell number of UO-31 renal carcinoma cells as a function of concentration in UO-31 cells treated with ABT-199 or ABT-737 in combination with 50 ng/mL of TRAIL or with one of the agents alone.

Figure 18A:
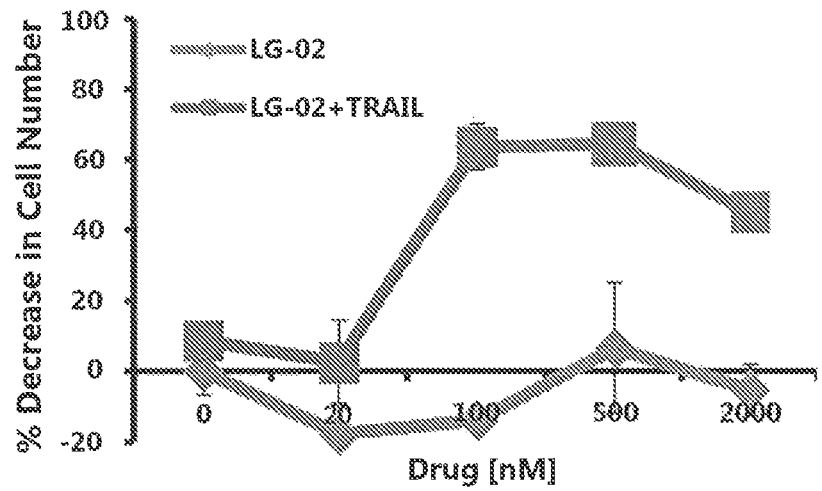

FIG. 18A shows the percentage decrease in cell number of M14 melanoma cells as a function of concentration in M14 cells treated with compound 1 (LG-02) alone or in combination with 25 ng/mL of TRAIL.

Figure 18B:
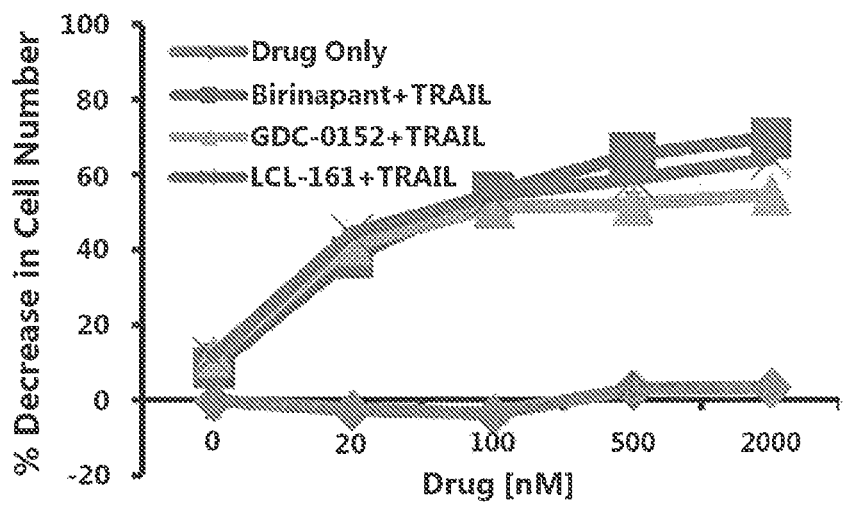

FIG. 18B shows the percentage decrease in cell number of M14 melanoma cells as a function of concentration in M14 cells treated with birinapant, GDC-0152, or LCL-161 in combination with 25 ng/mL of TRAIL or with one of the agents alone.

Figure 18C:
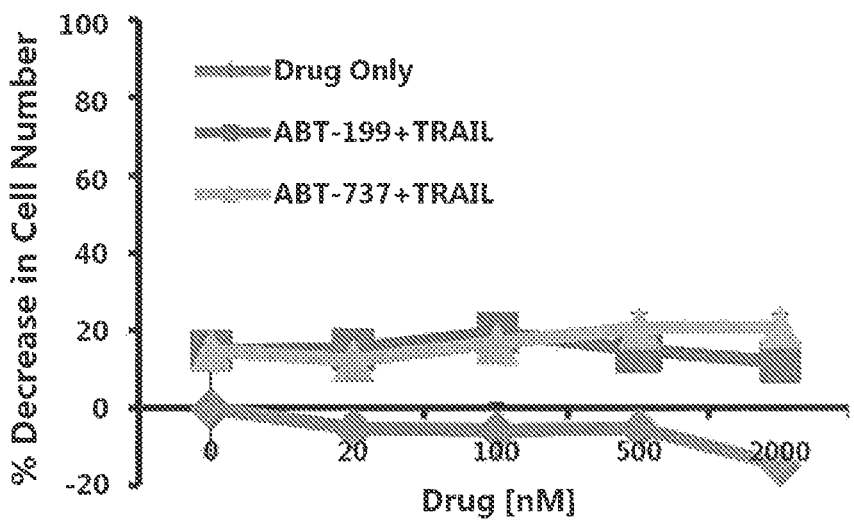

FIG. 18C shows the percentage decrease in cell number of M14 melanoma cells as a function of concentration in M14 cells treated with ABT-199 or ABT-737 in combination with 25 ng/mL of TRAIL or with one of the agents alone.

Figure 19A:
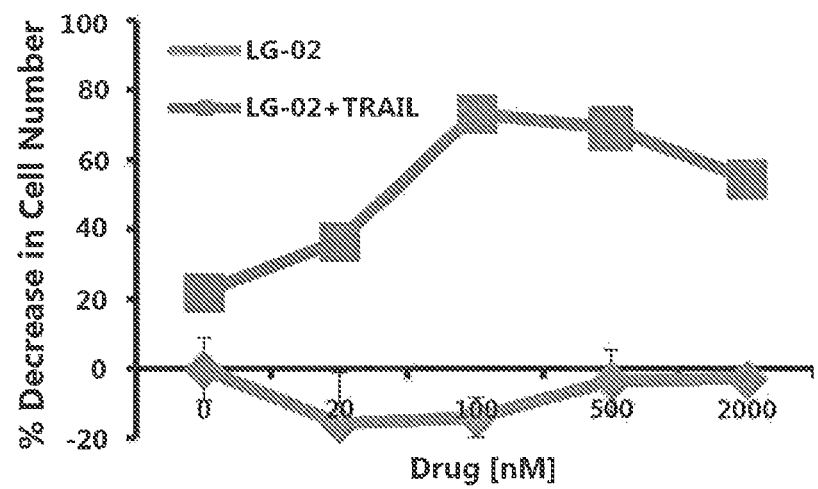

FIG. 19A shows the percentage decrease in cell number of SK-MEL-28 melanoma cells as a function of concentration in SK-MEL-28 cells treated with compound 1 (LG-02) alone or in combination with 25 ng/mL of TRAIL.

Figure 19B:
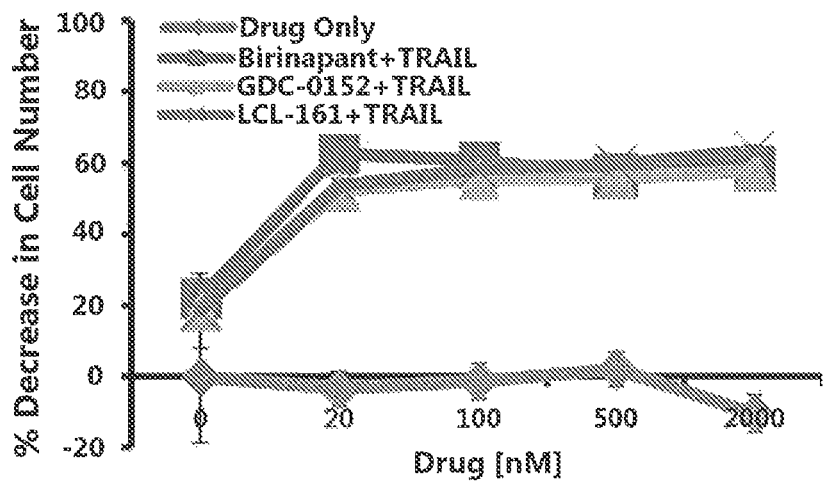

FIG. 19B shows the percentage decrease in cell number of SK-MEL-28 melanoma cells as a function of concentration in SK-MEL-28 cells treated with birinapant, GDC-0152, or LCL-161 in combination with 25 ng/mL of TRAIL or with one of the agents alone.

Figure 19C:
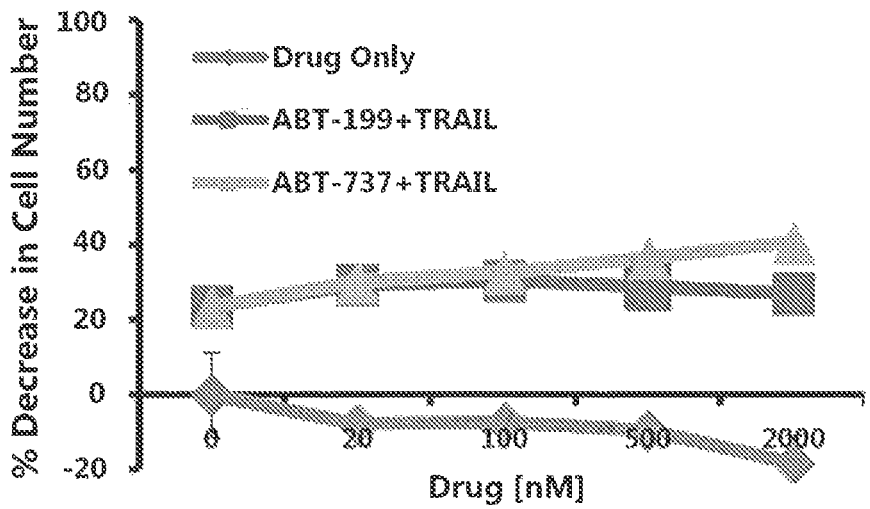

FIG. 19C shows the percentage decrease in cell number of SK-MEL-28 melanoma cells as a function of concentration in SK-MEL-28 cells treated with ABT-199 or ABT-737 in combination with 25 ng/mL of TRAIL or with one of the agents alone.

Figure 20A:
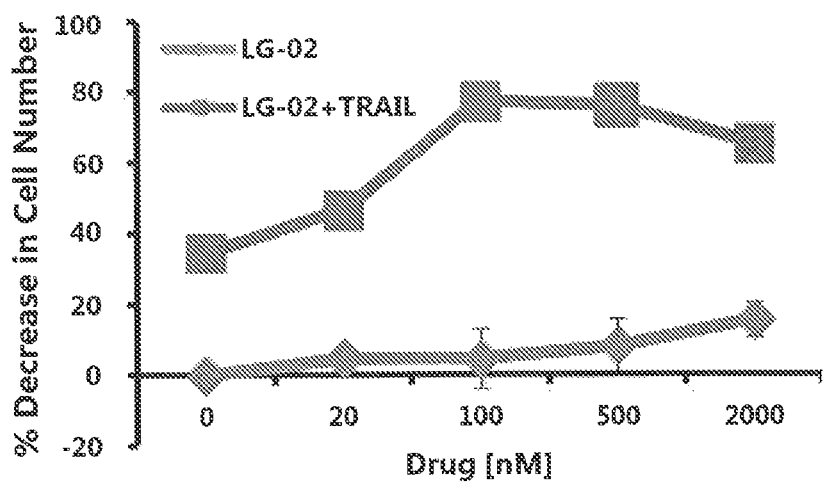

FIG. 20A shows the percentage decrease in cell number of UACC-62 melanoma cells as a function of concentration in UACC-62 cells treated with compound 1 (LG-02) alone or in combination with 25 ng/mL of TRAIL.

Figure 20B:
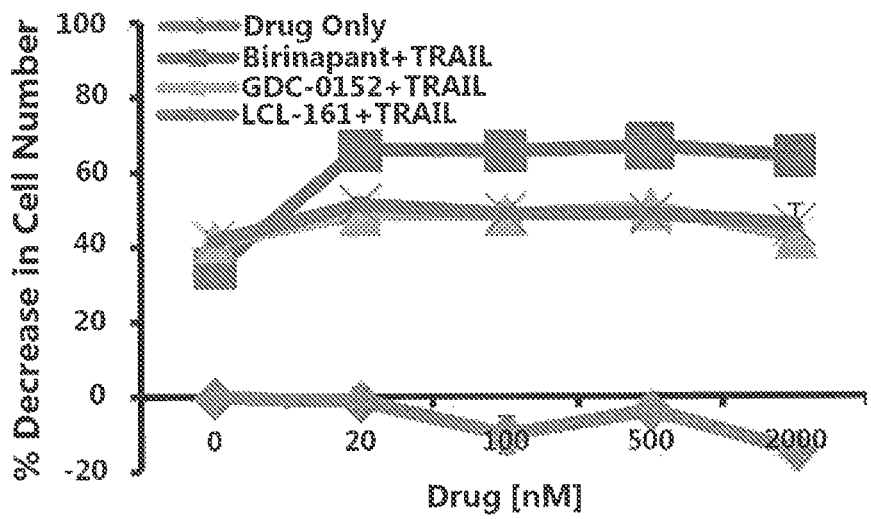

FIG. 20B shows the percentage decrease in cell number of UACC-62 melanoma cells as a function of concentration in UACC-62 HN cells treated with birinapant, GDC-0152, or LCL-161 in combination with 25 ng/mL of TRAIL or with one of the agents alone.

Figure 20C:
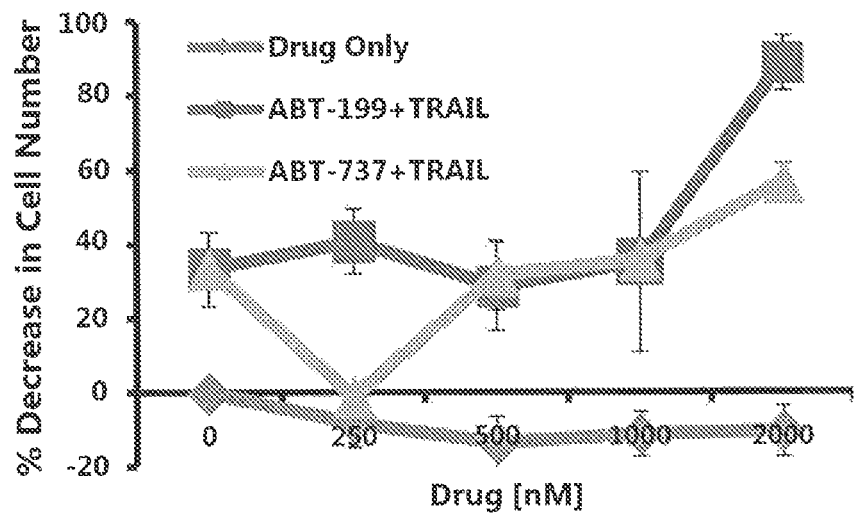

FIG. 20C shows the percentage decrease in cell number of UACC-62 melanoma cells as a function of concentration in UACC-62 HN cells treated with ABT-199 or ABT-737 in combination with 25 ng/mL of TRAIL or with one of the agents alone.

Figure 21A:
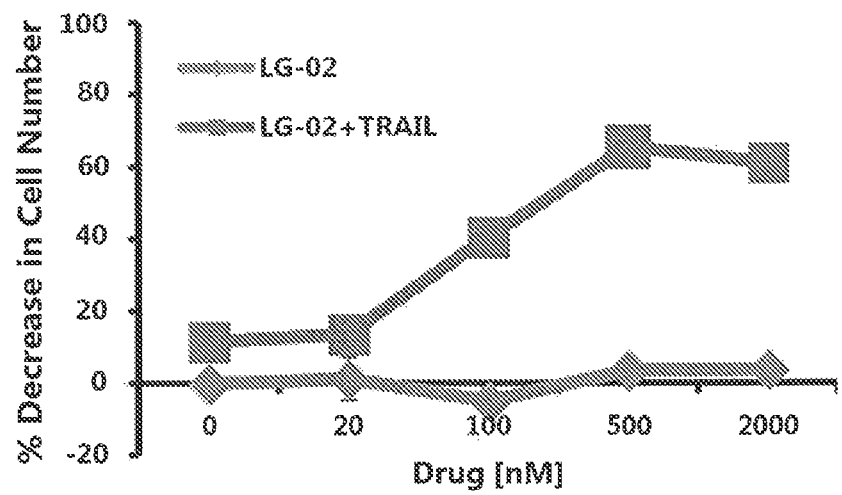

FIG. 21A shows the percentage decrease in cell number of SK-MEL-5 melanoma cells as a function of concentration in SK-MEL-5 cells treated with compound 1 (LG-02) alone or in combination with 25 ng/mL of TRAIL.

Figure 21B:
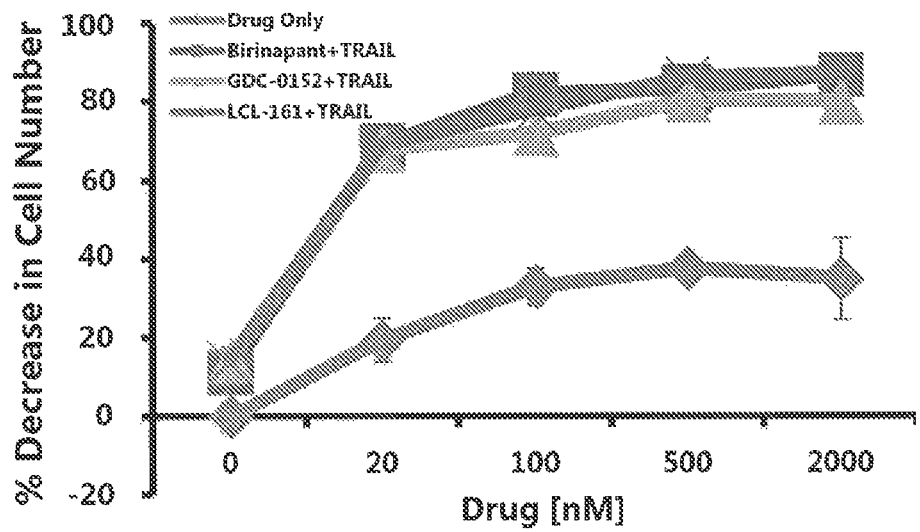

FIG. 21B shows the percentage decrease in cell number of SK-MEL-5 melanoma cells as a function of concentration in SK-MEL-5 cells treated with birinapant, GDC-0152, or LCL-161 in combination with 25 ng/mL of TRAIL or with one of the agents alone.

Figure 21C:
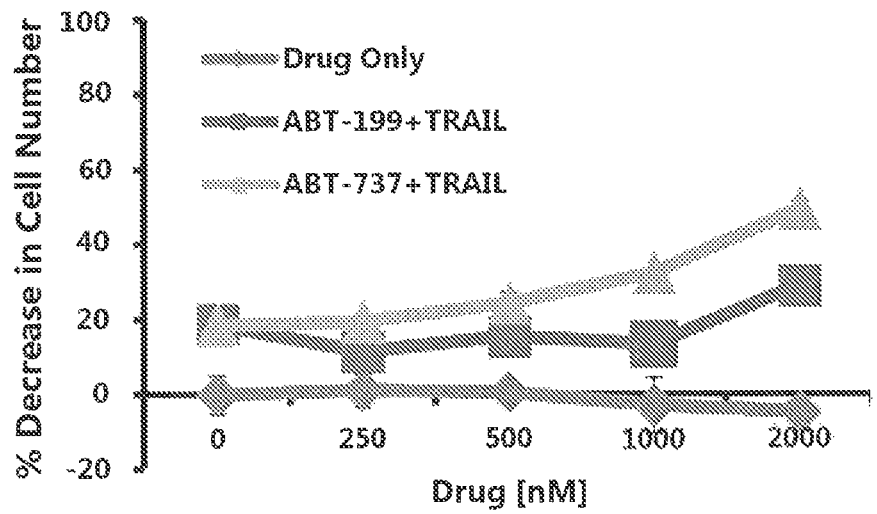

FIG. 21C shows the percentage decrease in cell number of SR-MEL-5 melanoma cells as a function of concentration in SK-MEL-5 cells treated with ABT-199 or ABT-737 in combination with 25 ng/mL of TRAIL or with one of the agents alone.

Figure 22A:
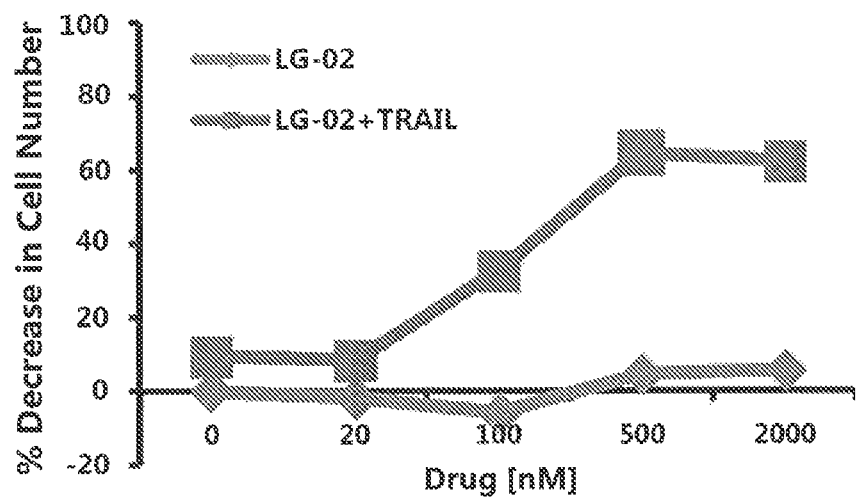

FIG. 22A shows the percentage decrease in cell number of MALME-3M melanoma cells as a function of concentration in MALME-3M cells treated with compound 1 (LG-02) alone or in combination with 25 ng/mL of TRAIL.

Figure 22B:
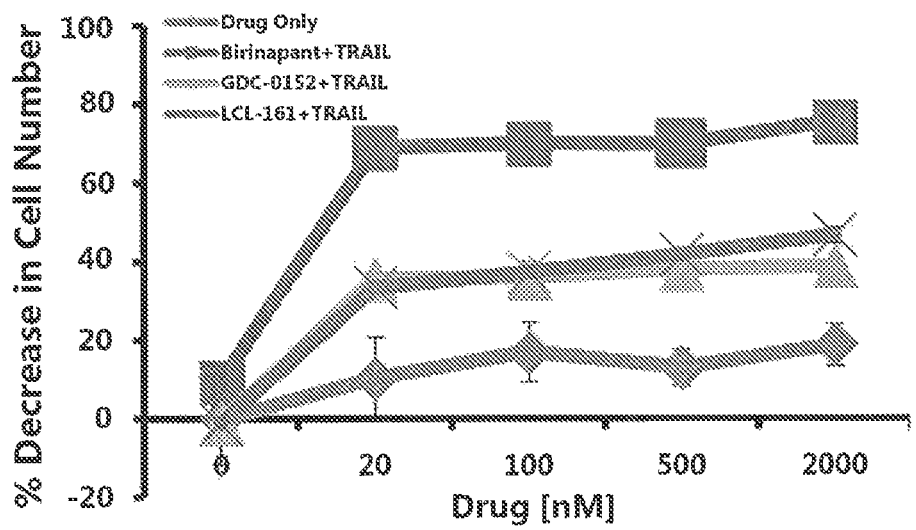

FIG. 22B shows the percentage decrease in cell number of MALME-3M melanoma cells as a function of concentration in MALME-3M cells treated with birinapant, GDC-0152, or LCL-161 in combination with 25 ng/mL of TRAIL or with one of the agents alone.

Figure 22C:
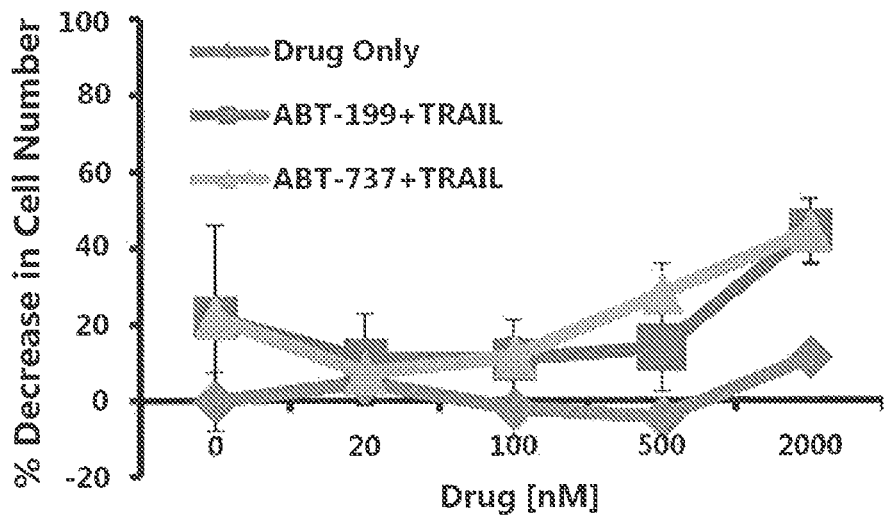

FIG. 22C shows the percentage decrease in cell number of MALME-3M melanoma cells as a function of concentration in MALME-3M cells treated with ABT-199 ABT-737 in combination with 25 ng/mL of TRAIL or with one of the agents alone.

Figure 23A:
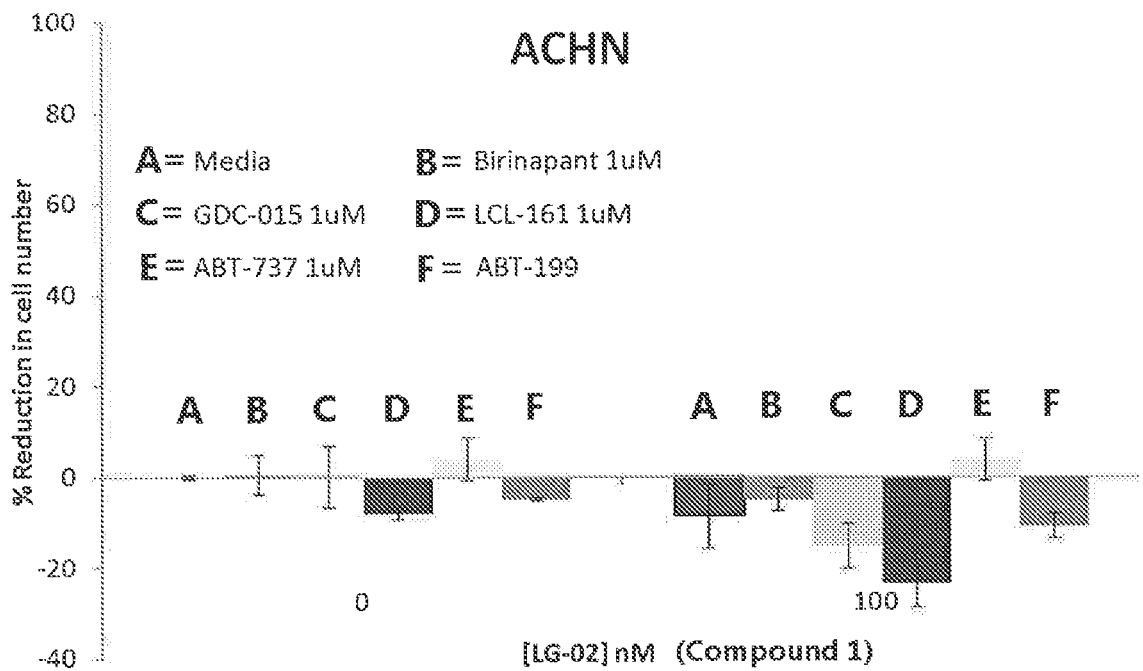

FIG. 23A shows the percentage decrease in cell number of ACHN cells as a function of concentration in ACHN cells treated with 1000 nM of birinapant, GDC-015, LCL-161, ABT-737 or venetoclax and increasing concentrations of compound 1 in the absence of TRAIL.

Figure 23B:
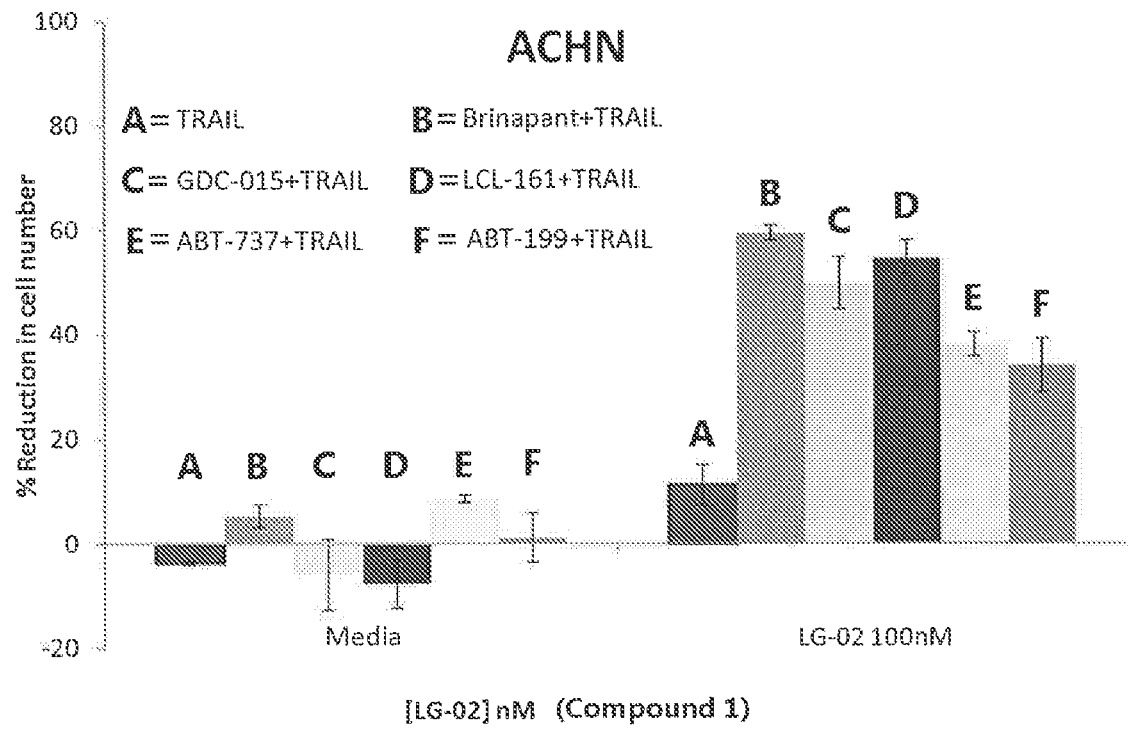

FIG. 23B shows the percentage decrease in cell number of ACHN cells as a function of concentration in ACHN cells treated with 1000 nM of birinapant, GDC-015, LCL-161, ABT-737 or venetoclax in combination with TRAIL and increasing concentrations of compound 1.

Figure 24A:
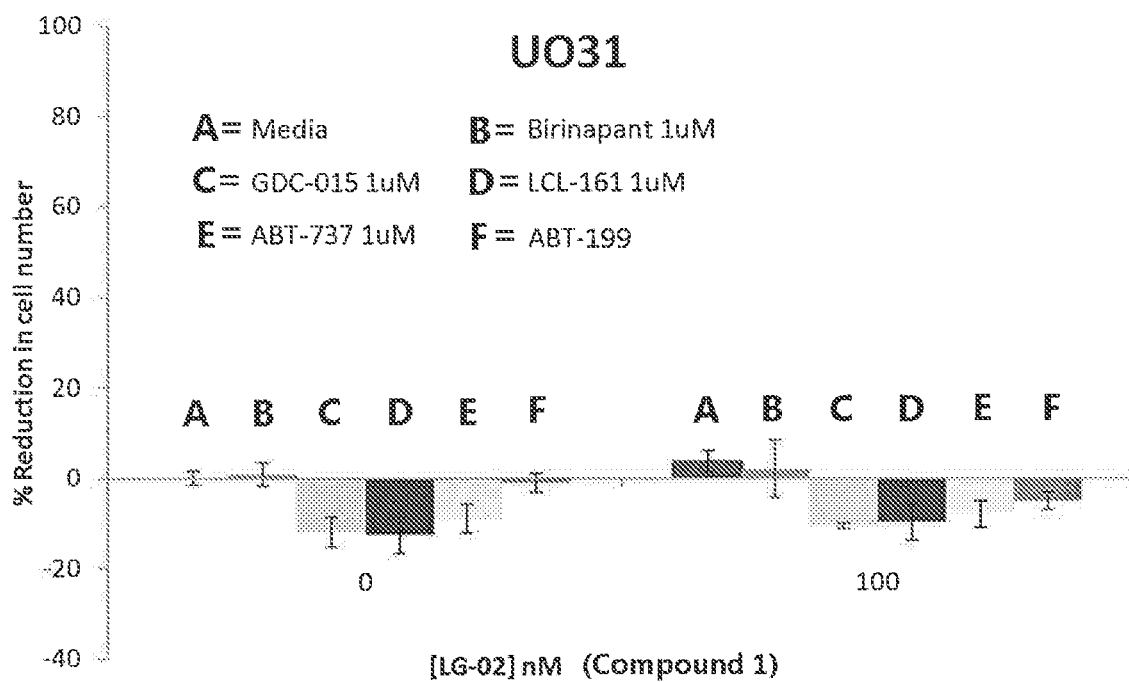

FIG. 24A shows the percentage decrease in cell number of UO31 cells as a function of concentration in ACHN cells treated with 1000 nM of birinapant, GDC-015, LCL-161, ABT-737 or venetoclax and increasing concentrations of compound 1 in the absence of TRAIL.

Figure 24B:
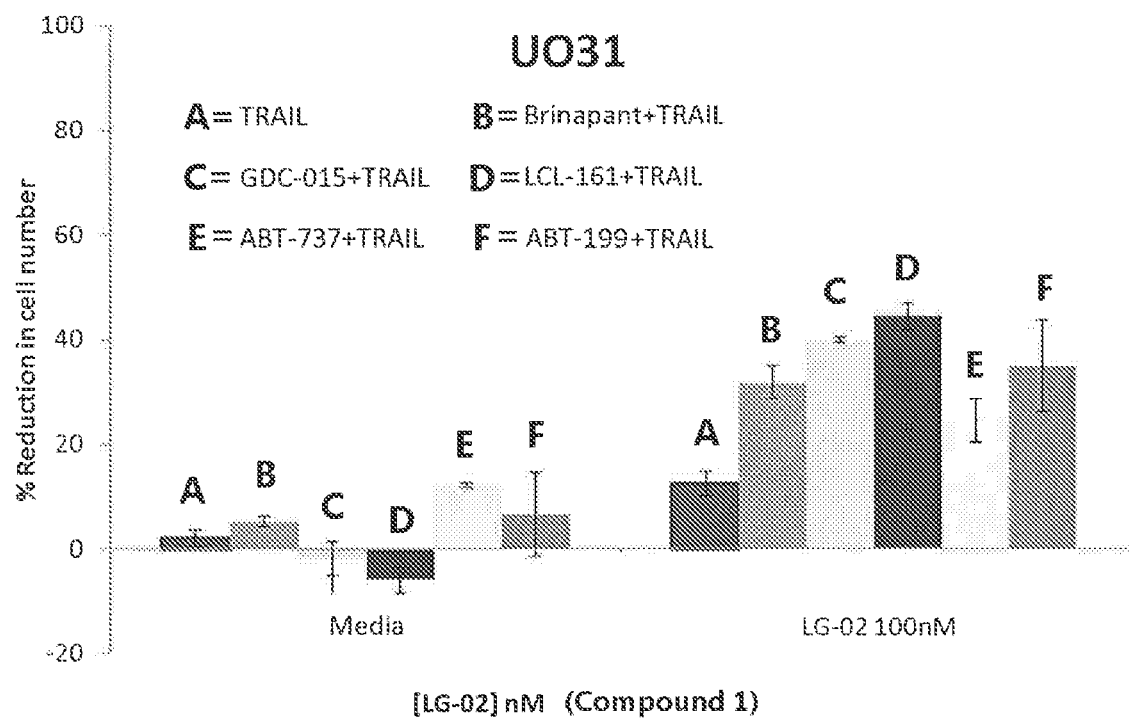

FIG. 24B shows the percentage decrease in cell number of UO31 cells as a function of concentration in ACHN cells treated with 1000 nM of birinapant, GDC-015, LCL-161, ABT-737 or venetoclax in combination with TRAIL and increasing concentrations of compound 1.

DETAILED DESCRIPTION OF THE INVENTION

The invention provides a method of synergistically enhancing the response of cancer cells to treatment with an apoptosis inducing ligand, which method comprises contacting the cancer cells with an effective amount of an apoptosis inducing ligand in conjunction with an effective amount of a sensitizer, whereby a synergistic enhancement of the response is obtained. The sensitizer is a compound of the formula:

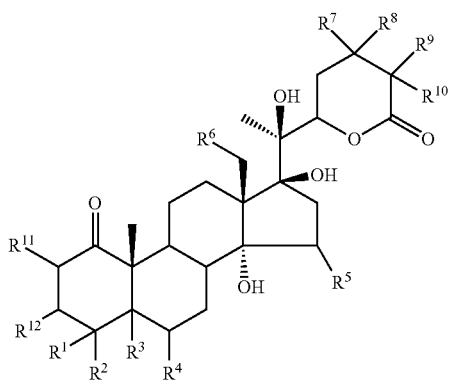

wherein $R^1$-$R^{12}$ are as described herein.

By "enhancing the response" is meant that the apoptosis inducing ligand has a greater effect (e.g., at least a 5% increase, at least a 10% increase, at least a 20% increase, at least a 30% increase, at least a 40% increase, at least a 50% increase, at least a 60% increase, at least a 70% increase, at least an 80% increase, etc.) in the presence of the sensitizer than in the absence of the sensitizer. Since the apoptosis inducing ligand causes apoptosis in cancer cells, if a sensitizer sensitizes the cancer cells to the apoptosis inducing ligand, the cancerous cell is more susceptible to apoptosis triggered by the apoptosis inducing ligand, thereby making it more likely to experience programmed cell death as a result of use of the inventive method.

The invention also provides a method of inducing apoptosis in cancer cells in a mammal that are resistant to treatment with an apoptosis-inducing ligand, comprising (a) sensitizing the cancer cells by contacting the cancer cells with a sensitizer, and (b) contacting the cancer cells with an effective amount of an apoptosis-inducing ligand, wherein apoptosis is induced in the cancer cells. The sensitizer is a compound of the formula:

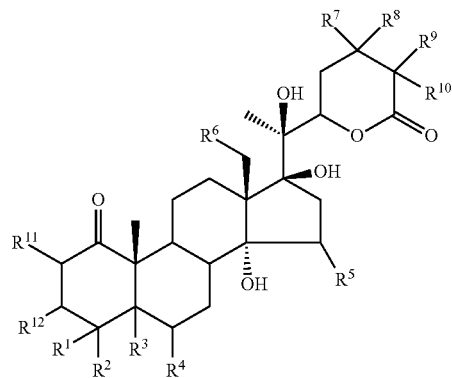

wherein $R^1$-$R^{12}$ are as described herein.

In an embodiment, the compound is of the formula:

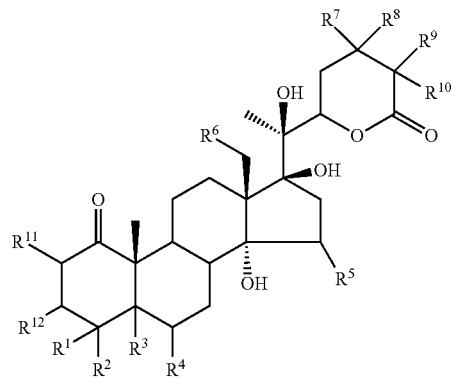

wherein $R^1$ and $R^2$ are independently selected from H, OH, $C_1$-$C_6$ acyloxy, $C_1$-$C_6$ alkylcarbonate, heteroarylcarbonyloxy, a group of the formula:

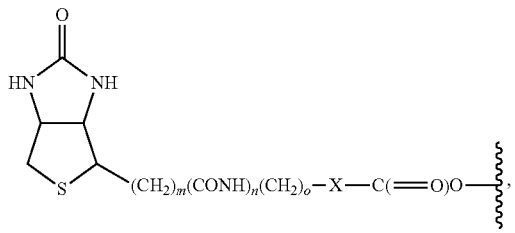

or, $R^1$ and $R^2$ taken together, form =O,
X is NH or is absent,
m and o are integers of from 1 to about 10,
n is 0 or 1, $R^3$ and $R^4$ are independently OH or $C_1$-$C_6$ alkoxy or, taken together, form a double bond or an epoxy ring, $R^5$ is H or $C_1$-$C_6$ acyloxy, $R^6$ is H, OH, or $C_1$-$C_6$ acyloxy, or $R^7$ and $R^9$ are independently $CH_2OH$ or

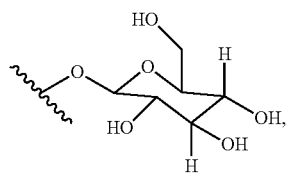 [SMILES: *OC1OC(CO)C(O)C(O)C1O]

$R^8$ and $R^{10}$, taken together with the carbon atoms to which they are attached, form a double bond or an epoxy ring, and $R^{11}$ and $R^{12}$ are both H, $R^{11}$ is H and $R^{12}$ is —$OSO_3H$, $R^{11}$ is H and $R^{12}$ is imidazolyl, or $R^{11}$ and $R^{12}$, taken together with the carbon atoms to which they are attached, form a double bond Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "acyloxy" refers to a group having the moiety: C—C(=O)—O—. The term "alkylcarbonate" refers to a group having the moiety: C—O—C(=O)—O—. The term "heteroarylcarbonyloxy" refers to a group having the moiety: heteroaryl-C(=O)—O—.

The term "heteroaryl" refers to 3-7 membered rings which are heteroaromatic, comprising carbon and one or more heteroatoms such as O, N, and S, and optionally hydrogen; optionally in combination with one or more aromatic rings. Examples of heteroaryl groups include pyridyl, pyranyl, furanyl, thienyl, furyl, thiophenyl, purinyl, pyrimidinyl, thiazolyl, thiazolidinyl, thiazolinyl, oxazolyl, pyrazolyl, imidazolyl, tetrazolyl, tetrazinyl, benzoxazolyl, quinolinyl, and isoquinolinyl.

In accordance with an embodiment of the invention, $R^{11}$ and $R^{12}$, taken together, form a double bond.

In accordance with an embodiment of the invention, $R^3$ and $R^4$, taken together, form an epoxy ring.

In accordance with an embodiment of the invention, $R^5$ is H.

In accordance with an embodiment of the invention, $R^7$ and $R^9$ are $CH_3$ and wherein $R^8$ and $R^{10}$, taken together, form a double bond.

In accordance with a specific embodiment of the invention, $R^1$ and $R^2$ are H.

In accordance with a specific embodiment of the invention, the compound is of the formula:

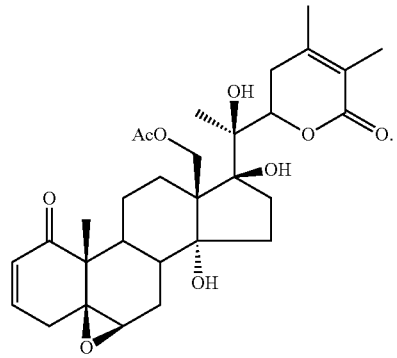 [SMILES: CC(=O)OC[C@]12CCC3C(C[C@H]4O[C@]45CC=CC(=O)[C@]35C)[C@]1(O)CC[C@@]2(O)[C@@](C)(O)C1CC(C)=C(C)C(=O)O1]

In accordance with a specific embodiment of the invention, $R^1$ is H and $R^2$ is OH.

In accordance with the above embodiment, $R^6$ is H.

In accordance with a specific embodiment of the invention, the compound is of the formula:

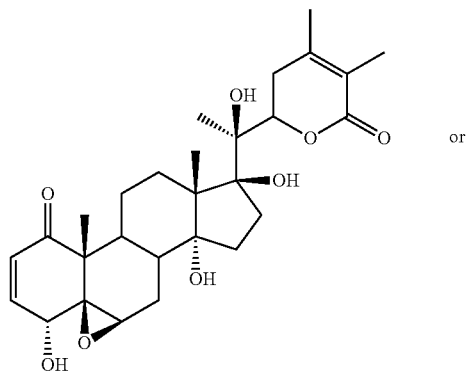

or

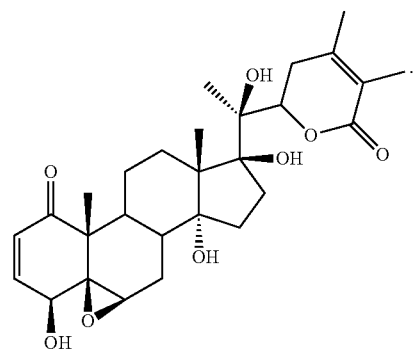

In accordance with a specific embodiment of the invention, $R^1$ is H and $R^2$ is $C_1$-$C_6$ acyloxy.

In accordance with the above embodiment, the compound is of the formula:

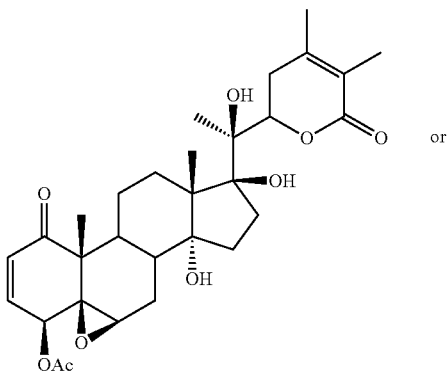

or

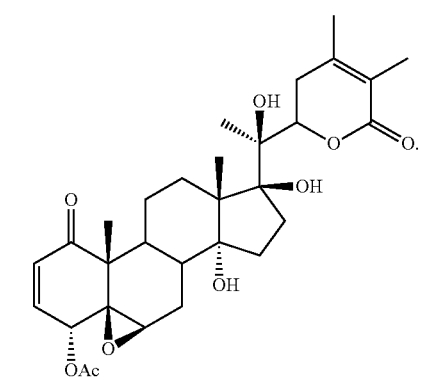

In accordance with a specific embodiment of the invention, $R^1$ is H and $R^2$ is heteroarylcarbonyloxy.

In accordance with the above embodiment, the compound is of the formula:

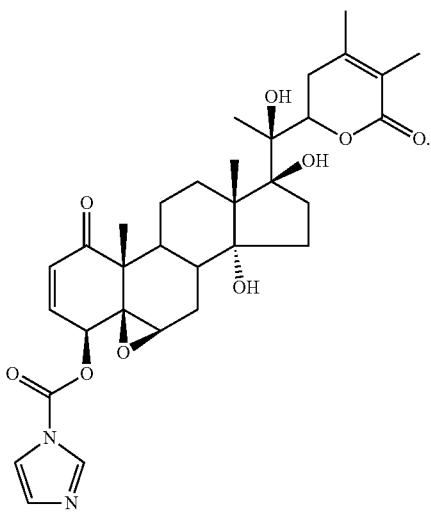 [SMILES: CC1=C(C)C(=O)OC([C@](C)(O)[C@]2(O)CC[C@@]3(O)C4C[C@H]5O[C@]56[C@@H](OC(=O)n5ccnc5)C=CC(=O)[C@]6(C)C4CC[C@]23C)C1]

In accordance with a specific embodiment of the invention, $R^1$ is H and $R^2$ is a group of the formula:

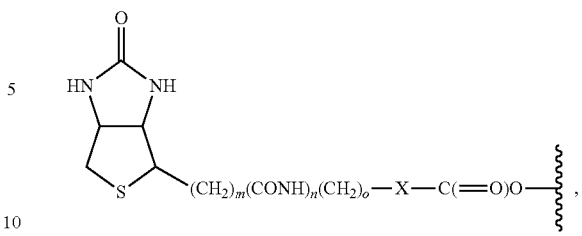

m and o are integers of from 1 to about 10, and n is 0 or 1.

In accordance with the above embodiment, the compound is of the formula:

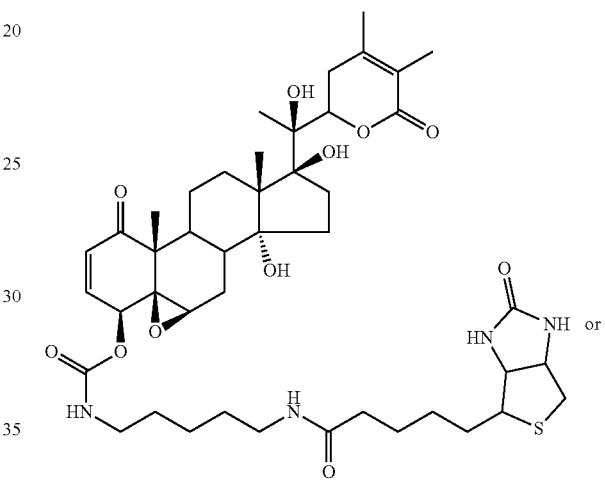

or

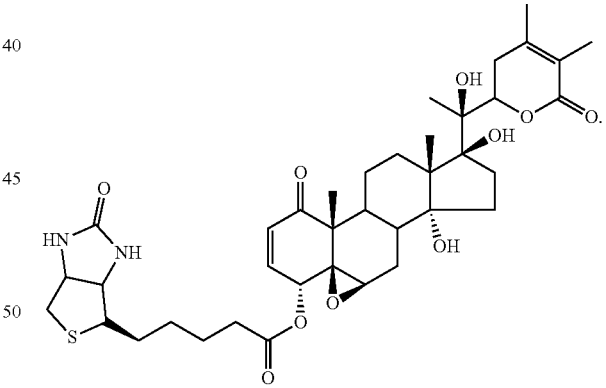

In accordance with a specific embodiment of the invention, $R^3$ and $R^4$, taken together, form a double bond.

In accordance with a specific embodiment of the invention, $R^5$ is H.

In accordance with a specific embodiment of the invention, $R^7$ and $R^9$ are $CH_3$ and $R^8$ and $R^{10}$, taken together, form a double bond.

In accordance with a specific embodiment of the invention, $R^1$ and $R^2$, taken together, form =O.

In accordance with the above embodiments, the compound is of the formula:

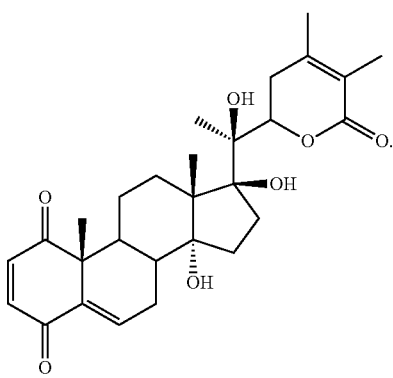 [SMILES: CC1=C(C)C(=O)OC([C@](C)(O)[C@]2(O)CC[C@@]3(O)C4CC=C5C(=O)C=CC(=O)[C@]5(C)C4CC[C@]23C)C1]

As used herein, the term "synergistic" refers to a combination of compounds of the invention and/or a combination of a compound or compounds of the invention and another therapy (e.g., a prophylactic or therapeutic agent), including one which has been or is currently being used to prevent, manage or treat a disorder (e.g., a proliferative disorder or cancer), which combination is more effective than the additive effects of the individual compounds or therapies. A synergistic effect of a combination of therapies (e.g., a combination of prophylactic or therapeutic agents) can permit the use of lower dosages of one or more of the therapies and/or less frequent administration of the therapies to a subject with a disorder (e.g., a proliferative disorder or cancer). The ability to utilize lower dosages of a therapy (e.g., a prophylactic or therapeutic agent) and/or to administer the therapy less frequently can reduce the toxicity associated with the administration of the therapy to a subject without reducing the efficacy of the therapy in the prevention, management or treatment of a disorder (e.g., a proliferative disorder or cancer). ID addition, a synergistic effect can result in improved efficacy of agents in the prevention, management or treatment of a disorder (e.g., a proliferative disorder or cancer). Moreover, a synergistic effect of a combination of therapies (e.g., a combination of prophylactic or therapeutic agents) can avoid or reduce adverse or unwanted side effects associated with the use of either therapy alone.

The term "synergistic" is contrasted with the term "additive" in that a combination of an agent having an additive effect and an apoptosis inducing ligand exhibits an effect that is simply the sum of the effect produced by the agent and the apoptosis inducing ligand when administered individually.

As used herein, the term "apoptosis inducing ligand" refers more specifically to a "apoptosis inducing receptor agonist" and is intended to mean an agent capable of stimulating by direct or indirect contact the proapoptotic response mediated by the apoptosis inducing receptors. In certain embodiments, the apoptosis inducing receptor is a cytokine receptor, for example, a TNF receptor. In an embodiment, the apoptosis inducing ligand is TRAIL. TRAIL itself binds to DR4 and DR5. An agonist TRAIL receptor antibody would bind to TRAIL receptor and trigger an apoptotic response. In embodiments, the apoptosis inducing ligand is selected from the group consisting of TRAIL, TNF-α, FasL, an anti-DR4 antibody, and an anti-DR5 antibody.

TRAIL (also referred to as ApoL2) is tumor necrosis factor-α-related apoptosis-inducing ligand and is a widely expressed member of the tumor necrosis factor (TNF) superfamily. TRAIL ligand exists in two forms: as a type II membrane protein expressed on the surface of certain lymphoid cells, and as a cleaved, soluble protein that is detectable in serum. For the purposes of the present invention, soluble recombinant TRAIL is suitable for use and is available from several vendors such as Peprotech, Inc. (Rocky Hill, N.J.). The percent growth reduction in treated cells is thought to be the result of apoptosis induced by the death receptor ligand.

Agonist antibodies directed against the death receptors TRAIL-R1 and/or TRAIL-R2 also can be used in conjunction with the method of the present invention. Exemplary agonist antibodies that may be used in combination with the method of the present invention include those described in U.S. Pat. No. 7,244,429; in U.S. Patent Application Publication Nos. 2007/0179086, 2002/0004227, 2006/0269554, 2005/0079172, 2007/0292411, 2006/0270837, 2006/0269555, 2004/0214235, and 2007/0298039; and in International Patent Publications WO2006/017961 and WO98/51793. Each of these publications is hereby incorporated by reference in its entirety. In addition, anti-DR4 and anti-DR5 antibodies are commercially available from Sigma Aldrich (St. Louis, Mo.) and Enzo Life Sciences (Farmingdale, N.Y.). In preferred embodiments, compounds of the invention are used in combination with one or more of these TRAIL receptor agonist antibodies for the treatment of cancer and other neoplasms.

Examples of suitable antibodies include purified soluble monoclonal antibody which specifically binds TRAIL receptor DR5, wherein the antibody has in vitro cell death-inducing activity in the absence of crosslinking by a secondary antibody and at concentrations less than 1 micromol.g/ml in target cells expressing DR5, and wherein the antibody has in vivo cell death-inducing activity in target cells expressing DR5, and wherein the antibody does not bind TRAIL receptor DR4, DcR1, or DcR2.

In certain embodiments, the apoptosis inducing receptor is a toll-like receptor ("TLR"). TLRs are a class of proteins that play a key role in the innate immune system. The TLRs include TLR1, TLR2, TLR3, TLR4, TLR5, TLR6, TLR7, TLR8, TLR9, TLR10, TLR11, TLR12, and TLR13, although TLR11, TLR12, and TLR13 are not found in humans. In these embodiments, the apoptosis inducing ligand is a TLR ligand. In a preferred embodiment, the TLR ligand is a ligand for TLR3. Non-limiting examples of suitable TLR ligands include double stranded RNA, polyinosine-polycytidylic acid ("poly IC"), mRNA, and tRNA. In a preferred embodiment, the TLR ligand is poly IC. Poly IC is a synthetic mismatched double-stranded RNA with one strand being a polymer of inosinic acid and the other a polymer of cytidylic acid being annealed to each other. Poly IC is available in a range of chain lengths and molecular weights. Poly IC is commercially available from InvivoGen (San Diego, Calif.).

In certain embodiments, the method of synergistically enhancing the response of cancer cells in a mammal to treatment with an apoptosis-inducing ligand or of inducing apoptosis in cancer cells in a mammal that are resistant to treatment with an apoptosis-inducing ligand further comprises administering to the mammal an Smac mimetic, a Blc-2 antagonist, or a combination thereof. The Smac mimetic or Blc-2 antagonist can be any suitable Smac mimetic or Blc-2 antagonist. In certain embodiments, the Smac mimetic is birinapant, GDC-015, or LCL-161. In certain embodiments, the Blc-2 antagonist is ABT-199, ABT-737, or venetoclax.

Desirably, the combination of a compound of the invention and Smac mimetic and/or Blc-2 antagonist exhibits a synergistic effect in sentization of cancer cells to treatment with the apoptosis-inducing ligand or to induction of apoptosis when the cancer cells are resistant to treatment with the apoptosis-inducing ligand, as compared to treatment with a compound of the invention Smac mimetic and/or Blc-2 antagonist.

Any method known in the art can be used to measure the enhancement of the response to cancer cells to treatment with an apoptosis-inducing ligand. In addition, any known method known in the art can be used to determine the induction of apoptosis. The Examples section of the present specification describes exemplary methods. For example, the growth inhibition of cancer cells can be determined by measurement of the decrease in cell viability by use of the tetrazolium/formazan assay ("XTT assay") as described in Scudiero et al., Cancer Res. 48 (17): 4827-4833 (1988), or by use of the sulphorhodamine B protein staining assay ("SRB protein stain") as described in Skehan et al., J. Natl. Cancer Inst. 82 (13): 1107-1112 (1990) or in Vichai et al., Nat. Protoc 1 (3): 1112-1116. Another suitable assay for the growth inhibition of cancer cells is the MTS cell proliferation colorimetric assay. The MTS method is based on the reduction of MTS tetrazolium compound by viable cells to generate a colored formazan product that is soluble in cell culture media. This conversion is thought to be carried out by NAD(P)H-dependent dehydrogenase enzymes in metabolically active cells. The formazan dye produced by viable cells can be quantified by measuring the absorbance at 490-500 nm.

The cancer cells in a human can be contacted with an apoptosis-inducing ligand in conjunction with a sensitizer by administering to the human a formulation containing an effective amount of the sensitizer and a formulation containing the apoptosis-inducing ligand. In some embodiments, the sensitizer can be present in the same formulation as the apoptosis-inducing ligand so that the administration can be simultaneous. Any of the sensitizers of the invention can be used in combination with an apoptosis-inducing ligand, e.g., simultaneously, sequentially, e.g., before or after the apoptosis-inducing ligand, or cyclically. In some embodiments, it is suitable to administer two or more separate and distinct formulations, one of which contains the sensitizer and the other contains the apoptosis-inducing ligand. The separate and distinct formulations can be administered simultaneously, or the formulations can be administered separately at different time periods. For example, in preferred embodiments, the formulation containing the sensitizer can be administered about 1 hour (e.g., about 2 hours, or about 3 hours, or about 4 hours, or about 8 hours, or about 24 hours) prior to administration of the formulation containing the apoptosis-inducing ligand. In preferred embodiments, the apoptosis-inducing ligand is administered parenterally in the form of a suitable parenteral formulation, while the sensitizer can be administered in the form of any suitable formulation. Suitable formulations include oral, aerosol, nasal, pulmonary, parenteral, subcutaneous, intravenous, intramuscular, intraperitoneal, intrathecal, intratumoral, topical, rectal, and vaginal formulations.

The pharmaceutical composition can be administered parenterally, e.g., intravenously, subcutaneously, intradermally, or intramuscularly. Thus, the invention provides compositions for parenteral administration that comprise a solution or suspension of the sensitizer and/or the apoptosis-inducing ligand dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, e.g., Banker and Chalmers, eds., *Pharmaceutics and Pharmacy Practice*, J. B. Lippincott Company, Philadelphia, pp. 238-250 (1982), and Toissel, *ASHP Handbook on Injectable Drugs*, $4^{th}$ ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The sensitizer and/or apoptosis-inducing ligand may be administered in physiologically acceptable ampoules in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one sensitizer and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Formulations suitable for oral administration can consist of (a) liquid solutions, such as a therapeutically effective amount of the sensitizer dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The sensitizer, alone or in combination with other suitable components, can be made into aerosol formulations to be administered via inhalation. The compounds are preferably supplied in finely divided form along with a surfactant and propellant. Typical percentages of a sensitizer are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the sensitizer may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the sensitizer, such carriers as are known in the art to be appropriate.

It will be appreciated by one of ordinary skill in the art that, in addition to the aforedescribed pharmaceutical compositions, the sensitizer may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the sensitizer. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired sensitizer can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.*, 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

"Treating" within the context of the present invention, means an alleviation of symptoms associated with a disorder or disease, or halt of further progression or worsening of those symptoms, or prevention or prophylaxis of the disease or disorder. For example, within the context of treating patients with renal cancer, successful treatment may include a reduction in the proliferation of capillaries feeding the diseased tissue, an alleviation of symptoms related to a cancerous growth or tumor, or a halting in the progression of a disease such as cancer or in the growth of cancerous cells. Treatment may also include administering the pharmaceutical formulations of the present invention in combination with other therapies. For example, the sensitizer and apoptosis-inducing ligand may be administered before, during, or after surgical procedure and/or radiation therapy. The sensitizer and apoptosis-inducing ligand can also be administered in conjunction with other anti-cancer drugs and drugs used in antisense and gene therapy. Appropriate combinations can be determined by those of skill in the oncological and medical arts.

"Preventing" within the context of the present invention, refers to a prophylactic treatment of an individual prone or subject to development of a cancer. For example, those of skill in the oncological and medical arts may be able to determine, based on clinical symptoms and patient history, a statistical predisposition of a particular individual to the development of the cancer. Accordingly, an individual predisposed to the development of a cancer may be treated with a sensitizer and apoptosis-inducing ligand in order to prevent, inhibit, or slow the development of the disease or disorder.

One skilled in the art will appreciate that suitable methods of utilizing a sensitizer and an apoptosis-inducing ligand and administering the sensitizer and an apoptosis-inducing ligand to a human for the treatment or prevention of disease states, in particular, cancers responsive to treatment with apoptosis-inducing ligands (e.g., renal cancers and melanomas) which would be useful in the method of the present invention, are available. Although more than one route can be used to administer the sensitizer and an apoptosis-inducing ligand, particular route can provide a more immediate and more effective reaction than another route. Accordingly, the described methods are merely exemplary and are in no way limiting.

The dose of the sensitizer and the dose of the apoptosis-inducing ligand administered to a mammal, particularly, a human, in accordance with the present invention should be sufficient to effect the desired response. Such responses include reversal or prevention of the bad effects of the disease for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the dose of the sensitizer and the dose of the apoptosis-inducing ligand will also be determined by the route, timing and frequency of administration as well as the existence, nature, and extent of any adverse side-effects that might accompany the administration of the dose of the sensitizer and the dose of the apoptosis-inducing ligand and the desired physiological effect. It will be appreciated by one of skill in the art that various conditions or disease states may require prolonged treatment involving multiple administrations.

The term "mammal" includes, but is not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, Simioids (monkeys) or of the order Anthropoids (humans and apes). An especially preferred mammal is the human. Furthermore, the subject can be the unborn offspring of any of the forgoing hosts, especially mammals (e.g., humans), in which case any screening of the subject or cells of the subject, or administration of compounds to the subject or cells of the subject, can be performed in utero.

Suitable doses and dosage regimens can be determined by conventional range-finding techniques known to those of ordinary skill in the art. Generally, treatment is initiated with smaller dosages that are less than the optimum dose of the sensitizer and/or the apoptosis-inducing ligand. Thereafter, the dosage is increased by small increments until the optimum effect under the circumstances is reached. The present inventive method typically will involve the administration of about 0.01 to about 10 mg, in certain embodiments about 0.1 mg to about 5 mg, and in other embodiments 0.1 mg to about 2 mg, of one or more of the sensitizers and about 0.1 to about 300 mg of the apoptosis inducing ligand described above, per kg body weight of the mammal.

In any of the embodiments of the invention, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, skin carcinoma, melanoma, basal cell carcinoma, squamous cell carcinoma, anaplastic large-cell lymphoma, multiple myeloma, leukemia, lymphoma, cervical carcinoma, and mesothelioma, and combinations thereof. The cancer can be any suitable cancer, for example, follicular thyroid carcinoma, colorectal cancer, pancreatic cancer, leukemias, such as myeloid leukemia, prostate cancer, hepatic cancer, hepatocellular carcinoma, cholangiocarcinoma, cervical and ovarian cancer, cancers of glial origin and renal cancer. As is known in the art, carcinoma generally is a term for cancers that originate in epithelial tissues. Sarcomas originate in mesenchymal tissues and leukemias and lymphomas are blood cancers. As used herein, cancers include carcinomas, sarcomas and leukemias/lymphomas.

In accordance with an embodiment, the methods can be applied to treat patients who are immune compromised, e.g., those who have a reduced p53 function.

The invention further provides a compound of the formula:

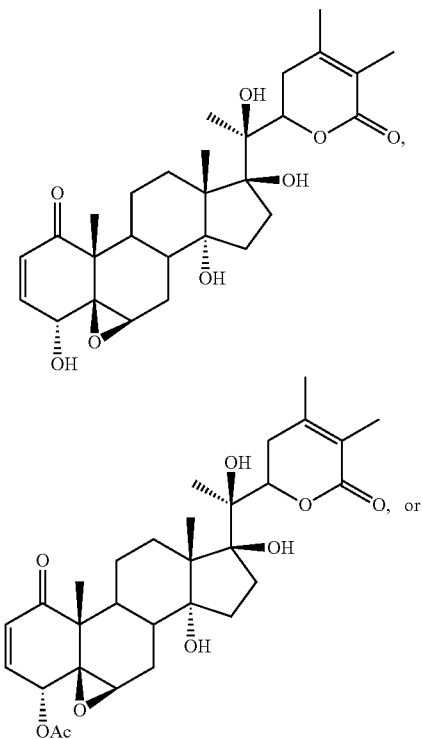

-continued

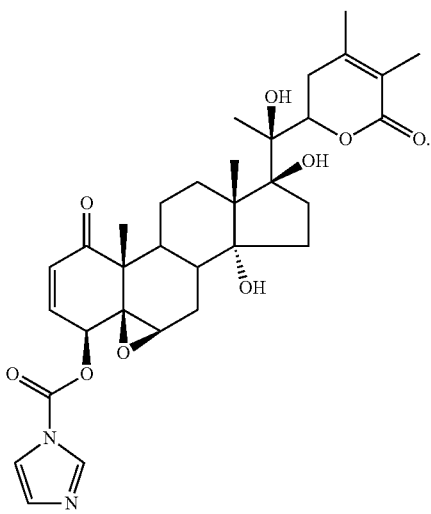

The invention additionally provides a compound of the formula:

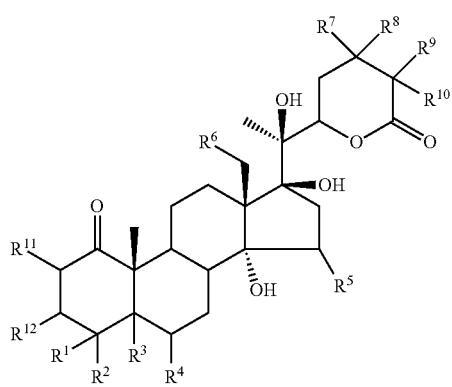

wherein $R^1$ and $R^2$ are independently selected from H and a group of the formula:

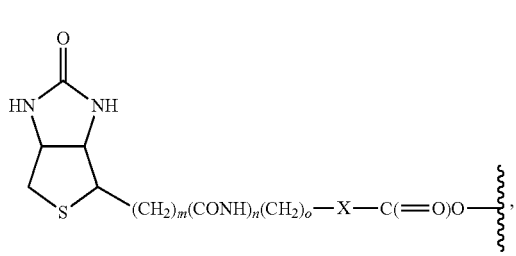

X is NH or is absent, m and o are integers of from 1 to about 10, n is 0 or 1, $R^3$ and $R^4$ are independently OH or $C_1$-$C_6$ alkoxy or, taken together, form a double bond or an epoxy ring, $R^5$ is H or $C_1$-$C_6$ acyloxy, $R^6$ is H, OH, or $C_1$-$C_6$ acyloxy, or $R^7$ and $R^9$ are independently $CH_2OH$ or

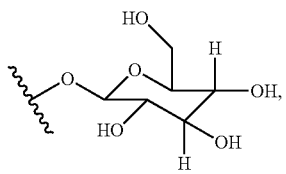 [SMILES: *OC1OC(CO)C(O)C(O)C1O]

$R^8$ and $R^{10}$, taken together with the carbon atoms to which they are attached, form a double bond or an epoxy ring, and $R^{11}$ and $R^{12}$ are both H, $R^{11}$ is H and $R^{12}$ is —$OSO_3H$, $R^{11}$ is H and $R^{12}$ is imidazolyl, or $R^{11}$ and $R^{12}$, taken together with the carbon atoms to which they are attached, form a double bond.

In accordance with an embodiment of the invention, $R^{11}$ and $R^{12}$, taken together, form a double bond.

In accordance with an embodiment of the invention, $R^3$ and $R^4$, taken together, form an epoxy ring.

In accordance with an embodiment of the invention, $R^5$ is H.

In accordance with an embodiment of the invention, $R^7$ and $R^9$ are $CH_3$ and $R^8$ and $R^{10}$, taken together, form a double bond. In certain of these embodiments, $R^1$ is H and $R^2$ is a group of the formula:

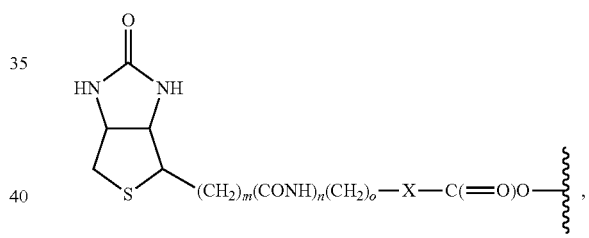

m and o are integers of from 1 to about 10, and n is 0 or 1.

In particular embodiments, the compound is of the formula:

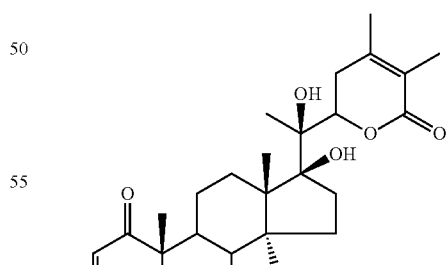
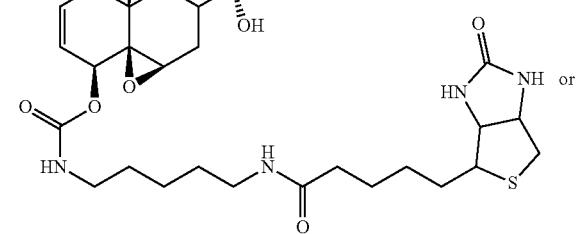

-continued

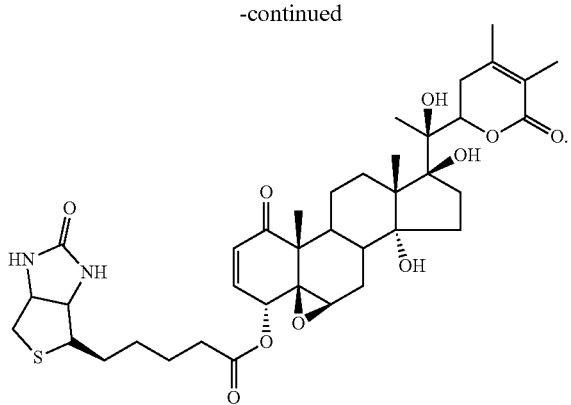

The invention is exemplified by the following embodiments:

1. A method of synergistically enhancing the response of cancer cells in a mammal to treatment with an apoptosis-inducing ligand, which method comprises administering to the mammal an effective amount of a compound of the formula:

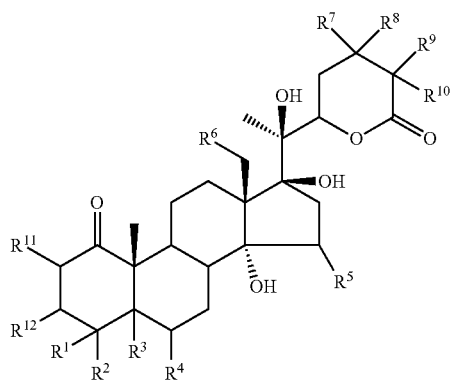

wherein $R^1$ and $R^2$ are independently selected from H, OH, $C_1$-$C_6$ acyloxy, $C_1$-$C_6$ alkylcarbonate, heteroarylcarbonyloxy, a group of the formula:

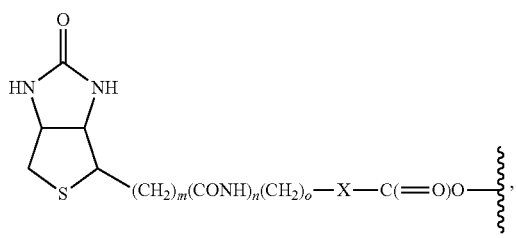

or, $R^1$ and $R^2$ taken together, form =O,
X is NH or is absent,
m and o are integers of from 1 to about 10,
n is 0 or 1,
$R^3$ and $R^4$ are independently OH or $C_1$-$C_6$ alkoxy or, taken together, form a double bond or an epoxy ring,
$R^5$ is H or $C_1$-$C_6$ acyloxy,
$R^6$ is H, OH, or $C_1$-$C_6$ acyloxy, or
$R^7$ and $R^9$ are independently $CH_2OH$ or

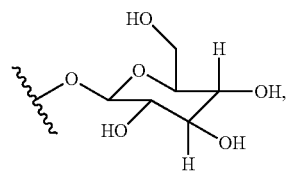 [SMILES: *OC1OC(CO)C(O)C(O)C1O]

$R^8$ and $R^{10}$, taken together with the carbon atoms to which they are attached, form a double bond or an epoxy ring, and $R^{11}$ and $R^{12}$ are both H, $R^{11}$ is H and $R^{12}$ is —$OSO_3H$, $R^{11}$ is H and $R^{12}$ is imidazolyl, or $R^{11}$ and $R^{12}$, taken together with the carbon atoms to which they are attached, form a double bond, and administering an effective amount of an apoptosis-inducing ligand, whereby a synergistic enhancement of the response is obtained.

2. The method of embodiment 1, wherein $R^{11}$ and $R^{12}$, taken together, form a double bond.

3. The method of embodiment 1 or 2, wherein $R^3$ and $R^4$, taken together, form an epoxy ring.

4. The method of any one of embodiments 1-3, wherein $R^5$ is H.

5. The method of any one of embodiments 1-4, wherein $R^7$ and $R^9$ are $CH_3$ and wherein $R^8$ and $R^{10}$, taken together, form a double bond.

6. The method of any one embodiments 1-5, wherein $R^1$ and $R^2$ are H.

7. The method of embodiment 6, wherein the compound is of the formula:

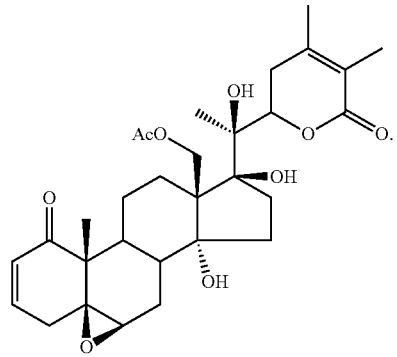 [SMILES: CC(=O)OC[C@]12CCC3C(C[C@H]4O[C@]45CC=CC(=O)[C@]35C)[C@]1(O)CC[C@@]2(O)[C@@](C)(O)C1CC(C)=C(C)C(=O)O1]

8. The method of any one of embodiment 1-5, wherein $R^1$ is H and $R^2$ is OH.

9. The method of embodiment 8, wherein $R^6$ is H.

10. The method of embodiment 9, wherein the compound is of the formula:

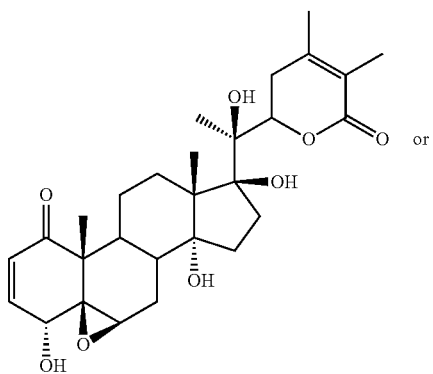

or

-continued

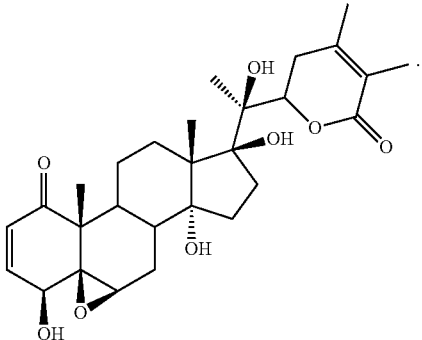

11. The method of any one of embodiments 1-5, wherein $R^1$ is H and $R^2$ is $C_1$-$C_6$ acyloxy.

12. The method of embodiment 11, wherein the compound is of the formula:

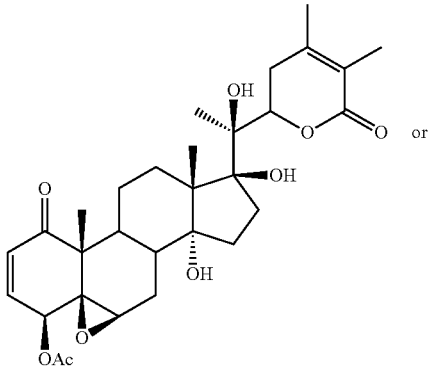

or

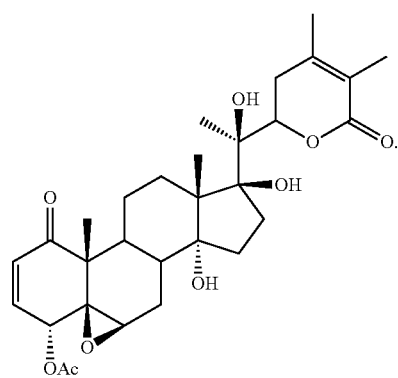

13. The method of any one of embodiments 1-5, wherein $R^1$ is H and $R^2$ is heteroarylcarbonyloxy.

14. The method of embodiment 13, wherein the compound is of the formula:

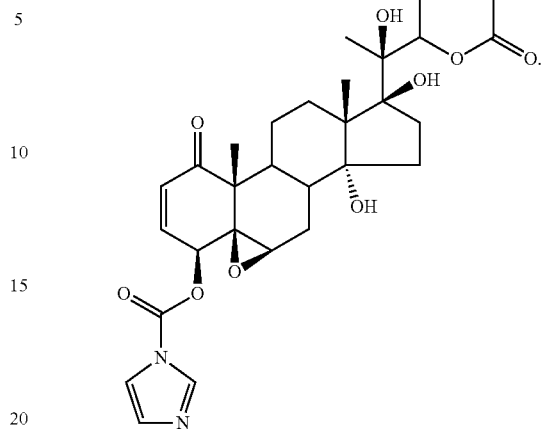

15. The method of any one of embodiments 1-5, wherein $R^1$ is H and $R^2$ is a group of the formula:

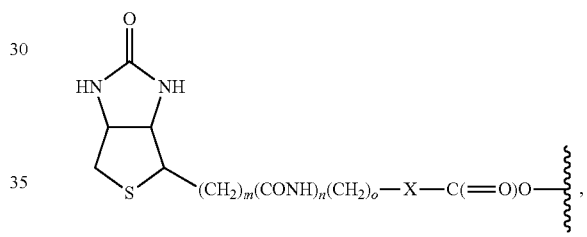

m and o are integers of from 1 to about 10, and
n is 0 or 1.

16. The method of embodiment 15, wherein the compound is of the formula:

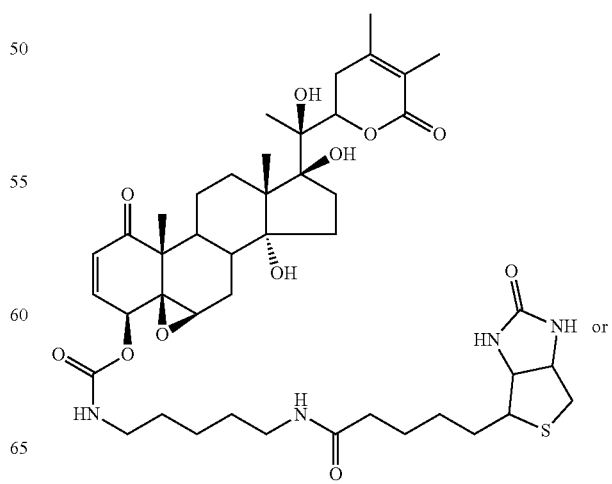

or

-continued

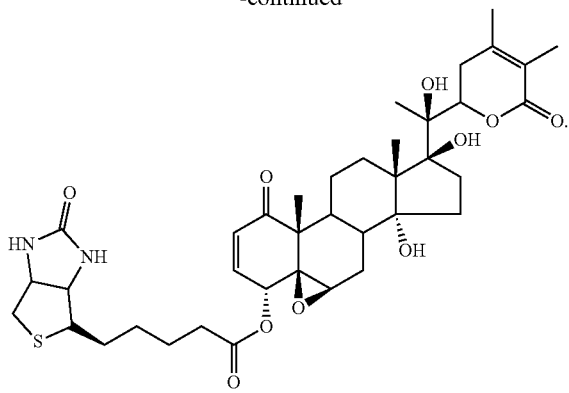

17. The method of embodiment 1 or 2, wherein $R^3$ and $R^4$, taken together, form a double bond.
18. The method of embodiment 17, wherein $R^5$ is H.
19. The method of embodiment 17 or 18, wherein $R^7$ and $R^9$ are $CH_3$ and wherein $R^8$ and $R^{10}$, taken together, form a double bond.
20. The method of any one of embodiments 17-19, wherein $R^1$ and $R^2$, taken together, form =O.
21. The method of embodiment 20, wherein the compound is of the formula:

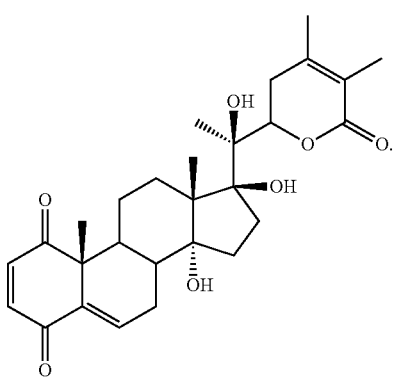 [SMILES: CC1=C(C)C(=O)OC([C@](C)(O)[C@]2(O)CC[C@@]3(O)C4CC=C5C(=O)C=CC(=O)[C@]5(C)C4CC[C@]23C)C1]

22. The method of any one of embodiments 1-21, wherein the cancer cells express a TNF receptor or a toll-like receptor.
23. The method of any one of embodiments 1-22, wherein the apoptosis-inducing ligand is selected from the group consisting of TRAIL, TNF-α, FasL, an anti-DR4 antibody, and an anti-DR5 antibody.
24. The method of embodiment 23, wherein the apoptosis-inducing ligand is poly IC.
25. The method of any one of embodiments 1-22, further comprising administering to the mammal an Smac mimetic, a Bcl-2 antagonist, or a combination thereof.
26. The method of embodiment 25, wherein the Smac mimetic is birinapant, GDC-015, or LCL-161.
27. The method of embodiment 25, wherein the Bcl-2 antagonist is ABT-199, ABT-737, or venetoclax.
28. The method of any one of embodiments 1-27, wherein the cancer cells are associated with a cancer selected from glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, skin carcinoma, melanoma, basal cell carcinoma, squamous cell carcinoma, anaplastic large-cell lymphoma, multiple myeloma, leukemia, lymphoma, cervical carcinoma, and mesothelioma, follicular thyroid carcinoma, colorectal cancer, myeloid leukemia, hepatic cancer, hepatocellular carcinoma, cholangiocarcinoma, cervical and ovarian cancer, cancers of glial origin, and combinations thereof.

29. The method of embodiment 1, wherein the compound is of the formula:

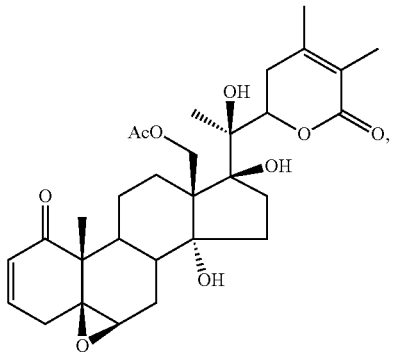

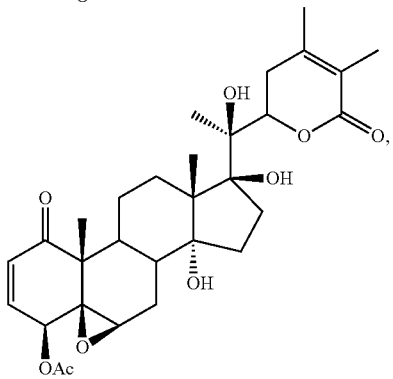

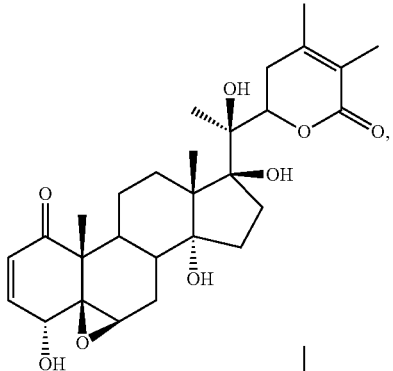

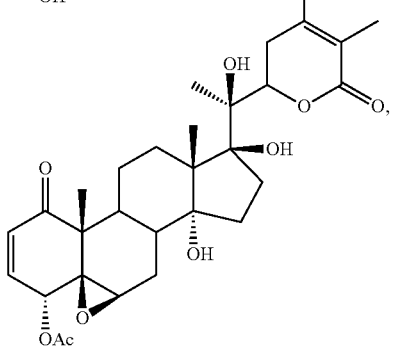

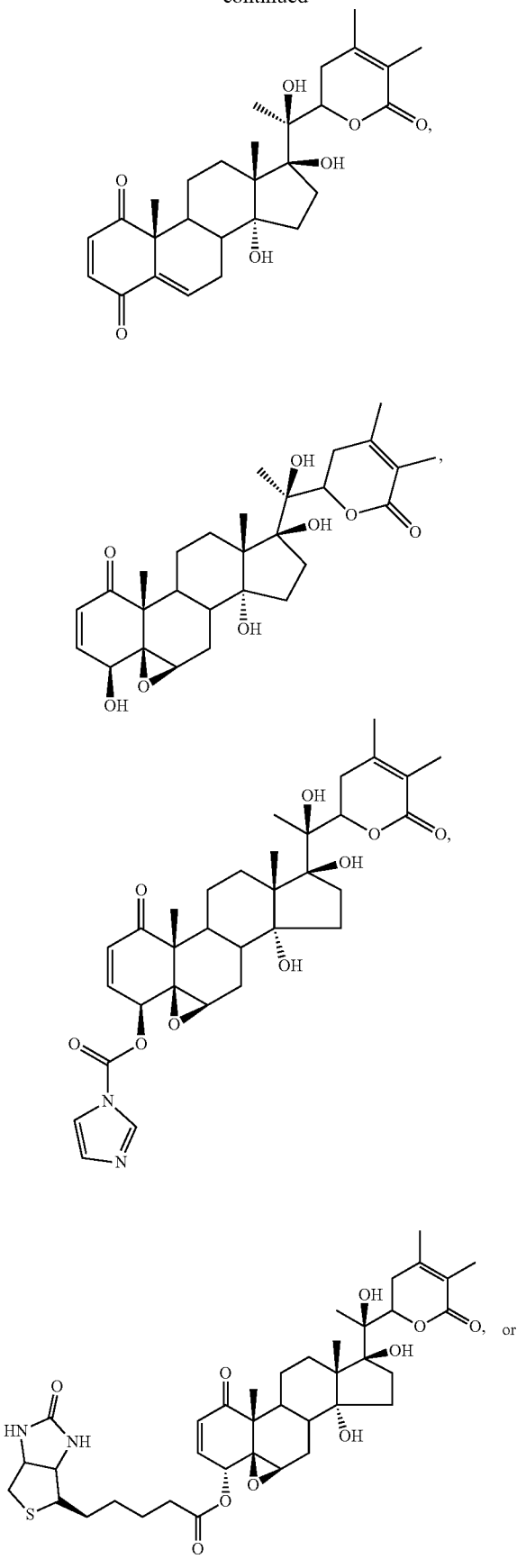

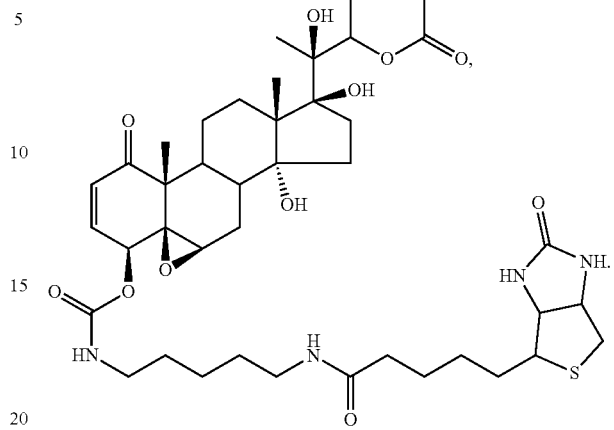

30. A method of inducing apoptosis in cancer cells in a mammal that are resistant to treatment with an apoptosis-inducing ligand, which method comprises administering to the mammal an effective amount of a compound of the formula:

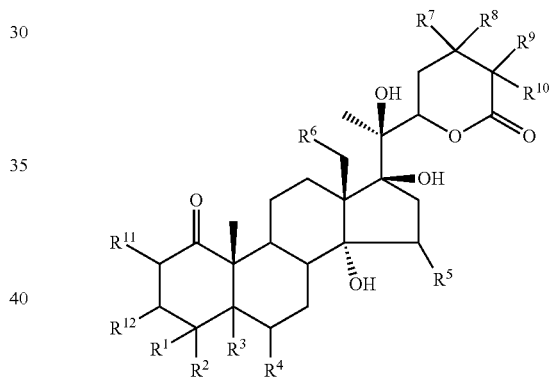

wherein $R^1$ and $R^2$ are independently selected from H, OH, $C_1$-$C_6$ acyloxy, $C_1$-$C_6$ alkylcarbonate, heteroarylcarbonyloxy, a group of the formula:

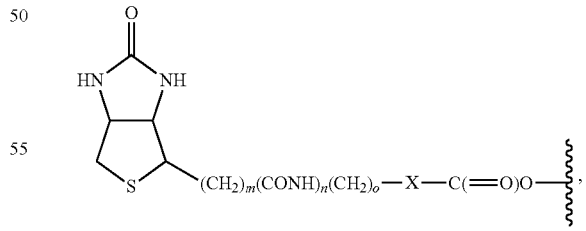

or, $R^1$ and $R^2$ taken together, form =O,
X is NH or is absent,
m and o are integers of from 1 to about 10,
n is 0 or 1,
$R^3$ and $R^4$ are independently OH or $C_1$-$C_6$ alkoxy or, taken together, form a double bond or an epoxy ring,
$R^5$ is H or $C_1$-$C_6$ acyloxy,
$R^6$ is H, OH, or $C_1$-$C_6$ acyloxy, or $R^7$ and $R^9$ are independently $CH_2OH$ or

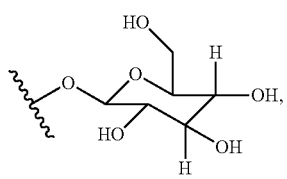

$R^8$ and $R^{10}$, taken together with the carbon atoms to which they are attached, form a double bond or an epoxy ring, and $R^{11}$ and $R^{12}$ are both H, $R^{11}$ is H and $R^{12}$ is —$OSO_3H$, $R^{11}$ is H and $R^{12}$ imidazolyl, or $R^{11}$ and $R^{12}$, taken together with the carbon atoms to which they are attached, form a double bond, and administering an effective amount of an apoptosis-inducing ligand, whereby a synergistic enhancement of the response is obtained.

31. The method of embodiment 30, wherein $R^{11}$ and $R^{12}$, taken together, form a double bond.

32. The method of embodiment 30 or 31 wherein $R^3$ and $R^4$, taken together, form an epoxy ring.

33. The method of any one of embodiments 30-32, wherein $R^5$ is H.

34. The method of any one of embodiments 30-33, wherein $R^7$ and $R^9$ are $CH_3$ and wherein $R^8$ and $R^{10}$, taken together, form a double bond.

35. The method of any one of embodiments 30-34, wherein $R^1$ and $R^2$ are H.

36. The method of embodiment 35, wherein the compound is of the formula:

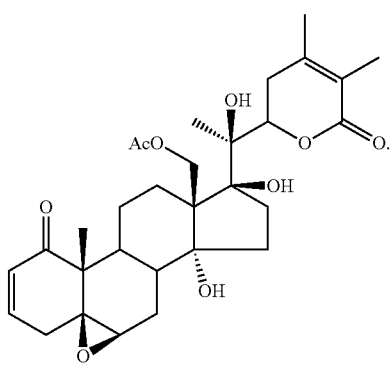 [SMILES: CC(=O)OC[C@]12CCC3C(C[C@H]4O[C@]45CC=CC(=O)[C@]35C)[C@]1(O)CC[C@@]2(O)[C@@](C)(O)C1CC(C)=C(C)C(=O)O1]

37. The method of any one of embodiments 30-34, wherein $R^1$ is H and $R^2$ is OH.

38. The method of embodiment 37, wherein $R^6$ is H.

39. The method of embodiment 38, wherein the compound is of the formula:

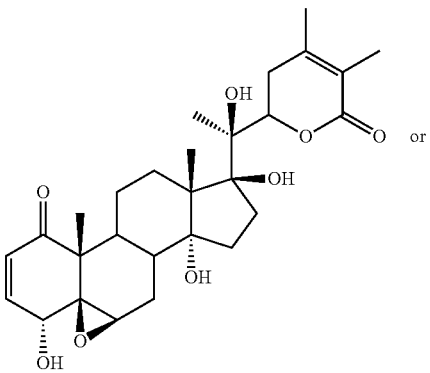

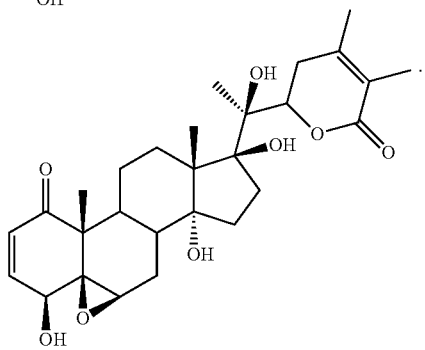

40. The method of any one of embodiments 30-34, wherein $R^1$ is H and $R^2$ is $C_1$-$C_6$ acyloxy.

41. The method of embodiment 40, wherein the compound is of the formula:

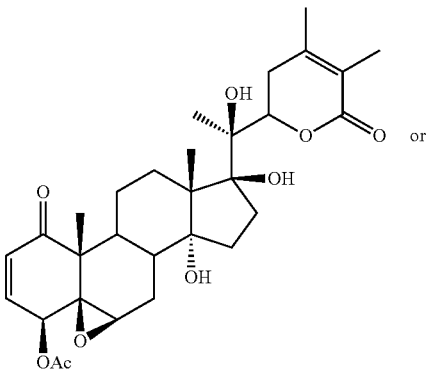

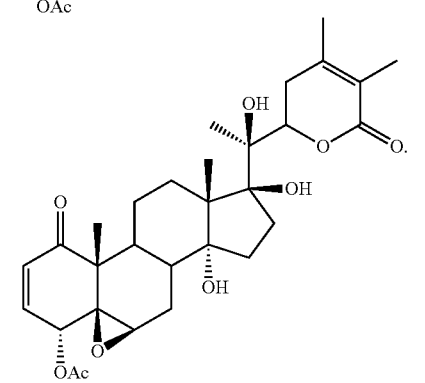

42. The method of any one of embodiments 30-34, wherein $R^1$ is H and $R^2$ is heteroarylcarbonyloxy.

43. The method of embodiment 42, wherein the compound is of the formula:

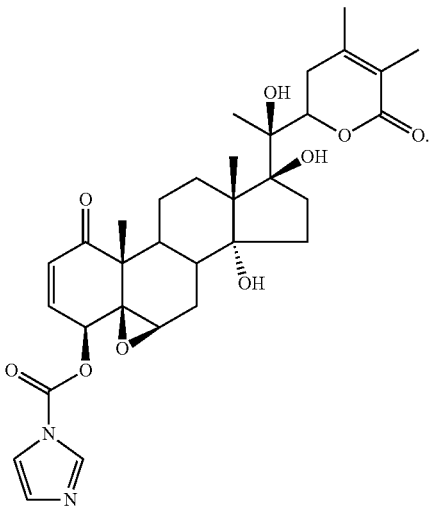 [SMILES: CC1=C(C)C(=O)OC([C@](C)(O)[C@]2(O)CC[C@@]3(O)C4C[C@H]5O[C@]56[C@@H](OC(=O)n5ccnc5)C=CC(=O)[C@]6(C)C4CC[C@]23C)C1]

44. The method of any one of embodiments 30-34, wherein $R^1$ is H and $R^2$ is a group of the formula:

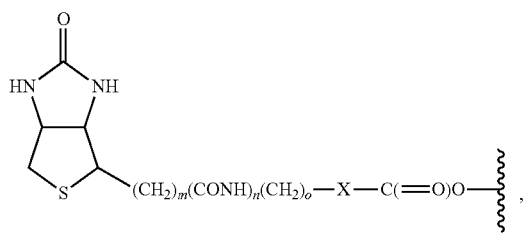

m and o are integers of from 1 to about 10, and n is 0 or 1.

45. The method of embodiment 44, wherein the compound is of the formula:

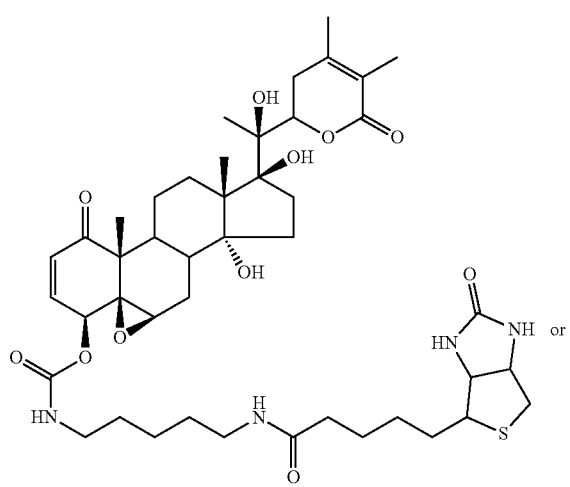

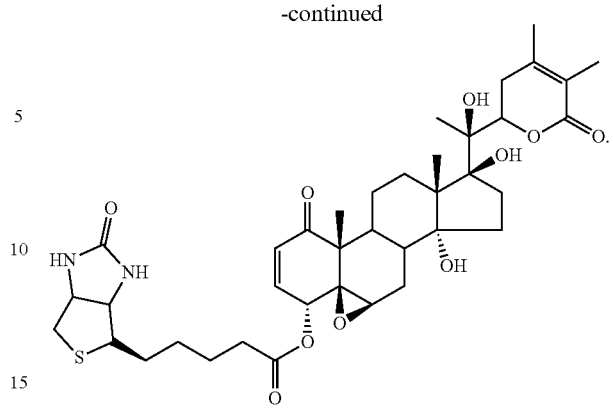

46. The method of embodiment 30 or 31, wherein $R^3$ and $R^4$, taken together, form a double bond.

47. The method of embodiment 46, wherein $R^5$ is H.

48. The method of embodiment 46 or 47, wherein $R^7$ and $R^9$ are $CH_3$ and wherein $R^8$ and $R^{10}$, taken together, form a double bond.

49. The method of any one of embodiments 46-48, wherein $R^1$ and $R^2$, taken together, form =O.

50. The method of embodiment 49, wherein the compound is of the formula:

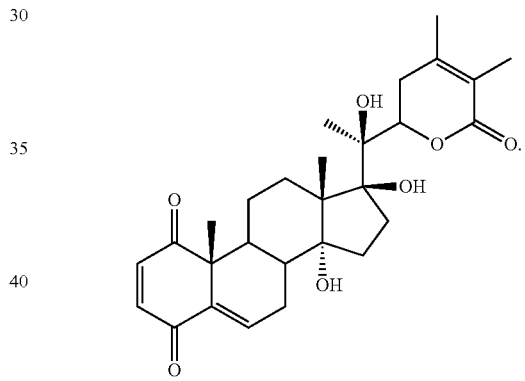

51. The method of any one of embodiments 30-50, wherein the cancer cells express a TNF receptor or a toll-like receptor.

52. The method of any one of embodiments 30-51, wherein the apoptosis-inducing ligand is selected from the group consisting of TRAIL, TNF-α, FasL, an anti-DR4 antibody, and an anti-DR5 antibody.

53. The method of embodiment 52, wherein the apoptosis-inducing hand is poly IC.

54. The method of any one of embodiments 30-53, further comprising administering to the mammal an Smac mimetic, a Bcl-2 antagonist, or a combination thereof.

55. The method of embodiment 54, wherein the Smac mimetic is birinapant, GDC-015, or LCL-161.

56. The method of embodiment 54, wherein the Bcl-2 antagonist is ABT-199, ABT-737, or venetoclax.

57. The method of any one of embodiments 30-56, wherein the cancer cells are associated with a cancer selected from glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, skin carcinoma, melanoma, basal cell carcinoma, squamous cell carcinoma, anaplastic large-cell lymphoma, multiple myeloma, leukemia, lymphoma, cervical carcinoma, and mesothelioma, follicular thyroid carcinoma, colorectal cancer, myeloid leukemia, hepatic cancer, hepatocellular carcinoma, cholangiocarcinoma, cervical and ovarian cancer, cancers of glial origin, and combinations thereof.

58. The method of embodiment 57, wherein the compound is of the formula:

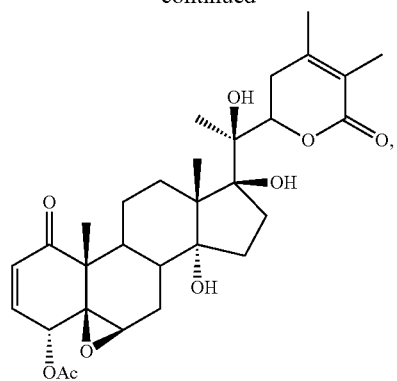

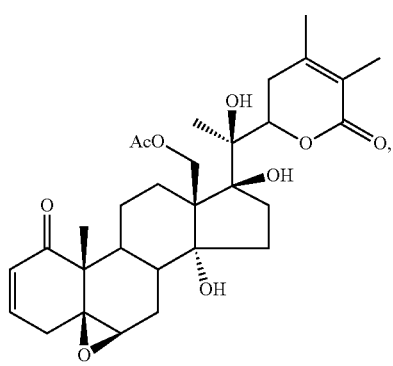

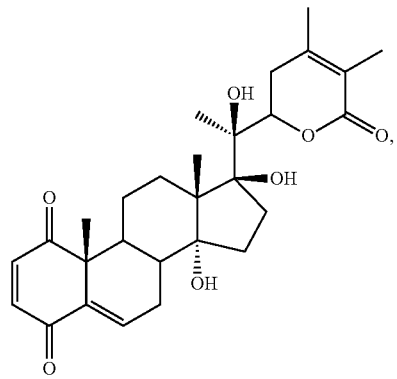

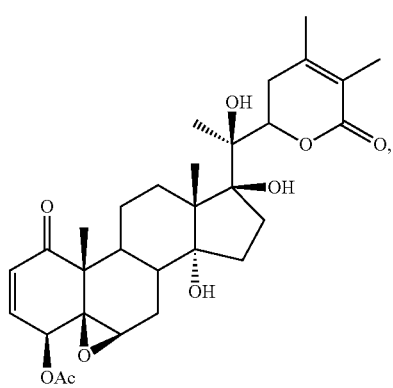

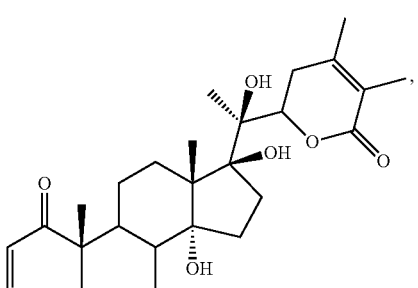

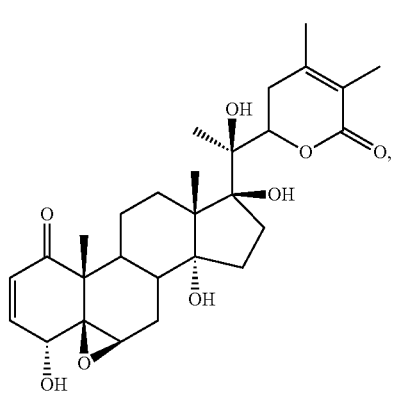

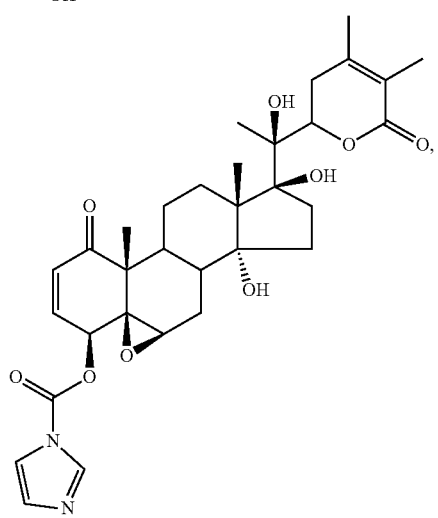

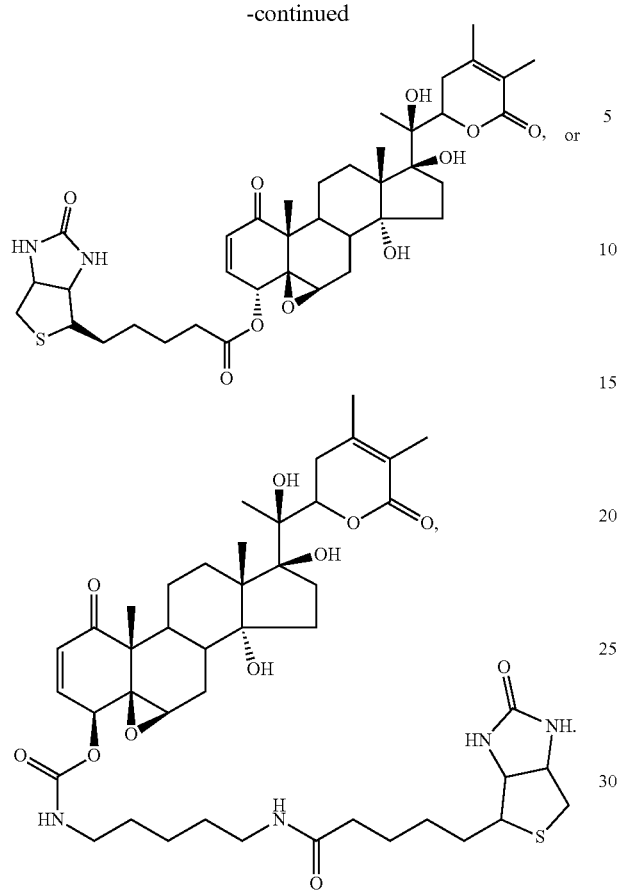

59. A compound of the formula:

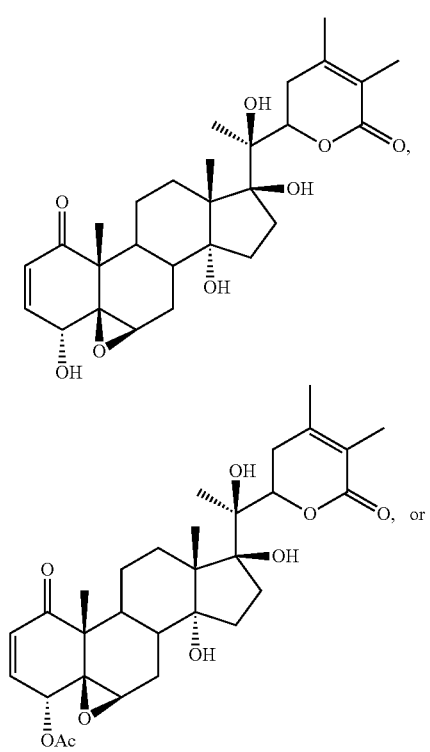

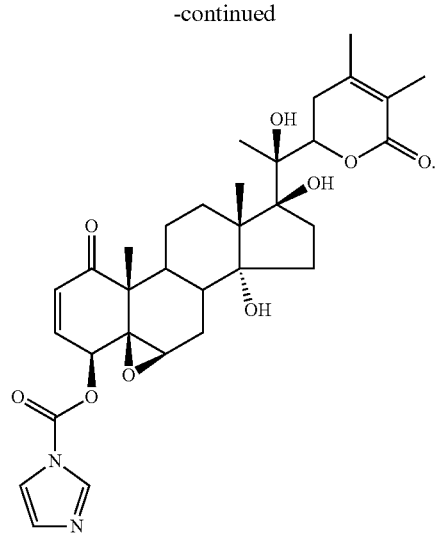

60. A compound of the formula:

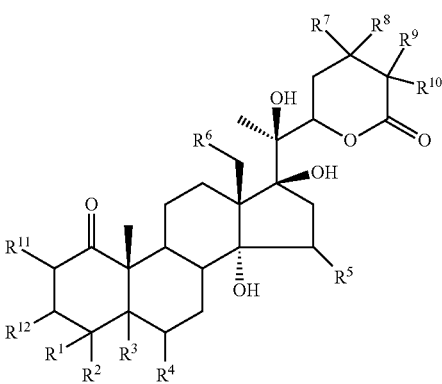

wherein $R^1$ and $R^2$ are independently selected from H and a group of the formula:

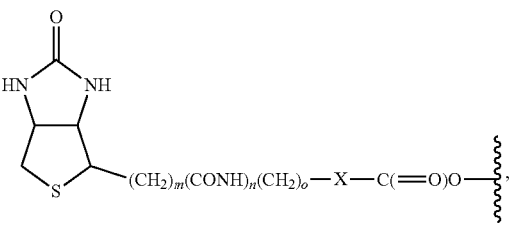

X is NH or is absent, m and o are integers of from 1 to about 10, n is 0 or 1, $R^3$ and $R^4$ are independently OH or $C_1$-$C_6$ alkoxy or, taken together, form a double bond or an epoxy ring, $R^5$ is H or $C_1$-$C_6$ acyloxy, $R^6$ is H, OH, or $C_1$-$C_6$ acyloxy, or $R^7$ and $R^9$ are independently $CH_2OH$ or

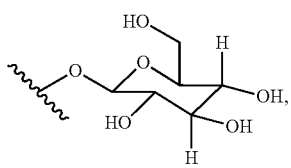 [SMILES: *OC1OC(CO)C(O)C(O)C1O]

$R^8$ and $R^{10}$, taken together with the carbon atoms to which they are attached, form a double bond or an epoxy ring, and $R^{11}$ and $R^{12}$ are both H, $R^{11}$ is H and $R^{12}$ is —OSO$_3$H, $R^{11}$ is H and $R^{12}$ is imidazolyl, or $R^{11}$ and $R^{12}$, taken together with the carbon atoms to which they are attached, form a double bond.

61. The compound of embodiment 60, wherein $R^{11}$ and $R^{12}$, taken together, form a double bond.

62. The compound of embodiment 60 or 61, wherein $R^3$ and $R^4$, taken together, form an epoxy ring.

63. The compound of any one of embodiments 60-62, wherein $R^5$ is H.

64. The compound of any one of embodiments 60-63, wherein $R^7$ and $R^9$ are CH$_3$ and wherein $R^8$ and $R^{10}$, taken together, form a double bond.

65. The compound of embodiments 60-64, wherein $R^1$ is H and $R^2$ is a group of the formula:

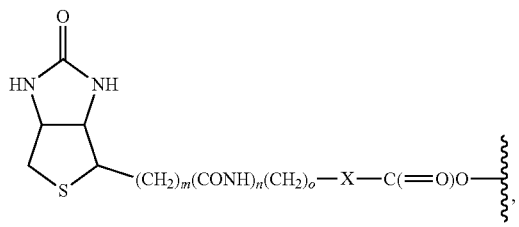

m and o are integers of from 1 to about 10, and n is 0 or 1.

66. The compound of embodiment 65, wherein the compound is of the formula:

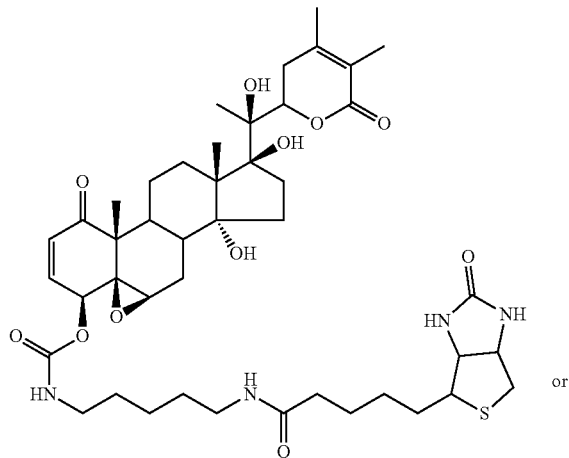

or

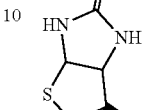
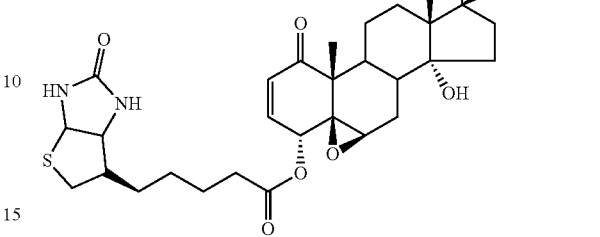

The following examples further illustrate the invention but, of course, should not be construed as in any way limiting its scope.

For all experiments, cells (ACHN (renal carcinoma), M14, SK MEL28, and Malme (human melanoma lines)) were plated at a concentration of 5000 cells/well overnight. All treatments were carried out the following day.

Female nude athymic mice were obtained from Charles River Laboratory. All mice were kept under specific pathogen-free conditions with water and food given ad libitum. All experiments with mice were performed in compliance with the principles and procedures outlined in the National Institutes of Health Guide for the Care and Use of Animals and were approved by the National Cancer Institute at Frederick Animal Care and Use Committee.

M14 melanoma line was maintained in Delbecco modified eagles medium {DMEM (Lonza)} supplemented with 10% Fetal Bovine serum {FBS (Hyclone)}, 2 mmol/L L-glutamine, 25 mmol/L HEPES, 100 U/mL penicillin, 100 μg/mL streptomycin, 1× vitamin solution and 1× nonessential amino acids solution (Lonza).

For in vivo treatments with compounds 9 and 1, compound 9 and compound 1 stock solutions (0.5M and 0.25M in DMSO respectively) were diluted in 33% Trappsol and DMSO at a ratio of 7:1 and administered intratumorally or at the base of tumor in a volume of 20 ul at a dose of 20 mg/Kg of body weight. For in vivo treatments with compound 9 and poly IC, compound 9 stock solution (0.5M) was diluted in 33% Trappsol and DMSO at a ratio of 7:1 and administered intratumorally or at the base of tumor in a volume of 20 ul at a dose of 20 mg/Kg of body weight. The following day poly IC (diluted in saline) (50 ug/mouse) was given intraperitoneally.

Example 1

This example demonstrates the percent growth inhibition of ACHN renal cancer cells in the presence of compounds 2, 3, 4, 5, 6, 7, 9, 1, and 10, respectively, at concentrations of 63 nM, 125 nM, 250 nM, and 500 nM, in the presence or absence of 10 μM poly IC, in accordance with an embodiment of the invention.

To analyze Poly IC mediated apoptosis, ACHN renal cancer cells were sensitized/treated with compounds 2, 3, 4, 5, 6, 7, 9, 1, and 10, (3-4 h) at the indicated concentrations followed by 10 μg/ml of Poly IC (High Molecular Weight, Invivogen) for 36-48 h. Cell viability was assessed by addition of MTS during the last four hours of Poly IC treatment. The results are depicted in FIGS. 3A-3I.

Example 2

This example demonstrates the percent growth inhibition of SK MEL28 melanoma cells in the presence of compounds 2, 3, 4, 5, 6, 7, 9, 1, and 10, respectively, at concentrations of 63 nM, 125 nM, 250 nM, and 500 nM, in the presence of absence of 10 μM poly IC.

To analyze Poly IC mediated apoptosis, SK MEL28 melanoma cells were sensitized/treated with compounds 2, 3, 4, 5, 6, 7, 9, 1, and 10, (3-4 h) at the indicated concentrations followed by 10 μg/ml of Poly IC (High Molecular Weight, Invivogen) for 36-48 h. Cell viability was assessed by addition of MTS during the last four hours of Poly IC treatment. The results are depicted in FIGS. 4A-4I.

Example 3

This example illustrates an effect of a sensitizer on production of caspase 8 and cFLIP by cells treated with compounds 9 and 1 in the presence or absence of 10 μM poly IC.

ACHN cells were grown in RPMI (RPMI, 5% FBS, Pen-strep, NEAA, HEPES, Glutamax, Sodium Pyruvate, 2ME), $2 \times 10^6$ cells/well were plated in 6 well plates and grown overnight, on day 2 compound 9 or compound 1 were added, including duplicate plates and incubated overnight. On day 3 either media or 10 ug/ml polyIC was added for 3 hours. Cells were lysed in RIPA buffer (30 mM Tris-HCL pH 7.5, 150 mM NaCl, 10% glycerol, 1% Triton X-100) supplemented with Pierce Halt Protease and Phosphatase Inhibitor and 40 μM ZVAD, the RIPA buffer also contained Pierce Universal Nuclease. Protein concentrations were measured using the Pierce BCA Protein Assay (Thermo Fisher Scientific, Waltham, Mass.), Twenty micrograms of each sample was run on a Bolt Gel (Thermo Fisher Scientific), transferred to a PVDF membrane using the BioRad Trans-Blot Turbo Transfer System (BioRad, Hercules, Calif.), briefly placed in Methanol, dried, rehydrated, and blocked in Pierce Start Block buffer. Blots were probed with either an anti-Caspase 8 cocktail (Cleaved Caspase-8 (Asp391) (18C8) Rabbit mAb #9496 1:1000, Cleaved Caspase-8 (Asp384) (11G10) Mouse mAb 1:5000, Caspase-8 (1C12) Mouse mAb #9746 1:5000, All from Cell Signaling Technology, Danvers, Mass.), anti-FLIP (7F10 1 ug/ml, Enzo Life Sciences, Farmingdale, N.Y.) or anti-GAPDH (GAPDH (D16H11) XP® Rabbit mAb (HRP Conjugate) 1:10,000, Cell Signaling) prepared in TBST (Tris Buffered Saline) containing 0.1% Tween 20 and 1% BSA. Blots were washed with TBST containing 0.5% Tween 20, probed with appropriate HRP labeled secondary (Pierce poly-HRP anti-rabbit and/or mouse at 1:50,000), washed again, treated with Pierce SuperSignal West Femto Maximum Sensitivity Substrate and imaged with Carestream BioMax MR film (Carestream Health, Rochester, N.Y.). The results are illustrated in FIGS. 5A and 5B.

As is apparent from FIGS. 5A and 5B, compound 1 was more active than compound 9 in both reducing the levels of cFLIPL+S as well as in promoting caspase-8 activation in response to subsequent exposure to poly IC.

Example 4

This example demonstrates the effect of bafilomycin on the sensitization of SK MEL28 melanoma cells to poly IC by compounds 9, 1, and 10.

To inhibit TLR 3 signaling, cells were treated with compound 9, compound 1, or compound 10 for 4 hours followed by addition of 50 nM of Balfilomycin A or DMSO for 2.5 h. Subsequently poly IC was added for 36-48 h and cell viability was assessed by addition of MTS during the last four hours of Poly IC treatment. The results for compounds 9, 1, and 10 are depicted in FIG. 6.

Incubation of cancer cells with bafilomycin-A1 prior to exposure to the combination of LG-02 and poly IC significantly reduced subsequent apoptosis (FIGS. 6A and 6B). This suggests that the binding of poly IC to TLR3 was probably a crucial signaling event in linking poly IC responses to the apoptosis death signaling machinery in the presence of active 17-β-hydroxywithanolides.

Example 5

This example demonstrates the results of titration experiments on the sensitization of melamoma cell lines SK MEL28, M14, and Malme, respectively, by compound 8 in the presence or absence of TRAIL.

For titration experiments in the presence or absence of TRAIL, cells were treated with various doses of compound 8 (0.97 nM-2000 nM) for 3 or 24 h followed by 10 ng/ml of recombinant TRAIL for 24 h. Cell viability was assessed by addition of MTS during the last four hours of TRAIL treatment. The results with SK MEL28, M14, and Malme cells are depicted in FIGS. 7A-7C, respectively.

As is apparent from the results depicted in FIGS. 7A-7C, compound 8 sensitized melamoma cell lines SK MEL28, M14, and Malme to apoptosis by TRAIL.

Example 6

This example demonstrates the results of titration experiments on the sensitization of melamoma cell lines M14 and Malme 3M by compounds 8 and 1 in the presence or absence of TRAIL.

Titration experiments were conducted as described in Example 5. The results for compound 8 on M14 cells are shown in FIG. 8A. The results for compound 8 on Malme 3M cells are shown in FIG. 8B. The results for compound 1 on M14 cells are shown in FIG. 8C. The results for compound 1 on Malme 3M cells are shown in FIG. 8D.

As is apparent from the results shown in FIGS. 8A-8D, compound 8 appeared to be more potent than compound 1 at lower concentrations on M14 and Malme 3M cells.

Example 7

This example demonstrates the results of titration experiments on the sensitization of ACHN renal cancer cells by compounds 9, 8, and 1 in the presence or absence of TRAIL. Titration experiments were conducted as described in Example 5. The results for compounds 9, 8, and 1 are shown in FIGS. 9A-9C, respectively.

Example 8

This example demonstrates the aeroponic cultivation and harvesting of *Physalis crassifolia* and *P. peruviana*.

Seeds were germinated in 1.0 inch Grodan rock-wool cubes in a Barnstead Lab-Line growth chamber kept at 28° C. with 16 h of fluorescent lighting and maintaining 25-50% humidity. After ca. 4 weeks in the growth chamber, seedlings with an aerial length of ca. 5.0 cm were transplanted to aeroponic culture boxes for further growth as described previously (PCT/US2009/005 146). For *P. crassifolia*, aerial parts of areoponically grown plants were harvested when they started to produce flowers (ca. 2 months under aeroponic growth conditions) and when fruits were almost mature (ca. 5 months under aeroponic growth conditions) and were processed separately. For *P. peruviana*, aerial parts of areoponically grown plants were harvested when fruits were almost mature (ca. 5 months under aeroponic growth conditions). Harvested plant materials were dried in the shade, powdered and stored at 5° C. prior to extraction.

Example 9

This example demonstrates the extraction and isolation of withanolides from two-month old aeroponically cultivated *P. crassifolia*.

Dried and powdered plant material (50.0 g) was extracted (×3) with MeOH (300 and 2×200 mL) in an ultrasonic bath at 25° C. for 1 h, filtered and the combined filtrates were concentrated in vacuo to afford the crude extract (6.7 g). This extract was subjected to solvent-solvent partitioning using 80% aq. MeOH (50 mL) and hexanes (3×50 mL). The 80% aq. MeOH solution thus obtained was diluted with water to 50% aq. MeOH and extracted with $CHCl_3$ (3×30 mL). Combined $CHCl_3$ extracts were concentrated and the resulting $CHCl_3$ fraction (755.0 mg) was subjected to column chromatography over RP silica gel (20.0 g) and eluted with 100 mL each of 70%, 80%, and 90% aq. MeOH followed by MeOH. The fraction eluted with 80% aq. MeOH which was found to contain most of the withanolides was concentrated and further fractionated by RP HPLC with a solvent gradient of MeOH and water (flow rate, 3 mL/min; 0-15 min, 50% aq. MeOH; 16-60 min, 60% MeOH with UV detection at 250 nm). Based on the HPLC trace obtained, ten fractions designated A-J [A (6.8 mg) at $t_R$=26.5 min; B (2.1 mg) at $t_R$=27.4 min; C (3.9 mg) at $t_R$=28.1 min; D (11.1 mg) at $t_R$=29.2 min; E (7.1 mg) at $t_R$=31.1 min; F (10.0 mg) at $t_R$=34.4 min; G (55.0 mg) at $t_R$=38.2 min; H (6.5 mg) at $t_R$=44.3 min; 1 (180.4 mg) at $t_R$=46.9 min; and J (8.3 mg) at $t_R$=58.1 min] were collected. Fractions A, D and F-J which contained withanolides were further purified by silica gel NP HPLC using mixtures of $CHCl_3$-MeOH as eluants (3 mL/min, UV detection at 254 nm). Fraction A afforded 15α-acetoxy-28-hydroxyphysachenolide D [6.1 mg, $t_R$=17.9 min, $CHCl_3$-MeOH (97:3)]; D afforded 15α-acetoxy-27-hydroxyphysachenolide D [6.5 mg, $t_R$=11.2 min, $CHCl_3$-MeOH (97:3)]; F afforded 27-hydroxyphysachenolide D [6.8 mg, $t_R$=8.7 min, $CHCl_3$-MeOH (97:3)]; G afforded 15α-hydroxyphysachenolide D [48.9 mg, $t_R$=14.4 min, $CHCl_3$-MeOH (97:3)]; I afforded physachenolide D [168 mg, $t_R$=8.8 min, $CHCl_3$-MeOH (97:3)] and 15α-acetoxyphysachenolide D [14.2 mg, $t_R$=19.3 min, $CHCl_3$-MeOH (99:1); and fraction J afforded 18-acetoxy-17-epi-withanolide K [4.2 mg, $t_R$=8.0 min, $CHCl_3$-MeOH (97:3)].

Example 10

This example demonstrates the extraction and isolation of withanolides from five-month old aeroponically cultivated *P. crassifolia*.

Dried powdered aerial parts of *P. crassifolia* (1.0 kg) were extracted (×3) for 24 h each time with MeOH (1400 mL, 800 mL, and 800 mL) in a shaker at 25° C. and filtered. Resulting filtrates were combined and concentrated in vacuo to afford the crude extract (150.0 g). A portion (50.0 g) of this extract was subjected to solvent-solvent partitioning using 80% aq. MeOH (200 mL) and hexanes (3×100 mL). The resulting 80% aq. MeOH fraction was diluted with water to 50% aq. MeOH and extracted with $CHCl_3$ (3×100 mL). Combined $CHCl_3$ extracts were concentrated under reduced pressure to afford the $CHCl_3$ fraction (5.47 g). This fraction was subjected to column chromatography on RP $C_{18}$ (100 g) and eluted with 200 mL each of 60%, 70%, 80%, 90% aq. MeOH and finally with MeOH to afford five fractions A-E: A (698.0 mg) eluted with 60% aq. MeOH; B (608.0 mg) with 70% aq. MeOH; C (522.0 mg) with 80% aq. MeOH; D (1.63 g) with 90% aq. MeOH; and E (2.18 g) with MeOH. Further purification of fraction A (500.0 mg) by RP HPLC using a gradient solvent system (increasing MeOH concentration from 35% aq. MeOH to 60% aq. MeOH in 40 min) afforded sub-fractions $A_1$ and $A_2$. Sub-fraction $A_1$ (72.8 mg) collected at $t_R$=15.4 min was separated by column chromatography over silica gel (10.0 g) and eluted with $CHCl_3$-MeOH (8:2) to afford 15α-acetoxyphysachenolide C (16.9 mg) and 15α-acetoxy-2,3-dihydrophysachenolide D-3β-O-sulfate (35.6 mg). Further purification of sub-fraction $A_2$ (26.9 mg) collected at $t_R$=40.0 min by silica gel (25.0 g) column chromatography and elution with $CHCl_3$-MeOH (85:15) afforded 15α-acetoxy-28-O-β-D-glucopyranosyl-physachenolide D (9.3 mg) and 2,3-dihydrophysachenolide D-3β-O-sulfate (6.6 mg). Fraction B (608.0 mg) obtained above was subjected to further purification by RP HPLC using a gradient solvent system (increasing methanol concentration from 45% aq. MeOH to 70% aq. MeOH in 50 min) yielding eight sub-fractions $B_1$-$B_8$ with retention times ($t_R$s) of 20, 25, 27, 33, 35, 37, 40, and 42 min, respectively. TLC analysis of these indicated that only sub-fractions $B_5$-$B_8$ contained withanolides. Further purification of sub-fraction $B_5$ (53.5 mg) by column chromatography over silica gel (20 g) and elution with $CHCl_3$-MeOH (96:4) afforded 15α-acetoxy-27-O-β-D-glucopyranosylphysachenolide D (24.8 mg). Similar purification of sub-fraction $B_6$ (133.3 mg) gave 15α-acetoxy-28-hydroxyphysachenolide D (124.0 mg). Sub-fraction $B_7$ (32.2 mg) on further purification by silica gel (5.0 g) column chromatography and elution with $CHCl_3$-MeOH (95:5) afforded 27-hydroxyphysachenolide D (9.0 mg). Sub-fraction $B_8$ (24.1 mg) on silica gel (20.0 g) column chromatography and elution with $CHCl_3$-MeOH (96:4) gave 15α,18-diacetoxy-28-hydroxy-17-epi-withanolide K (4.8 mg) and physachenolide. C (1) (2.4 mg). Fraction C (522.0 mg) resulting from the first column chromatographic separation was subjected to gel filtration chromatography on Sephadex LH-20 (100.0 g) and eluted with $CH_2Cl_2$-hexanes (4:1). Fractions obtained were combined based on their TLC profiles to afford four sub-fractions $C_1$-$C_4$. TLC investigation of these indicated that only $C_2$ and $C_3$ contained withanolides. Sub-fraction $C_2$ (272.7 mg) on further purification by silica gel NP HPLC [$CHCl_3$-MeOH (95:5), 3 mL/min, UV detection at 254 nm) afforded 15α-acetoxyphysachenolide D (95.0 mg, $t_R$=6.5 min) and physachenolide D (105.0 mg, $t_R$=7.5 min). Sub-fraction $C_3$ (28.2 mg) on further purification by RP HPLC (65% aq. MeOH, 3.0 mL/min, UV detection at 230 nm) gave another portion of physachenolide D (15.5 mg, $t_R$=24.6 min).

Example 11

This example demonstrates the extraction and isolation of 15α,18-diacetoxy-17-epi-withanolide K from soil-grown *P. crassifolia*.

The powdered plant material was extracted with 1:1 $CH_2Cl_2$-MeOH at room temperature for three times and the crude extract was obtained after concentration and drying. The 2.0 g of the crude extract was passed a 40 g C-18 open column, and the column was washed successively with 200 mL each of 20%. 40%, 60%, 80%, and 100% aq. MeOH.

The 60% MeOH fraction was further separated with preparative C-18 HPLC (Luna 250×10 mm C-18 column, 55-65% gradient increasing aq. MeOH in 30 min, detected at 225 nm, the peak at RT=18.3 min), and finally purified on 10 g SiO$_2$ open column (95:5 CHCl$_3$-MeOH) to give 15α, 18-diacetoxy-17-epi-withanolide K (15.7 mg).

Example 12

This example sets forth characterization data for the compounds disclosed in Examples 9-11.

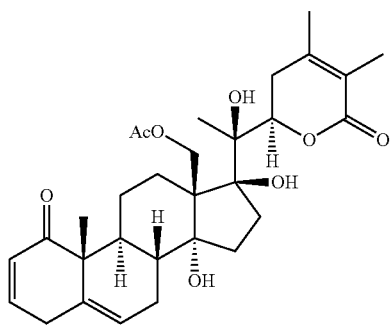

Physachenolide D

Off-white amorphous powder; $[\alpha]_D^{25}$+44.5 (c 0.69, MeOH); UV (MeOH) $\lambda_{max}$ (log ε) 223 (4.07) nm; $^1$H NMR (CDCl$_3$, 400 MHz) δ 6.74 (1H, ddd, J=10.0, 4.8, 2.4 Hz, H-3), 5.83 (1H, dd, J=10.0, 2.4 Hz, H-2), 5.56 (1H, 6.0 Hz, H-6), 4.91 (1H, 8.0 Hz, H-22), 4.44 (1H, d, J=11.2 Hz, H-18), 4.38 (1H, d, J=11.2 Hz, H-18), 3.24 (1H, brd, J=21.2 Hz, H-4). 2.80 (1H, dd, J=21.2, 4.8 Hz, H-4), 2.08 (3H, s, 18-OAc), 1.93 (3H, s, CH$_3$-28), 1.88 (3H, s, CH$_3$-27), 1.40 (3H, s, CH$_3$-21), 1.20 (3H, s, CH$_3$-19); $^{13}$C NMR (CDCl$_3$, 100 MHz) δ 203.9 (qC, C-1), 170.3 (qC, 18-OAc), 165.7 (qC, C-26), 149.6 (qC, C-24), 145.2 (CH, C-3), 135.1 (qC, C-5), 128.0 (CH, C-2), 125.0 (CH, C-6), 121.9 (qC, C-25), 88.2 (qC, C-17), 81.4 (qC, C-14), 79.7 (CH, C-22) 78.8 (qC, C-20), 65.3 (CH$_2$, C-18), 57.5 (qC, C-13), 50.6 (qC, C-10), 38.0 (CH$_2$, C-16), 37.6 (CH, C-8), 35.8 (CH, C-9), 33.8 (CH$_2$, C-23), 33.4 (CH$_2$, C-4), 33.0 (CH$_2$, C-15), 26.0 (CH$_2$, C-12), 25.7 (CH$_2$, C-7), 23.0 (CH$_2$, C-11), 21.3 (CH$_3$, 18-OAc), 20.6 (CH$_3$, C-28), 19.3 (CH$_3$, C-21), 18.7 (CH$_3$, C-19), 12.4 (CH$_3$, C-27); positive HRESIMS m/z 511.2683 [M-H$_2$O+H]$^+$ (calcd for C$_{30}$H$_{39}$O$_7$, 511.2690).

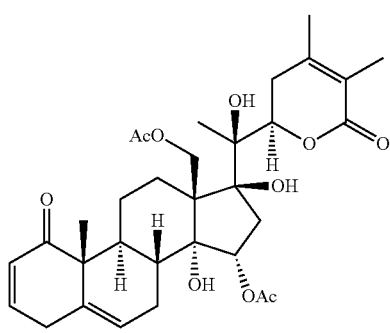

15α-Acetoxyphysachenolide D

Off-white amorphous powder; $[\alpha]_D^{25}$+64.0 (c 0.67, MeOH); UV (MeOH) $\lambda_{max}$ (log ε) 225 (4.05) nm; $^1$H NMR (CDCl$_3$, 400 MHz) δ 6.74 (1H, ddd, J=10.0, 4.8, 2.4 Hz, H-3), 5.83 (1H, dd, J=10.0, 2.0 Hz, H-2), 5.51 (1H, d, J=5.6 Hz, H-6), 5.16 (1H, t, J=8.8 Hz, H-15), 4.88 (1H, t, J=7.6 Hz, H-22), 4.69 (1H, d, J=11.6 Hz, H-18), 4.25 (1H, d, J=11.6 Hz, H-18), 3.23 (1H, brd, J=21.2 Hz, H-4), 2.79 (1H, dd, J=21.2, 4.8 Hz, H-4), 2.12 (3H, s, 15-OAc), 2.06 (3H, s, 18-OAc), 1.92 (3H, s, CH$_3$-28), 1.87 (3H, s, CH$_3$-27), 1.38 (3H, s, CH$_3$-21), 1.20 (3H, s, CH$_3$-19); $^{13}$C NMR (CDCl$_3$, 100 MHz) δ 203.8 (qC, C-1), 171.1 (qC, 15-OAc) 170.1 (qC, 18-OAc), 165.6 (qC, C-26), 149.9 (qC, C-24), 145.1 (CH, C-3), 134.8 (qC, C-5), 128.0 (CH, C-2), 124.9 (CH, C-6), 121.7 (qC, C-25), 85.1 (qC, C-17), 79.7 (qC, C-14), 79.5 (CH, C-22), 79.0 (qC, C-20), 75.8 (CH, C-15), 64.9 (CH$_2$, C-18), 57.4 (qC, C-13), 50.5 (qC, C-10), 43.7 (CH$_2$, C-16), 37.8 (CH, C-8), 35.8 (CH, C-9), 33.8 (CH$_2$, C-23), 33.3 (CH$_2$, C-4), 26.0 (CH$_2$, C-12), 25.6 (CH$_2$C-7), 22.7 (CH$_2$, C-11), 21.4 (CH$_3$, 18-OAc), 21.3 (CH$_3$, 15-OAc), 20.6 (CH$_3$, C-28), 19.6 (CH$_3$, C-21), 18.7 (CH$_3$, C-19), 12.4 (CH$_3$, C-27); positive HRESIMS m/z 609.2646 [M+Na]$^+$ (calcd for C$_{32}$H$_{42}$O$_{10}$Na, 609.2676).

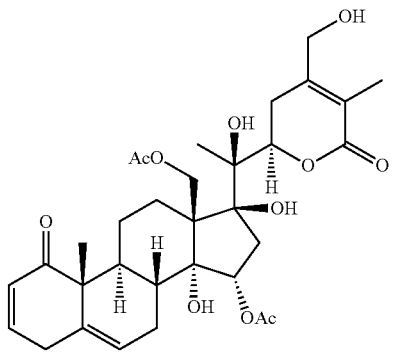

15α-Acetoxy-28-hydroxyphysachenolide D

Off-white amorphous powder; $[\alpha]_D^{25}$+62.5 (c 0.36, MeOH); UV (MeOH) $\lambda_{max}$ (log ε) 222.5 (4.19) nm; $^1$H NMR (CDCl$_3$, 400 MHz) δ 6.74 (1H, ddd, J=10.0, 4.8, 2.4 Hz, H-3), 5.82 (1H, dd, J=10.0, 2.0 Hz, H-2), 5.52 (1H, d, J=6.0 Hz, H-6), 5.12 (1H, J=8.8 Hz, H-15), 4.86 (1H, brd, J=11.4 Hz, H-22), 4.53 (1H, d, J=11.6 Hz, H-18), 4.40 (1H, d, J=11.6 Hz, H-28), 4.37 (1H, d, J=11.6 Hz, H-18), 4.26 (1H, d, J=11.6 Hz, H-28), 3.24 (1H, brd, J=21.2 Hz, H-4), 2.79 (1H, dd, J=21.2, 4.8 Hz, H-4), 2.14 (3H, s, 15-OAc), 2.06 (3H, s, 18-OAc), 1.84 (3H, s, CH$_3$-27), 1.38 (3H, s, CH$_3$-21), 1.19 (3H, s, CH$_3$-19); $^{13}$C NMR (CDCl$_3$, 100 MHz) δ 204.1 (qC, C-1), 171.1 (qC, 18-OAc), 170.8 (qC, 15-OAc), 165.9 (qC, C-26), 151.9 (qC, C-24), 145.4 (CH, C-3), 134.8 (qC, C-5), 127.9 (CH, C-2), 124.9 (CH, C-6), 121.6 (qC, C-25), 85.5 (qC, C-17), 81.2 (CH, C-22), 80.2 (qC, C-14), 79.1 (qC, C-20), 75.9 (CH, C-15), 64.5 (CH$_2$, C-18), 61.3 (CH$_2$, C-28), 57.4 (qC, C-13), 50.5 (qC, C-10), 43.2 (CH$_2$, C-16), 37.8 (CH, C-8), 35.8 (CH, C-9), 33.3 (CH$_2$, C-4), 28.0 (CH$_2$C-23), 25.6 (CH$_2$, C-7), 25.4 (CH$_2$, C-12), 22.8 (CH$_2$, C-11), 21.4 (CH$_3$, 15-OAc), 21.1 (CH$_3$, 18-OAc), 20.5 (CH$_3$, C-21), 18.8 (CH$_3$, C-19), 11.9 (CH$_3$, C-27); positive HRESIMS m/z 625.2623 [M+Na]$^+$ (calcd for C$_{32}$H$_{42}$O$_{11}$Na, 625.2625).

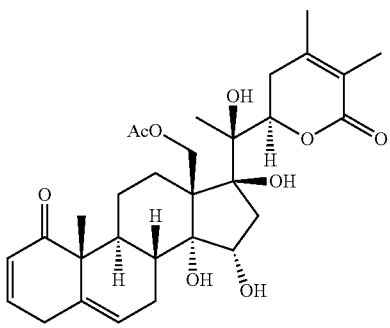

15α-Hydroxyphysachenolide D

Off-white amorphous powder; $[\alpha]_D^{25}$ +28 (c 0.16, MeOH); UV (MeOH) $\lambda_{max}$ (log ε) 222 (3.81) nm; $^1$H NMR (CDCl$_3$, 400 MHz) δ 6.72 (1H, ddd, J=10.0, 4.9, 2.5 Hz, H-3), 5.80 (1H, dd, J=10.0, 2.0 Hz, H-2), 5.53 (1H, d, J=5.6 Hz, H-6), 4.87 (1H, dd, J=12.1, 3.9 Hz, H-22), 4.56 (1H, d, J=11.6 Hz, H-18), 4.24 (1H, d, J=11.6 Hz, H-18), 4.06 (1H, t, J=7.9 Hz, H-15), 3.21 (1H, dd, J=22.0, 3.2 Hz, H-4), 2.77 (1H, dd, J=22.0, 4.8 Hz, H-4), 2.07 (3H, s, 18-OAc), 1.89 (3H, s, CH$_3$-28), 1.84 (3H, s, CH$_3$-27), 1.36 (3H, s, CH$_3$-21); 1.18 (3H, s, CH$_3$-19); $^{13}$C NMR (CDCl$_3$, 100 MHz) δ 204.1 (qC, C-1), 170.3 (qC, 18-OAc), 166.3 (qC, C-26), 150.2 (qC, C-24), 145.4 (CH, C-3), 134.3 (qC, C-5), 127.8 (CH, C-2), 125.4 (CH, C-6), 121.6 (qC, C-25), 85.1 (qC, C-17), 80.1 (qC, C-14), 80.1 (CH, C-22), 78.9 (qC, C-20), 74.1 (CH, C-15), 65.0 (CH$_2$, C-18), 57.1 (qC, C-13), 50.6 (qC, C-10), 48.2 (CH$_2$, C-16), 37.8 (CH, C-8), 35.8 (CH, C-9), 33.8 (CH$_2$, C-23), 33.3 (CH$_2$C-4), 26.4 (CH$_2$, C-12), 25.9 (CH$_2$, C-7), 22.8 (CH$_2$, C-11), 21.3 (CH$_3$, 18-OAc), 20.6 (CH$_3$, C-28), 19.1 (CH$_3$, C-21), 18.8 (CH$_3$, C-19), 12.3 (CH$_3$, C-27); positive HRESIMS m/z 567.2570 [M+Na]$^+$ (calcd for C$_{30}$H$_{40}$O$_9$Na, 567.2570).

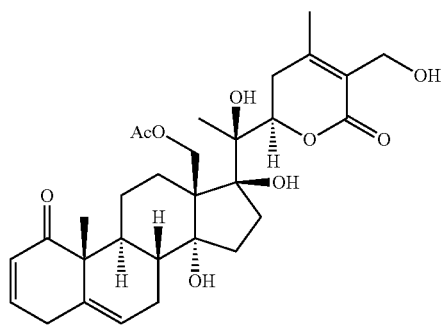

27-Hydroxyphysachenolide D

Off-white amorphous powder; $[\alpha]_D^{25}$ +91 (c 0.13, MeOH); UV (MeOH) $\lambda_{max}$ (log ε) 224 (4.19) nm; $^1$H NMR (CDCl$_3$, 400 MHz) δ 6.76 (1H, ddd, J=10.0, 4.9, 2.5 Hz, H-3), 5.84 (1H, dd, J=10.0, 2.0 Hz, H-2), 5.55 (1H, d, J=5.9 Hz, H-6), 4.59 (1H, brd, J=12.2 Hz, H-22), 4.33 (1H, d, J=12.4 Hz, H-27), 4.28 (1H, d, J=12.4 Hz, H-27), 4.20 (2H, brs, H-18), 3.25 (1H, brd, J=21.2 Hz, H-4), 2.80 (1H, dd, J=21.2, 4.8 Hz, H-4), 2.03 (3H, s, 18-OAc), 2.00 (3H, s, CH$_3$-28), 1.42 (3H, s, CH$_3$-21), 1.23 (3H, s, CH$_3$-19); $^{13}$C NMR (CDCl$_3$, 100 MHz) δ 204.3 (qC, C-1), 171.1 (qC, 18-OAc), 166.2 (qC, C-26), 155.5 (qC, C-24), 145.6 (CH, C-3), 135.4 (qC, C-5), 127.7 (CH, C-2), 124.7 (qC, C-26), 124.2 (qC, C-25), 124.2 (CH, C-6), 87.5 (qC, C-17), 85.4 (qC, C-14), 81.5 (CH, C-22), 76.9 (qC, C-20), 62.8 (CH$_2$, C-18), 56.8 (CH$_2$, C-27), 53.9 (qC, C-13), 50.8 (qC, C-10), 36.8 (CH, C-8), 36.0 (CH, C-9), 33.6 (CH$_2$, C-23), 33.4 (CH$_2$, C-4), 33.1 (CH$_2$C-15), 32.8 (CH$_2$, C-16), 24.7 (CH$_2$, C-7), 22.1 (CH$_2$, C-12), 22.0 (CH$_2$, C-11), 21.1 (CH$_3$, 18-OAc), 20.0 (CH$_3$, C-28), 18.9 (CH$_3$, C-21), 18.1 (CH$_3$, C-19); positive HRESIMS m/z 567.2570 [M+Na]$^+$ (calcd for C$_{30}$H$_{40}$O$_9$Na, 567.2570).

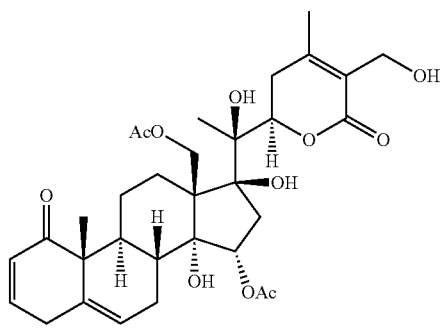

15α-Acetoxy-27-hydroxyphysachenolide D

Off-white amorphous powder; $[\alpha]_D^{25}$ +65 (c 0.14, MeOH); UV (MeOH) $\lambda_{max}$ (log ε) 222 (4.07) nm; $^1$H NMR (CDCl$_3$, 400 MHz) δ 6.73 (1H, ddd, J=10.0, 4.9, 2.5 Hz, H-3), 5.82 (1H, dd, J=10.0, 1.9 Hz, H-2), 5.50 (1H, brd, J=5.5 Hz, H-6), 5.13 (1H, t, J=8.8 Hz, H-15), 4.94 (1H, dd, J=12.4, 3.6 Hz, H-22), 4.68 (1H, d, J=11.5 Hz, H-18), 4.34 (2H, brs, H-27), 4.22 (1H, d, J=11.5 Hz, H-18), 3.23 (1H, brd, J=21.6 Hz, H-4), 2.78 (1H, dd, J=21.6, 4.8 Hz, H-4) 2.10 (3H, s, 15-OAc), 2.06 (3H, s, 18-OAc), 2.03 (3H, s, CH$_3$-28), 1.38 (3H, s, CH$_3$-21), 1.18 (3H, s, CH$_3$-19); $^{13}$C NMR (CDCl$_3$, 100 MHz) δ 203.8 (qC, C-1), 171.3 (qC, 15-OAc), 170.2 (qC, 18-OAc), 166.0 (qC, C-26), 154.4 (qC, C-24), 145.2 (CH, C-3), 134.7 (qC, C-5), 127.9 (CH, C-2), 125.4 (qC, C-25), 124.9 (CH, C-6), 85.1 (qC, C-17), 80.3 (CH, C-22), 79.8 (qC, C-14), 78.8 (qC, C-20), 75.8 (CH, C-15), 64.8 (CH$_2$, C-18), 57.3 (qC, C-13), 57.0 (CH$_2$, C-27), 50.5 (qC, C-10), 43.5 (CH$_2$, C-16), 37.7 (CH, C-8), 35.7 (CH, C-9), 34.0 (CH$_2$, C-23), 33.3 (CH$_2$, C-4), 25.9 (CH$_2$, C-12), 25.6 (CH$_2$, C-7), 22.7 (CH$_2$, C-11), 21.4 (CH$_3$, 18-OAc), 21.3 (CH$_3$, 15-OAc), 20.2 (CH$_3$, C-28), 19.3 (CH$_3$, C-21); 18.7 (CH$_3$, C-19); positive HRESIMS m/z 603.2802 [M+H]$^+$ (calcd for C$_{32}$H$_{42}$O$_{11}$, 603.2805).

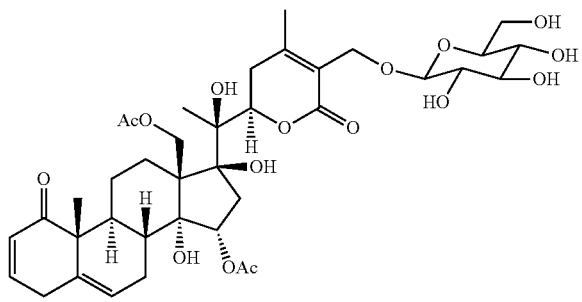

15α-Acetoxy-27-O-β-D-glucopyranosylphysachenolide D

Off-white amorphous powder; $[\alpha]_D^{25}$ +49 (c 0.15, MeOH); UV (MeOH) $\lambda_{max}$ (log ε) 221 (4.10) nm; $^1$H NMR (CDCl$_3$, 400 MHz) δ 6.73 (1H, brd, J=10.0 Hz, H-3), 5.78 (1H, brd, J=10.0 Hz, H-2), 5.48 (1H, brd, J=6.0 Hz, H-6), 5.01 (1H, t, J=8.4 Hz, H-15), 4.89 (1H, brd, J=12.5 Hz, H-22), 4.54 (2H, m, H-18 and H-27), 4.37 (1H, d, J=11.1 Hz, H-27), 4.31 (1H, d, J=7.8 Hz, Glc-1'), 4.21 (1H, d, J=11.2 Hz, H-27), 3.81 (1H, dd, J=12.0, 3.2 Hz, Glc-6'), 3.69 (1H, dd, J=12.0, 4.8 Hz, Glc-6'), 3.21 (1H, m, H-4), 2.76 (1H, m, H-4), 2.70 (1H, m, H-23), 2.53 (1H, m, H-23), 2.04 (3H, s, 18-OAc), 2.02 (3H, s, 15-OAc), 2.01 (3H, s, $CH_3$-28), 1.28 (3H, s, $CH_3$-21), 1.14 (3H, s, $CH_3$-19); $^{13}$C NMR (CDCl$_3$, 100 MHz) δ 204.5 (qC, C-1), 171.6 (qC, 15-OAc), 170.6 (qC, 18-OAc), 166.3 (qC, C-26), 158.8 (qC, C-24), 145.8 (CH, C-3), 134.5 (qC, C-5), 127.7 (CH, C-2), 125.0 (CH, C-6), 122.2 (qC, C-25), 102.2 (CH, Glc-1'), 84.6 (qC, C-17), 80.8 (CH, C-22), 79.4 (qC, C-14), 78.4 (qC, C-20), 76.3 (CH, Glc-5'), 76.1 (CH, C-15), 75.9 (CH, Glc-3'), 73.2 (CH, Glc-2'), 70.1 (CH, Glc-4'), 64.5 ($CH_2$, C-18), 62.4 ($CH_2$, C-27), 61.9 ($CH_2$, Glc-6'), 57.0 (qC, C-13), 50.4 (qC, C-10), 42.7 ($CH_2$, C-16), 37.6 (CH, C-8), 35.7 (CH, C-9), 34.1 ($CH_2$, C-23), 33.2 ($CH_2$, C-4), 25.7 ($CH_2$, C-12), 25.5 ($CH_2$, C-7), 22.8 ($CH_2$, C-1), 21.2 ($CH_3$, 15-OAc), 21.1 ($CH_3$, 18-OAc), 20.5 ($CH_3$, C-28), 18.7 ($CH_3$, C-19), 18.4 ($CH_3$, C-21); positive HRESIMS m/z, 765.3322 [M+H]$^+$ (calcd for $C_{38}H_{53}O_{16}$, 765.3334).

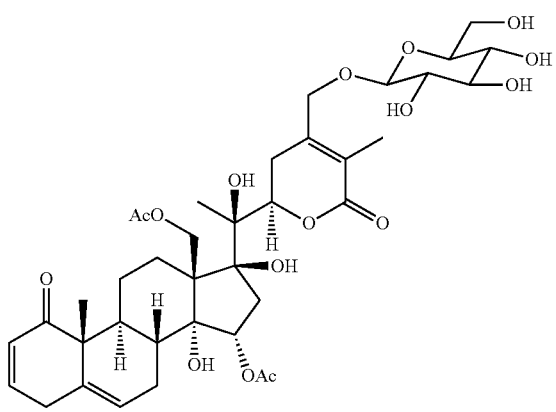

15α-Acetoxy-28-O-β-D-glucopyranosylphysachenolide D

Off-white amorphous powder; $[α]_D^{25}$+43 (c 0.18, MeOH); UV (MeOH) $λ_{max}$ (log ε) 222 (4.07) nm; $^1$H NMR (CDCl$_3$, 400 MHz) δ 6.73 (1H, ddd, J=10.0, 4.8, 2.4 Hz, H-3), 5.78 (1H, dd, J=10.0, 2.0 Hz, H-2), 5.48 (1H, brd, 5.3 Hz, H-6), 5.11 (1H, t, J=8.8 Hz, H-15), 4.83 (1H, dd, J=13.2, 2.4 Hz, H-22), 4.51 (1H, d, J=11.6 Hz, H-18), 4.38 (2H, m, H-28), 4.26 (1H, d, 11.6 Hz, H-18), 4.20 (1H, d, J=7.7 Hz, Glc-1'), 3.78 (1H, dd, J-12.0, 3.2 Hz, Glc-6'), 3.71 (1H, dd, 12.0, 4.4 Hz, Glc-6'), 3.21 (1H, m, H-4), 2.88 (1H, brd, J=8.8 Hz, H-23), 2.76 (1H, m, H-4), 2.42 (1H, m, H-23), 2.08 (3H, s, 18-OAc), 2.02 (3H, s, 15-OAc), 1.84 (3H, s, $CH_3$-27), 1.29 (3H, s, $CH_3$-21), 1.15 (3H, s, $CH_3$-19); $^{13}$C NMR (CDCl$_3$, 100 MHz) δ 204.6 (qC, C-1), 171.6 (qC, 15-OAc), 171.3 (qC, 18-OAc), 166.6 (qC, C-26), 148.8 (qC, C-24), 145.8 (CH, C-3), 134.5 (qC, C-5), 127.7 (CH, C-2), 125.0 (CH, C-6), 123.6 (qC, C-25), 102.1 (CH, Glc-1'), 84.7 (qC, C-17), 81.2 (CH, C-22), 79.4 (qC, C-14), 78.5 (qC, C-20), 76.4 (CH, Glc-5'), 76.1 (CH, C-15), 75.8 (CH, Glc-3'), 73.3 (CH, Glc-2'), 69.8 (CH, Glc-4'), 67.3 ($CH_2$, C-28), 64.8 ($CH_2$, C-18), 61.6 ($CH_2$, 57.1 (qC, C-13), 50.5 (qC, C-10), 42.9 ($CH_2$, C-16), 37.6 (CH, C-8), 35.7 (CH, C-9), 33.2 ($CH_2$, C-4), 29.2 ($CH_2$, C-23), 25.6 ($CH_2$, C-12), 25.5 ($CH_2$, C-7), 22.6 ($CH_2$, C-11), 21.3 ($CH_3$, 18-OAc), 21.1 ($CH_3$, 15-OAc), 18.9 ($CH_3$, C-21), 18.6 ($CH_3$, C-19), 12.0 ($CH_3$, C-27); positive HRESIMS 787.3131 [M+Na]$^+$ (calcd for $C_{38}H_{52}NaO_{16}$, 787.3153).

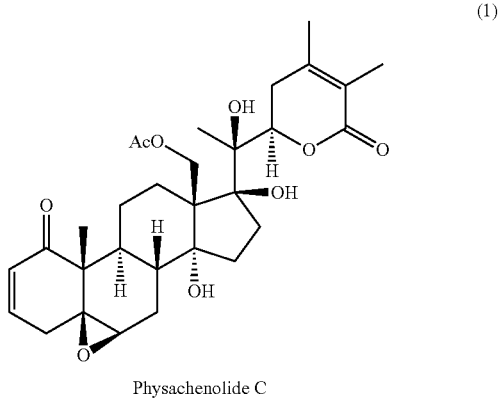

(1)

Physachenolide C

Off-white amorphous powder; $[α]_D^{25}$+102 (c 0.10, MeOH); $^1$H NMR (CDCl$_3$, 400 MHz): δ 6.68 (1H, ddd, J=10.0, 4.8, 2.0 Hz, H-3), 5.91 (1H, dd, J=10.0, 2.0 Hz, H-2), 4.88 dd, J=9.2, 7.6 Hz, H-22), 4.40 (1H, d, J=11.6 Hz, H-18), 4.30 (1H, d, J=11.6 Hz, H-18), 3.47 (1H, s, H-6α), 3.02-3.12 (2H, m, H-4 and H-23), 2.08 (3H, s, 18-OAc), 1.92 (3H, s, H-28), 1.88 (3H, s, H-27), 1.40 (3H, s, H-21), 1.32 (3H, s, H-19). $^{13}$C NMR (CDCl$_3$, 100 MHz): δ 202.5 (qC, C-1), 170.2 (qC, 18-OAc), 165.5 (qC, C-26), 149.9 (qC, C-24), 142.3 (CH, C-3), 128.9 (CH, C-2), 121.9 (qC, C-25), 88.1 (qC, C-17), 80.9 (qC, C-14), 79.5 (CH, C-22), 78.9 (qC, C-20), 65.3 ($CH_2$, C-18), 64.3 (qC, C-5), 58.7 (CH, C-6), 57.4 (qC, C-13), 48.5 (qC, C-10), 37.9 ($CH_2$, C-16), 35.3 (CH, C-9), 33.9 ($CH_2$, C-23), 33.8 ($CH_2$, C-4), 32.8 ($CH_2$, C-15), 31.8 ($CH_2$, C-8), 25.9 ($CH_2$, C-12), 23.6 ($CH_2$, C-7), 22.1 ($CH_2$, C-11), 21.3 ($CH_3$, 18-OAc), 20.6 ($CH_3$, C-28), 19.4 ($CH_3$, C-21), 15.3 ($CH_3$, C-19), 12.4 ($CH_3$, C-27); LR-APCIMS (positive): m/z 527 [MH]$^+$.

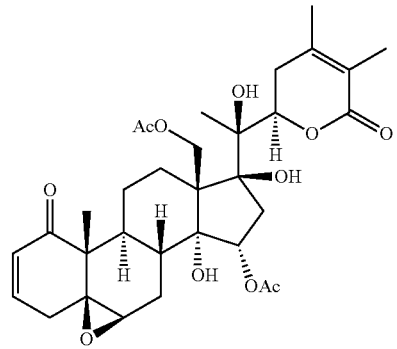

15α-Acetoxyphysachenolide C

Off-white amorphous powder; $[α]_D^{25}$+80 (c 0.47, MeOH); UV (MeOH) $λ_{max}$ (log ε) 225 (3.94) nm; NMR (CDCl$_3$, 400 MHz): δ 6.81 (1H, ddd, J=9.9, 6.3, 2.3 Hz, H-3), 6.00 (1H, dd, J=10.1, 2.7 Hz, H-2), 5.03 (1H, t, J=8.8 Hz, H-15), 4.84 (1H, t, J=8.3 Hz, H-22), 4.55 (1H, J=11.7 Hz, H-18), 4.24 (1H, d, 11.7 Hz, H-18), 3.12 (1H, brs, H-6α), 2.93 (1H, m, H-4), 2.10 (3H, s, 18-OAc), 2.07 (3H, s, 15-OAc), 1.91 (3H, s, H-28), 1.87 (3H, s, H-27), 1.36 (3H, s, H-21), 1.21 (3H, s, H-19), $^{13}$C NMR (CDCl$_3$, 100 MHz):

δ 202.7 (qC, C-1), 170.9 (qC, 15-OAc), 168.9 (qC, 18-OAc), 165.4 (qC, C-26), 149.9 (qC, C-24), 143.9 (CH, C-3), 129.6 (CH, C-2), 121.8 (qC, C-25), 84.7 (qC, C-17), 79.7 (qC, C-14), 79.3 (CH, C-22), 79.0 (qC, C-20), 75.9 (CH, C-15), 64.8 (CH$_2$, C-18), 63.8 (CH, C-6), 61.8 (qC, C-5), 57.3 (qC, C-13), 48.4 (qC, C-10), 43.8 (CH$_2$, C-16), 36.8 (CH, C-9), 34.6 (CH, C-8), 33.9 (CH$_2$, C-23), 32.8 (CH$_2$, C-4), 26.0 (CH$_2$, C-12), 25.7 (CH$_2$, C-7), 22.8 (CH$_2$, C-11), 21.4 (CH$_3$, 15-OAc), 21.3 (CH$_3$, 18-OAc), 20.6 (CH$_3$, C-28), 19.4 (CH$_3$, C-21), 14.7 (CH$_3$, C-19), 12.4 (CH$_3$, C-27); positive HRESIMS m/z 603.2805 [M+H]$^+$ (calcd for C$_{32}$H$_{43}$O$_{11}$, 603.2805).

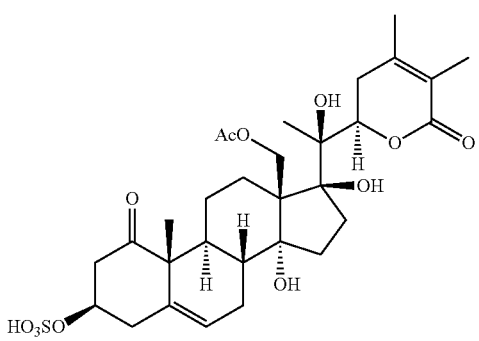

2,3-Dihydrophysachenolide D-3β-O-sulfate

Off-white amorphous powder; [α]$_D^{25}$+74 (c 0.26, MeOH); UV (MeOH) λ$_{max}$ (log ε) 222.5 (3.86) nm; $^1$H NMR (CDCl$_3$, 400 MHz): δ 5.59 (1H, brs, H-6), 4.79 (1H, dd, J=13.3, 3.2 Hz, H-22), 4.49 (1H, ddd, J=12.8, 9.6, 7.2 Hz, H-3α), 4.39 (1H, d, J=11.4 Hz, H-18), 4.18 (1H, d, J=11.4 Hz, H-18), 2.02 (3H, s, 18-OAc), 1.87 (3H, s, H-28), 1.80 (3H, s, H-27), 1.30 (3H, s, H-21), 1.16 (3H, s, H-19). $^{13}$C NMR (CDCl$_3$, 100 MHz): δ 212.4 (qC, C-1), 170.8 (qC, 18-OAc), 167.2 (qC, C-26), 150.9 (qC, C-24), 134.3 (qC, C-5), 126.1 (CH, C-6), 121.3 (qC-25), 87.9 (qC-17), 81.2 (qC, C-14), 80.8 (CH, C-22), 78.2 (qC, C-20), 74.4 (CH, C-3), 64.8 (CH$_2$, C-18), 57.4 (qC, C-13), 52.8 (qC, C-10), 44.4 (CH$_2$, C-2), 37.7 (CH$_2$, C-4), 37.4 (CH$_2$, C-16), 36.0 (CH, C-8), 35.5 (CH, C-9), 33.7 (CH$_2$, C-23), 32.5 (CH$_2$, C-15), 25.7 (CH$_2$, C-7), 25.4 (CH$_2$, C-12), 21.8 (CH$_2$, C-11), 21.2 (CH$_3$, 18-OAc), 20.5 (CH$_3$, C-28), 18.4 (CH$_3$, C-21), 17.1 (CH$_3$, C-19), 12.1 (CH$_3$, C-27); positive HRESIMS m/z 609.2369 [M+H]$^+$ (calcd for C$_{30}$H$_{41}$O$_{11}$S, 609.2364).

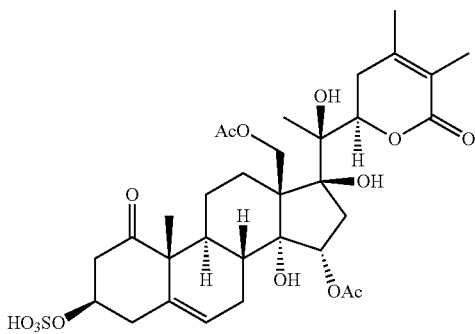

15α-Acetoxy-2,3-dihydrophysachenolide D-3β-O-sulfate

Off-white amorphous powder; [α]$_D^{25}$+81 (c 0.33, MeOH); UV (MeOH) λ$_{max}$ (log ε) 222 (3.83) nm; $^1$H NMR (CDCl$_3$, 400 MHz): δ 5.54 (1H, brs, H-6), 5.00 (1H, dd, J=9.2, 8.4 Hz, H-15β), 4.76 (1H, dd, J=13.6, 3.2 Hz, H-22), 4.47 (1H, ddd, J=14.0, 9.6, 6.9 Hz, H-3α), 4.50 (1H, d, J=11.6 Hz, H-18), 4.14 (1H, d, J=11.6 Hz, H-18), 2.02 (3H, s, 18-OAc), 2.01 (3H, s, 15-OAc), 1.86 (3H, s, H-28), 1.78 (3H, s, H-27), 1.25 (3H, s, H-21), 1.14 (3H, s, H-19). $^{13}$C NMR (CDCl$_3$, 100 MHz): δ 212.3 (qC, C-1), 171.7 (qC, 15-OAc), 170.7 (qC, 18-OAc), 167.3 (qC, C-26), 151.2 (qC, C-24), 133.9 (qC, C-5), 126.2 (CH, C-6), 121.3 (qC, C-25), 84.6 (qC, C-17), 80.7 (CH, C-22), 79.3 (qC, C-14), 78.3 (qC, C-20), 76.0 (CH, C-15), 74.4 (CH, C-3), 64.3 (CH$_2$, C-18), 57.1 (qC, C-13), 52.7 (qC, C-10), 44.5 (CH$_2$, C-2), 42.6 (CH$_2$, C-16), 37.7 (CH$_2$, C-4), 36.2 (CH, C-8), 35.7 (CH, C-9), 33.8 (CH$_2$, C-23), 32.5 (CH$_2$, C-15), 25.7 (CH$_2$, C-7), 25.3 (CH$_2$, C-12), 21.7 (CH$_2$, C-11), 21.7 (CH$_3$, 18-OAc), 21.3 (CH$_3$, 15-OAc), 20.5 (CH$_3$, C-28), 18.4 (CH$_3$, C-21), 17.7 (CH$_3$, C-19), 12.1 (CH$_3$C-27); positive HRESIMS m/z 685.2525 [M+H]$^+$ (calcd for C$_{32}$H$_{45}$O$_{14}$S, 685.2530).

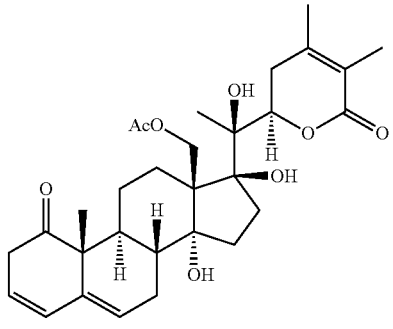

18-Acetoxy-17-epi-withanolide K

Off-white amorphous powder; [α]$_D^{25}$+63 (c 0.68, MeOH); UV (MeOH) λ$_{max}$ (log ε) 228 (4.01) nm; $^1$H NMR (CDCl$_3$, 400 MHz): δ 6.01 (1H, brd, J=10.0 Hz, H-4), 5.64 (1H, brd, J=2.8 Hz, H-6), 5.56 (1H, m, H-3), 4.89 (1H, t, J=8.0 Hz, H-22), 4.44 (1H, d, J=11.2 Hz, H-18), 4.37 (1H, d, J=11.2 Hz, H-18), 3.23 (1H, brd, J=19.6 Hz, H-2), 2.70 (1H, dd, J=19.6, 4.0 Hz, H-2), 2.08 (3H, s, 18-OAc), 1.92 (3H, s, CH$_3$-28), 1.88 (3H, s, CH$_3$-27), 1.41 (3H, s, CH$_3$-21), 1.33 (3H, s, CH$_3$-19); $^{13}$C NMR (CDCl$_3$, 100 MHz) δ 210.4 (qC C-1), 170.2 (qC, 18-OAc), 165.6 (qC, C-26), 149.6 (qC, C-24), 140.4 (qC, C-5), 129.4 (CH, C-4), 127.5 (CH, C-6), 121.9 (qC, C-25), 121.2 (CH, C-3), 88.3 (qC, C-17), 81.2 (qC, C-14), 79.7 (CH, C-22) 78.8 (qC, C-20), 65.2 (CH$_2$, C-18), 57.7 (qC, C-13), 52.2 (qC, C-10), 39.6 (CH$_2$, C-2), 38.0 (CH$_2$, C-16), 36.2 (CH, C-8), 34.0 (CH, C-9), 33.8 (CH$_2$, C-23), 32.9 (CH$_2$, C-15), 25.9 (CH$_2$, C-7), 25.8 (CH$_2$, C-12), 21.7 (CH$_2$, C-11) 21.3 (CH$_3$, 18-OAc), 20.6 (CH$_3$, C-28), 19.3 (CH$_3$, C-21), 20.1 (CH$_3$, C-19), 12.4 (CH$_3$, C-27); positive HRESIMS m/z 511.2691 [M+H]$^+$ (calcd for C$_{30}$H$_{39}$O$_7$, 511.2690).

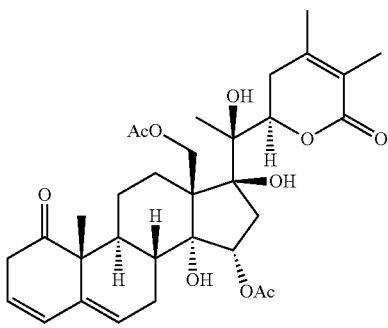

15α,18-Diacetoxy-17-epi-withanolide K

Off-white amorphous powder; $[\alpha]_D^{25}$+87 (c 0.29, MeOH); UV (MeOH) $\lambda_{max}$ (log ε) 229.5 (4.13) nm; $^1$H NMR (CDCl$_3$, 400 MHz): δ 6.00 (1H, brd, J=10.0 Hz, H-4), 5.59 (1H, overlapped, H-6), 5.56 (1H, overlapped, H-3), 5.20 (1H, t, J=8.0 Hz, H-22), 4.86 (1H, m, H-15β), 4.70 (1H, d, J=12.0 Hz, H-18), 4.24 (1H, d, J=12.0 Hz, H-18), 3.23 (1H, brd, J=19.6 Hz, H-2), 2.71 (1H, dd, J=19.6, 4.0 Hz, H-2), 2.13 (3H, s, 18-OAc), 2.08 (3H, s, 15-OAc), 1.92 (3H, s, CH$_3$-28), 1.87 (3H, s, CH$_3$-27), 1.39 (3H, s, CH$_3$-21), 1.35 (3H, s, CH$_3$-19); $^{13}$C NMR (CDCl$_3$, 100 MHz) δ 210.2 (qC, C-1), 171.1 (qC, 15-OAc), 169.9 (qC, 18-OAc), 165.3 (qC, C-26), 149.8 (qC, C-24), 140.1 (qC, C-5), 129.2 (CH, C-4), 127.2 (CH, C-6), 121.9 (qC, C-25), 121.5 (CH, C-3), 85.1 (qC, C-17), 79.6 (qC, C-14), 79.5 (CH, C-22), 79.0 (qC, C-20), 75.7 (CH, C-15), 64.9 (CH$_2$, C-18), 57.8 (qC, C-13), 52.2 (qC, C-10), 39.7 (CH$_2$, C-2), 43.7 (CH$_2$, C-16), 36.6 (CH, C-8), 34.1 (CH, C-9), 33.8 (CH$_2$, C-23), 25.9 (CH$_2$, C-7), 25.9 (CH$_2$, C-12), 21.5 (CH$_2$, C-11), 21.4 (CH$_3$, 15-OAc), 21.2 (CH$_3$, 18-OAc), 20.6 (CH$_3$, C-28), 20.1 (CH$_3$, C-19), 19.7 (CH$_3$, C-21), 12.4 (CH$_3$, C-27), positive HRESIMS m/z 569.2736 [M+H]$^+$ (calcd for C$_{32}$H$_{41}$O$_9$, 569.2745).

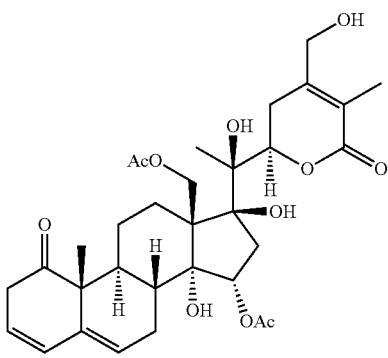

15α,18-Diacetoxy-28-hydroxy-17-epi-withanolide K

Off-white amorphous powder; $[\alpha]_D^{25}$+65 (c 0.06, MeOH); UV (MeOH) $\lambda_{max}$ (log ε) 228 (3.97) nm; $^1$H NMR (CDCl$_3$, 400 MHz): δ 6.00 (1H, brd, J=10.0 Hz, H-4), 5.60 (1H, overlapped, H-6), 5.57 (1H, overlapped, H-3), 4.88 brd, J=11.5 Hz, H-22), 5.18 (1H, t, J=8.9 Hz, H-15β), 4.61 (1H, d, J=11.6 Hz, H-18), 4.44 (1H, d, J=14.1 Hz, H-28), 4.34 (1H, d, J=11.6 Hz, H-18), 4.28 (1H, d, J=14.1 Hz, H-28), 3.24 (1H, brd, J=19.8 Hz, H-2), 2.92 (1H, d, J=18.3 Hz, H-23), 2.71 (1H, dd, J=19.8, 4.4 Hz, H-2), 2.14 (3H, s, 18-OAc), 2.08 (3H, s, 15-OAc), 1.87 (3H, s, CH$_3$-27), 1.41 (3H, s, CH$_3$-21), 1.35 (3H, s, CH$_3$-19); $^{13}$C NMR (CDCl$_3$, 100 MHz) δ 210.4 (qC, C-1), 171.1 (qC, 15-OAc), 170.4 (qC, 18-OAc), 165.5 (qC, C-26), 151.2 (qC, C-24), 140.1 (qC, C-5), 129.2 (CH, C-4), 127.1 (CH, C-6), 121.9 (qC, C-25), 121.5 (CH, C-3), 85.5 (qC, C-17), 80.6 (CH, C-22), 79.8 (qC, C-14), 79.2 (qC, C-20), 75.6 (CH, C-15), 64.8 (CH$_2$, C-18), 61.4 (CH$_2$, C-28), 57.7 (qC, C-13), 52.2 (qC, C-10), 39.7 (CH$_2$, C-2), 43.5 (CH$_2$, C-16), 36.5 (CH, C-8), 34.1 (CH, C-9), 28.1 (CH$_2$, C-23), 25.8 (CH$_2$, C-7), 25.5 (CH$_2$, C-12), 21.5 (CH$_2$, C-11), 21.4 (CH$_3$, 15-OAc), 21.1 (CH$_3$, 18-OAc), 20.1 (CH$_3$, C-19), 20.1 (CH$_3$, C-21), 11.9 (CH$_3$, C-27); positive HRESIMS m/z 603.2792 [M+H]$^+$ (calcd for C$_{32}$H$_{43}$O$_{11}$, 603.2805).

Example 13

This example demonstrates the extraction and isolation of withanolide E (9) and 4β-hydroxywithanolide E from five-month old aeroponically cultivated P. peruviana.

Dried and powdered aerial part of P. peruviana (200 g) was extracted with 3 L of 60% aqueous MeOH in an ultrasonic bath at 25° C. for 1 h, filtered. The residue plant material was added 1.5 L of 60% aqueous MeOH and was extracted processed again as described above. The combined 60% aq. MeOH filtrate was loaded to a 500 g Diaion® HP-20SS column to adsorb the withanolides. The column was washed with 1 L of 60% aqueous MeOH, and then the withanolides was eluted out with 1 L of MeOH. The eluted MeOH was concentrated it vacuo to give the crude withanolide extract (4.4 g). The crude extract was subjected to a 80 g of BakerBond™ C$_{18}$ (40μ) open column chromatography. Washed the column with 500 mL of 60% and 70% aq. MeOH each, and collected the fractions according to their TLC traces. The crude 4β-hydroxywithanolide E (800 mg) and crude withanolide E (950 mg) were obtained from 60% aq. MeOH and 70% aq. MeOH respectively. Further purification or these two compounds were achieved by repeated chromatographies on an 80 g SiO$_2$ (25-40μ) column eluted with EtOAc and 95:5 CH$_2$Cl$_2$-MeOH (v/v) separately. The pure withanolide E (500 mg) and pure 4β-hydroxywithanolide E (450 mg) were isolated as off-white amorphous powder.

(9)

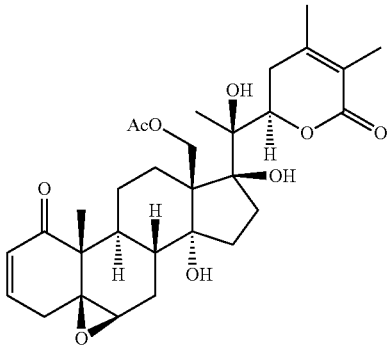

Withanolide E $^1$H NMR (CDCl$_3$, 400 MHz): δ 6.81 (1H, ddd, J=10.0, 6.4, 2.8 Hz, H-3), 6.02 (1H, dd, J=10.0, 2.8 Hz, H-2), 4.89 (1H, dd, J=11.6, 5.2 Hz, H-22), 3.18 (1H, s, H-6α), 1.94 (3H, s, H-28), 1.88 (3H, s, H-27), 1.41 (3H, s, H-21), 1.24 (3H, s, H-19), 1.09 (3H, s, H-18); $^{13}$C NMR (CDCl$_3$, 100 MHz): δ 202.9 (qC, C-1), 165.9 (qC, C-26), 150.7 (qC, C-24), 143.6 (CH, C-3), 129.8 (CH, C-2), 121.4 (qC, C-25), 87.7 (qC, C-17), 81.9 (qC, C-14), 79.6 (CH, C-22), 79.0 (qC, C-20), 64.1 (CH, C-6), 62.1 (qC, C-5), 54.5 (qC, C-13), 48.5 (qC, C-10), 37.8 (CH$_2$, C-16), 36.8 (CH, C-9), 34.2 (CH$_2$, C-12), 34.1 (CH, C-8), 32.4 (CH$_2$, C-23), 32.8 (CH$_2$, C-4), 30.0 (CH$_2$, C-15), 26.2 (CH$_2$, C-7), 22.7 (CH$_2$, C-11), 20.6 (CH$_3$, C-18), 20.5 (CH$_3$, C-28), 19.6 (CH$_3$, C-21), 14.5 (CH$_3$, C-19), 12.3 (CH$_3$, C-27).

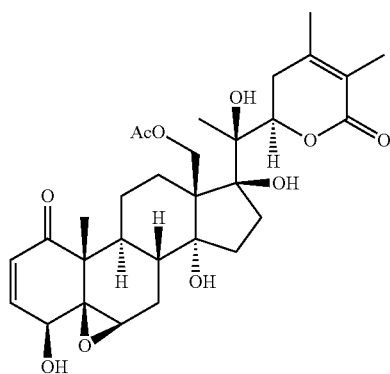

4β–Hydroxywithanolide E $^1$H NMR (CDCl$_3$, 400 MHz), δ 6.91 (1H, dd, J=10.4, 6.4 Hz, H-3), 6.21 (1H, d, J=10.4, Hz, H-2), 4.85 (1H, dd, J=11.6, 5.2 Hz, H-22), 3.72 (1H, d, J=6.4 Hz, H-4α), 3.27 (1H, brs, H-6α), 1.93 (3H, s, H-28), 1.87 (3H, s, H-27), 1.40 (3H, s, H-21), 1.40 (3H, s, H-19), 1.06 (3H, s, C-18); $^{13}$C NMR (CDCl$_3$, 100 MHz): δ 201.8 (qC, C-1), 166.0 (qC, C-26), 150.7 (qC, C-24), 141.4 (CH, C-3), 133.0 (CH, C-2), 121.4 (qC, C-25), 87.6 (qC, C-17), 81.8 (qC, C-14), 79.7 (CH, C-22), 79.0 (qC, C-20), 70.2 (CH, C-4), 64.1 (qC, C-5), 62.8 (CH, C-6), 54.5 (qC, C-13), 47.8 (qC, C-10), 37.8 (CH$_2$, C-16) 36.6 (CH, C-9), 34.2 (CH$_2$, C-23), 34.1 (CH, C-8), 32.3 (CH$_2$, C-15), 29.6 (CH$_2$, C-12), 25.8 (CH$_2$, C-7), 21.3 (CH$_2$, C-11), 20.6 (CH$_3$, C-28), 20.2 (CH$_3$, C-18), 19.6 (CH$_3$, C-21), 16.6 (CH$_3$, C-19), 12.3 (CH$_3$, C-27).

Example 14

This example demonstrates a chemical conversion of physachenolide D to physachenolide C (1).

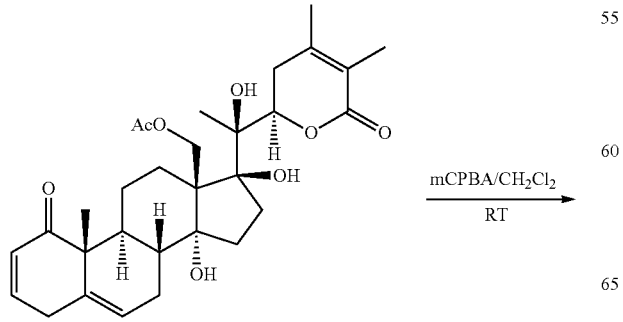

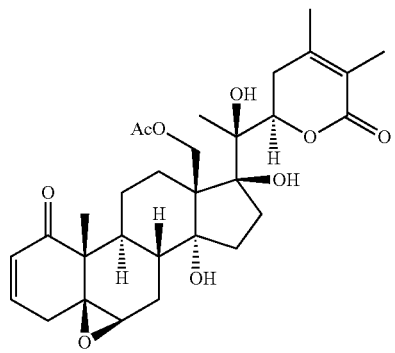

To a stirred solution of physachenolide D (10.0 mg) in CHCl$_3$ (2.0 mL) was added m-chloroperbenzoic acid (10.0 mg) and the reaction mixture was stirred at 25° C. After 2 h (TLC control), the reaction mixture was partitioned between CHCl$_3$ (10.0 mL) and water (20.0 mL). The CHCl$_3$ layer was washed with water (20.0 mL), dried (Na$_2$SO$_4$), and was subjected to purification by HPLC (RP C$_{18}$; 60% aq. MeOH, 3.0 mL/min, UV detection at 230 nm) to provide physachenolide C (5.8 mg, 57%) (t$_R$=23.4 min).

Example 15

This example demonstrates a synthesis of 4α-hydroxywithanolide E (4) from 4β-hydroxywithanolide E.

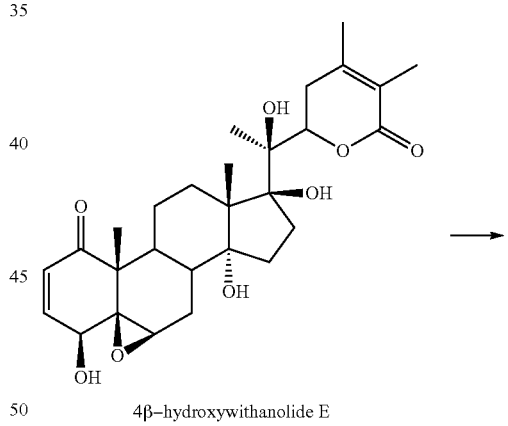

4β–hydroxywithanolide E

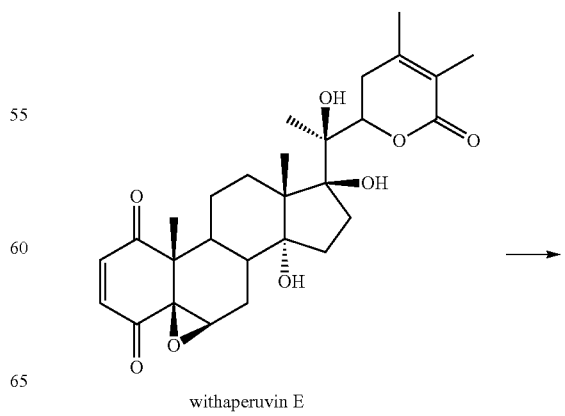

withaperuvin E

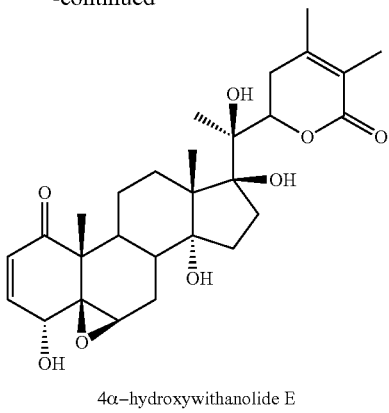

4α-hydroxywithanolide E

Withaperuvin E (3) was prepared by manganese dioxide oxidation of 4β-hydroxywithanolide E (7) as described in the literature (Bagchi, et al., *Phytochemistry* (1984) 23, 853-855). Briefly, to a solution 4β-hydroxywithanolide E (10.0 mg) in chloroform/ethyl acetate (1:1, 3.0 mL) was added activated manganese (IV) oxide ($MnO_2$, Sigma-Aldrich, 60.0 mg) and stirred 25° C. After 6 hours, the reaction mixture was passed through a short column of silica gel (1.0 g) using 6% methanol in dichloromethane as eluant to give withaperuvin E (3) (8.1 mg, 81% yield).

To stirred solution of withaperuvin E (3) (4.0 mg) in methanol (1.0 mL) was added $CeCl_3.7H_2O$ (30.0 mg). The reaction mixture was then kept in an ice bath and stirred for 5 minutes. To this mixture was added $NaBH_4$ (ca 0.5 mg) and stirred at 0° C. After 5 minutes, small ice cube was added to the reaction mixture. Methanol was evaporated under reduced pressure and extracted with ethyl acetate (3×5 mL). Combined ethyl acetate layer was washed with brine, dried over anhydrous $Na_2SO_4$ and evaporated under reduced pressure. Residue was then chromatographed over a column of silica gel (500.0 mg) made up in dichloromethane and eluted with dichloromethane containing increasing amounts of methanol. Fractions eluted with 6% methanol in dichloromethane were combined and evaporated under reduced pressure and the crude product was further purified by reversed phase HPLC on a Phenomenex, Luna, $C_{18}$ RP column (250×10 mm) using methanol/water (70:30) as eluant to give 4α-hydroxywithanolide E (4) (3.0 mg, 75% yield, $t_R$=15 minutes) as a white solid; mp 198-200° C.; $[α]^{25}_D$+65 (c 0.2, $CHCl_3$); $^1$H NMR (400 MHz, $CDCl_3$) δ: 6.78 (dd, J=10.1, 1.7 Hz, 1H, H-3), 5.99 (dd, J=10.1, 2.6 Hz, 1H, H-2), 4.84 (dd, J=11.2, 5.6, Hz, 1H, H-22), 4.65 (brs, 1H, H-4), 3.71 (brt, J=1.9 Hz, 1H, H-6), 2.69 (ddd, J=15.1, 11.0, 8.0 Hz, 1H, Ha-16), 2.52-2.42 (m, 2H, $H_2$-23), 2.24 (dt, J=12.5, 4.9 Hz, 1H, Ha-12), 2.13 (d, J=2.8 Hz, 1H, $D_2O$ exchangeable, OH-4), 1.98 (m, 2H, $H_2$-7), 1.91 (s, 3H, $H_3$-28), 1.85 (s, 3H, $H_3$-27), 1.83 (m, 2H, H-8, Ha-11), 1.69-1.53 (m, 4H, H-9, Hb-11, $H_2$-15), 1.42 (dd, J=15.1, 8.3 Hz, 1H, Hb-16), 1.39 (s, 3H, $H_3$-21), 1.27 (brd, 1H, Hb-12), 1.20 (s, 3H, $H_3$-19), 1.06 (s, 3H, $H_3$-18); $^{13}$C NMR (100 MHz, $CDCl_3$) δ: 200.6 (C, C-1), 165.7 (C, C-26), 150.5 (C, C-24), 146.9 (CH, C-3), 128.7 (CH, C-2), 121.5 (C, C-25), 87.6 (C, C-17), 81.8 (C, C-14), 79.5 (CH, C-22), 79.1 (C, C-20), 65.6 (C, C-5), 64.7 (CH, C-4), 56.2 (CH, C-6), 54.5 (C, C-13), 47.5 (C, C-10), 37.9 ($CH_2$, C-16), 37.8 (CH, C-9), 34.2 ($CH_2$, C-23), 34.1 (CH, C-8), 32.3 ($CH_2$, C-15), 29.7 ($CH_2$, C-12), 25.6 ($CH_2$, C-7), 21.6 ($CH_2$, C-11), 20.6 ($CH_3$, C-28), 20.4 ($CH_3$, C-18), 19.7 ($CH_3$, C-21), 13.2 ($CH_3$, C-19), 12.4 ($CH_3$, C-27); HRESIMS m/z 525.2463 $[M+Na]^+$ (calcd for $C_{28}H_{38}NaO_8$ 525.2463).

Example 16

This example demonstrates a synthesis of 4α-acetoxywithanolide E (5) from 4α-hydroxywithanolide E.

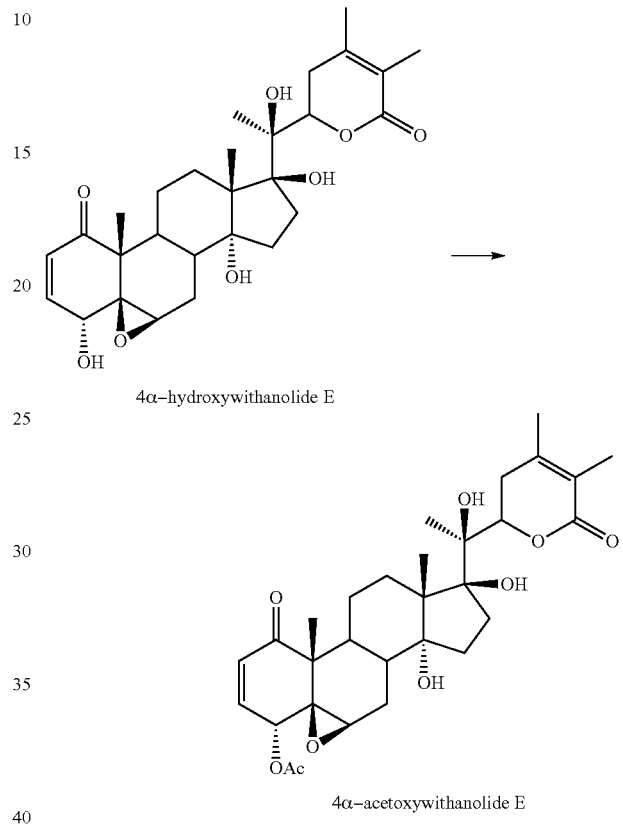

4α-hydroxywithanolide E

4α-acetoxywithanolide E

To a solution of 4α-hydroxywithanolide E (4) (1.2 mg) in pyridine (0.05 mL) was added acetic anhydride (0.1 mL) and stirred at 25° C. After 16 hours, ethanol (10.0 mL) was added to the reaction mixture. The volatiles were evaporated under reduced pressure, and the residue was purified by reversed phase HPLC on a Phenomenex, Luna, $C_{18}$ RP column (250×10 mm) using methanol/water (75:25) as eluant to give 4α-acetoxywithanolide E (5) (1.2 mg, 92% yield, $t_R$=9.5 minutes) as a white solid; mp 186-188° C.; $[α]^{25}_D$+100 (c 0.1, $CHCl_3$); $^1$H NMR (400 MHz, $CDCl_3$) δ: 6.62 (dd, J=10.3, 1.9 Hz, 1H, H-3), 6.05 (dd, J=10.3, 2.8 Hz, 1H, H-2), 5.85 (dd, J=2.8, 1.9 Hz, 1H, H-4), 4.85 (dd, J=11.4, 5.1, Hz, 1H, H-22), 3.58 (brs, 1H, H-6), 2.69 (dt, J=12.8, 10.6 Hz, 1H, Ha-16), 2.54-2.42 (m, 2H, $H_2$-23), 2.25 (dt, J=13.0, 5.0 Hz, 1H, Ha-12), 2.09 (s, 3H, OAc), 2.03-1.93 (m, 2H), 1.92 (s, 3H, $H_3$-28), 1.90-1.82 (m, 2H), 1.86 (s, 3H, $H_3$-27), 1.73 (m, 1H), 1.67-1.53 (m, 3H), 1.41 (dd, 15.1, 8.3 Hz, 1H, Hb-16), 1.39 (s, 3H, $H_3$-21), 1.28 (m, 1H, Hb-12), 1.27 (s, 3H, $H_3$-19), 1.06 (s, 3H, $H_3$-18); $^{13}$C NMR (100 MHz, $CDCl_3$) δ: 200.3 (C, C-1), 169.8 (C, OAc), 165.7 (C, C-26), 150.3 (C, C-24), 144.4 (CH, C-3), 129.6 (CH, C-2), 121.5 (C, C-25), 87.6 (C, C-17), 81.7 (C, C-14), 79.4 (CH, C-22), 79.1 (C, C-20), 65.6 (C, C-53, 63.2 (CH, C-4), 56.5 (CH, C-6), 54.5 (C, C-13), 47.9 (C, C-10), 37.8 ($CH_2$, C-16), 37.7 (CH, C-9), 34.3 ($CH_2$, C-23), 34.0 (CH, C-8), 32.4 ($CH_2$, C-15), 29.8 ($CH_2$, C-12), 25.5 ($CH_2$, C-7), 21.9

(CH$_2$, C-11), 20.8 (CH$_3$, C-28), 20.6 (CH$_3$, C-18), 20.4 (CH$_3$, OAc), 19.7 (CH$_3$, C-21), 13.9 (CH$_3$, C-19), 12.4 (CH$_3$, C-27); HRESIMS m/z 567.2565 [M+Na]$^+$ (calcd for C$_{30}$H$_{40}$NaO$_9$ 567.2563).

Example 17

This example demonstrates a synthesis of withaperuvin M (6) from withaperuvin E.

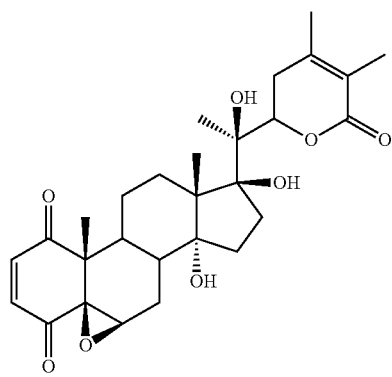
withaperuvin E

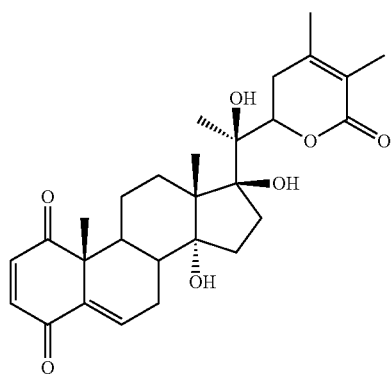
withaperuvin M

To a stirred solution of triphenylphosphene (1.6 mg) and iodine (1.9 mg) in anhydrous dichloromethane (0.05 mL) at 0° C. was added a solution of withaperuvin E (3) (2.5 mg) in anhydrous dichloromethane (0.15 mL). Ice bath was removed and the reaction mixture was stirred at 25° C. After 1 hour, reaction mixture was diluted with dichloromethane (10 mL), washed with 10% aqueous Na$_2$S$_2$O$_3$ solution (2×5 mL), brine (2×5 mL), dried over anhydrous Na$_2$SO$_4$ and evaporated under reduced pressure to give crude product mixture. This mixture was separated by reversed phase HPLC on a Phenomenex, Luna, C$_{18}$ RP column (250×10 mm) using methanol/water (72.5:27.5) as eluant to give withaperuvin M (6) (1.5 mg, 62% yield, t$_R$=11.5 minutes) as a pale yellow solid; mp 176-178° C.; [α]$^{25}_D$+115 (c 0.8, CHCl$_3$); $^1$H and $^{13}$C NMR data were consistent with those reported in the literature (Fang et al., *Steroids* (2012), 77, 36-44).

Example 18

This example demonstrates a synthesis of 4β-imidazolyl-carbonyloxywithanolide E from 4β-hydroxywithanolide E.

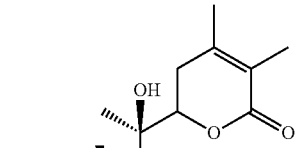
4β-hydroxywithanolide E

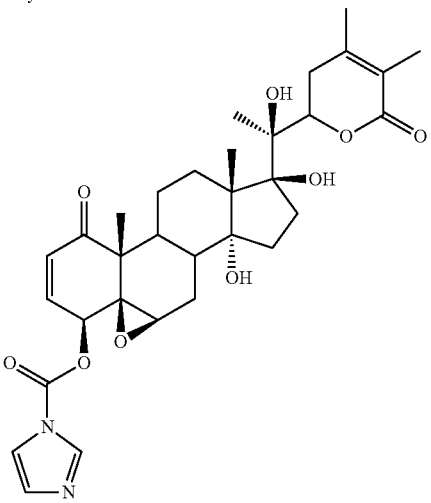
4β-imidazolylcarbonyloxywithanolide E

To a solution of 4β-hydroxywithanolide E (7) (10.0 mg) in anhydrous dichloromethane (1.0 mL) was added 1,1'-carbonyldiimidazole (8.0 mg) and stirred at 25° C. After 1 hour reaction mixture was passed through a short column of silica gel (0.5 mg) using ethyl acetate as eluant to give 4β-imidazolylcarbonyloxywithanolide E (11) (8.1 mg, 68%) as a white solid; mp dec.>210° C.; [α]$^{25}_D$+108 (c 0.5, CHCl$_3$); $^1$H NMR (400 MHz, CDCl$_3$) δ: 8.04 (s, 1H, N—CH═N), 7.31 (t, J=1.6 Hz, 1H, N—CH), 7.04 (m, 1H, N—CH), 7.04 (dd, J=9.8, 6.1 Hz. 1H, H-3), 6.37 (d, J=9.8 Hz, 1H, H-2), 4.89 (d, J=6.1 Hz, 1H, H-4), 4.83 (dd, J=11.5, 5.5 Hz, 1H, H-22), 3.37 (t, J=2.0 Hz, 1H, H-6), 2.69 (ddd, J=15.0, 11.0, 8.5 Hz, 1H, Ha-16), 2.54-2.42 (m, 2H, H$_2$-23), 2.24 (dt, J=11.8, 5.7 Hz, 1H, Ha-12), 2.13-2.05 (m, 2H, H$_2$-7), 1.92 (s, 3H, H$_3$-28), 1.86 (s, 3H, H$_3$-27), 1.81 (dd, J=11.0, 6.3 Hz, 1H, H-8), 1.70-1.52 (m, 5H, H-9, H$_2$-11, H$_2$-15), 1.43 (m, 1H, Hb-16), 1.42 (s, 3H, H$_3$-19), 1.39 (s, 3H, H$_3$-21), 1.29 (brd, 1H, Hb-12), 1.05 (s, 3H, H$_3$-18); $^{13}$C NMR (100 MHz, CDCl$_3$) δ: 200.1 (C, C-1), 165.7 (C, C-26), 150.6 (C, C-24), 147.9 (C, NC═O), 137.1 (CH, N—CH═N), 136.9 (CH, C-3), 136.0 (CH, C-2), 131.0 (CH, N—CH), 121.5 (C, C-25), 117.1 (CH, N—CH), 87.6 (C, C-17), 81.6 (C, C-14), 79.4 (CH, C-22), 79.1 (C, C-20), 76.1 (CH, C-4), 61.5 (CH, C-6), 60.9 (C, C-5), 54.5 (C, C-13), 48.0 (C, C-10), 37.8 (CH$_2$, C-16), 36.8 (CH, C-9), 34.3 (CH$_2$, C-23), 33.9 (CH, C-8), 32.3 (CH$_2$, C-15), 29.4 (CH$_2$, C-12), 25.6 (CH$_2$, C-7), 20.9 (CH$_2$, C-11), 20.7 (CH$_3$, C-28), 20.2 (CH$_3$, C-18), 19.7 (CH$_3$, C-21), 15.4 (CH$_3$, C-19), 12.4 (CH$_3$, C-27); APCI-MS (+) mode m/z 597 [M+1]$^+$; APCI-MS (−) mode m/z 595 [M−1]$^-$.

Example 19

This example demonstrates a synthesis of a biotinylated derivative of 4β-hydroxywithanolide E from 4β-imidazolylcarbonyloxywithanolide E.

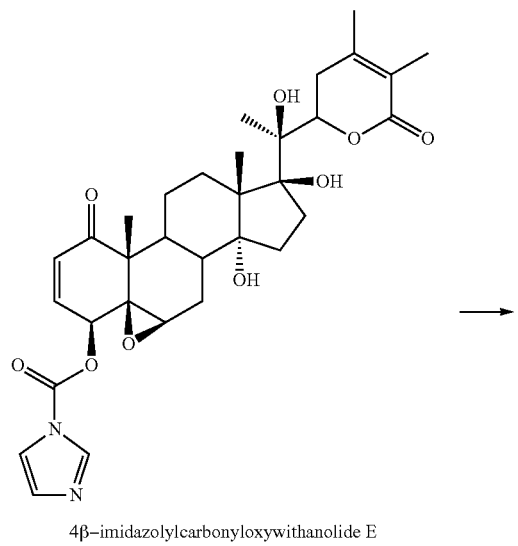

4β–imidazolylcarbonyloxywithanolide E

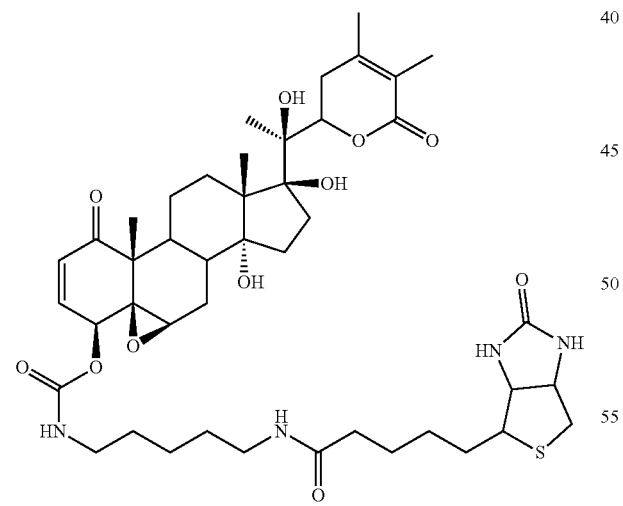

To a solution of 4β-imidazolylcarbonyloxywithanolide E (11) (8.0 mg) in anhydrous N,N-dimethylformamide (0.5 mL) was added EZ-Link 5-(Biotinamido)pentylamine (8.0 mg) and stirred at 25° C. After 6 hours, reaction mixture was diluted with ethyl acetate (15 mL), washed with brine (3×5 mL), dried over anhydrous Na$_2$SO$_4$ and evaporated under reduced pressure to give crude products mixture. This was chromatographed over column of silica gel (0.5 g) made up in dichloromethane and eluted with dichloromethane containing increasing amounts of methanol. Fractions eluted with 20% methanol in dichloromethane were combined, evaporated under reduced pressure and the residue was further purified by reversed phase HPLC on a Phenomenex, Luna, C$_{18}$ RP column (250×10 mm) using methanol/water (67.5:32.5) as eluant to give biotinylated derivative of 4β-hydroxywithanolide E (8) (4.2 mg, 37% yield, t$_R$=9.5 minutes) as a white solid; mp dec.>240° C.; [α]$^{25}$$_D$+136 (c 0.6, MeOH); $^1$H NMR (400 MHz, CDCl$_3$+CD$_3$OD); 6.98 (dd, J=9.7, 6.0 Hz, 1H, H-3), 6.18 (d, J=9.7 Hz, 1H, H-2), 4.76 (dd, J=12.5, 4.6 Hz, 1H, H-22), 4.50 (d, J=6.0 Hz, 1H, H-4), 4.44 (dd, J=7.8, 5.0 Hz, 1H), 4.24 (dd, J=7.8, 4.5 Hz, 1H), 3.24 (brs, 1H, H-6), 3.14-3.02 (m, 5H), 2.85 (dd, J=12.8, 4.8 Hz, 1H), 2.66 (d, J=12.8 Hz, 1H), 2.58 (m, 1H, Ha-16), 2.50-2.41 (2H, m, H$_2$-23), 2.18 (m, 1H, Ha-12), 2.12 (m, 2H), 1.96-1.92 (m, 2H, H$_2$-7), 1.87 (s, 3H, H$_3$-28), 1.79 (s, 3H, H$_3$-27), 1.73 (m, 1H, H-8), 1.49 (m, 1H, Ha-11), 1.65-1.55 (m, 6H), 1.51 (m, 1H, H-9), 1.48-1.35 (m, 10H), 1.30 (s, 6H, H$_3$-19, H$_3$-21), 1.23 (m, 2H), 1.18 (m, 1H, Hb-12), 0.98 (s, 3H, H$_3$-18); $^{13}$C NMR (100 MHz, CDCl$_3$+CD$_3$OD) δ: 201.7 (C, C-1), 173.5 (C), 167.2 (C, C-26), 163.8 (C), 155.7 (C), 151.5 (C, C-24), 140.4 (CH, C-3), 133.9 (CH, C-2), 121.2 (C, C-25), 87.4 (C, C-17), 81.7 (C, C-14), 80.6 (CH, C-22), 78.6 (C, C-20), 72.4 (CH, C-4), 61.8 (CH, NC), 61.4 (C, C-5), 61.1 (CH, C-6), 60.0 (CH, NC), 55.5 (CH, S—CH), 54.3 (C, C-13), 48.2 (C, C-10), 40.4 (CH$_2$, S—CH$_2$), 39.1 (CH$_2$), 37.3 (CH$_2$, C-16), 36.8 (CH, C-9), 35.7 (CH$_2$), 34.3 (CH$_2$, C-23), 33.9 (CH, C-8), 32.2 (CH$_2$, C-15), 29.5 (CH$_2$, C-12), 29.2 (CH$_2$), 28.8 (CH$_2$), 28.2 (CH$_2$), 28.0 (CH$_2$), 25.7 (CH$_2$, C-7), 25.4 (CH$_2$), 23.8 (CH$_2$), 20.9 (CH$_2$, C-11), 20.6 (CH$_3$, C-28), 20.1 (CH$_3$, C-18), 19.0 (CH$_3$, C-21), 15.1 (CH$_3$, C-19), 12.1 (CH$_3$, C-27); APCI-MS (+) mode m/z 857 [M+1]$^+$, 839 [M+1−H$_2$O]$^+$; APCI-MS (−) mode m/z 855 [M−1]$^-$.

Example 20

This example demonstrates a synthesis of a biotinylated derivative of 4α-hydroxywithanolide E from 4α-hydroxywithanolide E.

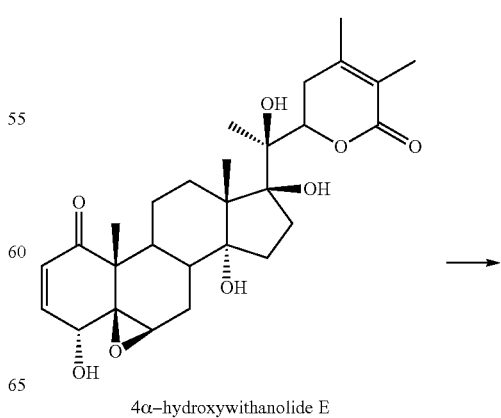

4α–hydroxywithanolide E

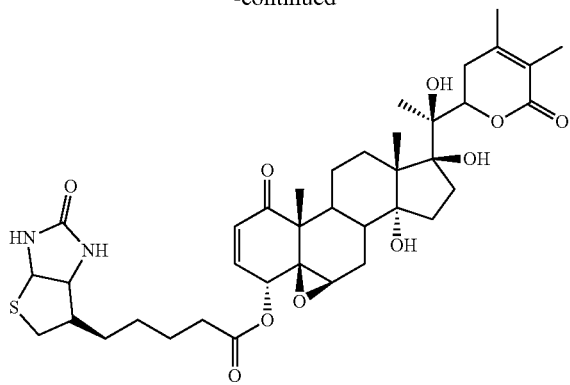

To a solution of 4α-hydroxywithanolide E (4) (4.4 mg) in N,N-dimethylformamide (0.5 mL) was added EZ Link PFP biotin (10 mg) and 4-pyrilidinopyridine (2.0 mg) and stirred at 60° C. After 16 hours reaction mixture was diluted with ethyl acetate (10.0 mL), washed with brine (3×5 mL), dried over anhydrous $Na_2SO_4$ and evaporated under reduced pressure, Crude product mixture was chromatographed over a column of silica gel (0.5 g) made up in dichloromethane and eluted with 2% methanol in dichloromethane followed by 4% methanol in dichloromethane. Fractions eluted with 4% methanol in dichloromethane were combined and evaporated under reduced pressure and the residue was further purified by reversed phase HPLC on a Phenomenex, Luna, $C_{18}$ RP column (250×10 mm) using methanol/water (70:30) as eluant to give biotinylated derivative of 4α-hydroxywithanolide E (12) (2.3 mg, 76% yield, $t_R$=14 minutes) as a white solid; mp 194-196° C.; $[\alpha]^{25}_D$+76 (c 0.2, $CHCl_3$); $^1$H NMR (400 MHz, $CDCl_3$) δ: 6.62 (dd, J=9.9, 1.6 Hz, 1H, H-3), 6.04 (dd, J=9.9, 2.4 Hz, 1H, H-2), 5.87 (dd, J=2.4, 1.6 Hz, 1H, H-4), 5.43 (brs, 1H, NH), 5.25 (brs, 1H, NH), 4.83 (dd, J=11.6, 5.3 Hz, 1H, H-22), 4.51 (brs, 1H), 4.29 (brs, 1H), 3.55 (brs, 1H, H-6), 3.14 (m, 1H), 2.90 (dd, J=12.2, 4.7, 1H), 2.74 (d, J=12.2, 1H), 2.66 (m, 1H, Ha-16), 2.54-2.42 (m, 2H, $H_2$-23), 2.36 (t, J=6.9 Hz, 2H), 2.24 (m, 1H, Ha-12), 1.95 (m, 2H), 1.92 (s, 3H, $H_3$-28), 1.88 (m, 1H, Ha-11), 1.85 (s, 3H, $H_3$-27), 1.84 (m, 1H, H-8), 1.73 (m, 1H, H-9), 1.68 (m, 3H), 1.62-1.54 (m, 3H, Hb-11, $H_2$-15), 1.45 (m, 1H), 1.42 (m, Hb-16), 1.38 (s, 3H, $H_3$-21), 1.27 (s, 3H, $H_3$-19), 1.24 (m, 1H, Hb-12), 1.06 (s, 3H, $H_3$-18); $^{13}$C NMR (100 MHz, $CDCl_3$) δ: 200.3 (C, C-1), 172.4 (C, OC=O), 156.2 (C, C-26), 150.7 (C, C-24), 144.4 (CH, C-3), 129.7 (CH, C-2), 121.4 (C, C-25), 87.8 (C, C-17), 81.8 (C, C-14), 79.9 (CH, C-22), 78.9 (C, C-20), 65.5 (CH, C-4), 63.5 (C, C-5), 61.9 (CH, NC), 60.2 (CH, NC), 56.5 (CH, C-6), 55.3 (CH, SCH), 54.5 (C, C-13), 47.9 (C, C-10), 40.5 ($CH_2$, $SCH_2$), 37.8 (CH and $CH_2$, C-9 and C-16), 34.3 ($CH_2$, C-23), 34.0 (CH, C-8), 33.8 ($CH_2$), 32.4 ($CH_2$, C-15), 29.8 ($CH_2$, C-12), 28.2 ($CH_2$), 25.6 ($CH_2$, C-7), 24.7 ($CH_2$), 22.6 ($CH_2$), 21.9 ($CH_2$, C-11), 20.6 ($CH_3$, C-28), 20.4 ($CH_3$, C-18), 19.5 ($CH_3$, C-21), 13.9 ($CH_3$, C-19), 12.4 ($CH_3$, C-27) APCI-MS (+) mode m/z 729 $[M+1]^+$, 711 $[M+1-H_2O]^+$; APCI-MS (−) mode m/z 727 $[M-1]^-$.

Example 21

To assess the effects of pan caspase inhibitor ZVAD, SKMEL28 melanoma cells were treated with compounds 9 and 1 for 16-18 h. Subsequently, ZVAD-FMK (40 μM) or DMSO was added for 2 h followed by 20-24 h incubation in the presence or absence of poly IC. Cell viability was assessed by addition of MTS during the last four hours of poly IC treatment.

The growth inhibition as a function of poly IC concentration at 1000 nM concentrations of compounds 9 and 1 was determined, and the results shown in FIGS. 10A and 10B, respectively. The reduction in cell number by poly IC in combination with compounds 9 and 1 was due to apoptotic cell death, since it was completely blocked by the caspase inhibitor ZVAD-FMK.

Example 22

This example demonstrates that intratumoral delivery of compound 1 decreases tumor growth in a xenograft model of human M14 melanoma in athymic nude mice.

Mice (nude athymic, female, 6-8-week old, n=5), were implanted subcutaneously with 0.2 ml of M14 melanoma cells (1×10$^6$/mouse) into the right flank. When the tumor reached approximately 75 mm$^3$ (4-5 weeks after initial inoculation), they were treated either vehicle control (33% Trappsol with DMSO at a ratio 7:1), or with compound 9 or compound 1 intratumorally at a dose of 20 mg/Kg of body weight, once per week for four weeks. The appearance and growth of tumors were monitored twice every week. The greatest longitudinal diameter (length) and the greatest transverse diameter (width) of a palpable tumor were measured to the nearest 0.1 mm using a caliper. Tumor volume (mm$^3$) was calculated by the ellipsoidal formula Tumor volume=(length×width)/2. Mice were euthanized once control tumors reached the termination point, as indicated by compromised health or tumor end point. As observed in FIG. 11, a significant reduction in tumor growth and volume was observed in mice receiving compound 1 as compared to control or compound 9. No significant decrease in tumor burden was observed in compound 9 treated groups as compared to vehicle control. Two way ANOVA with Dunnet's multiple comparison test was performed. (****P<0.0001 versus control). Decrease in tumor burden was accompanied by massive tumor destruction and scabbing at the tumor site. It is likely that compound 1 apart from sensitizing tumor cells to death ligands also induces production of inflammatory cytokines locally in the tumor microenvironment which may further potentiate tumor apoptosis and its subsequent regression.

Example 23

This example demonstrates that combinatorial treatment with compound 9 and poly IC causes tumor regression in a xenograft model of human M14 melanoma in athymic nude mice.

Mice (nude athymic, female, 6-8-week old, n=5), were implanted subcutaneously with 0.2 ml of M14 melanoma cells (1×10$^6$/mouse) into the right flank. When the tumor reached approximately 75 mm$^3$ (4-5 weeks after initial inoculation), they were treated either vehicle control (33% Trappsol with DMSO at a ratio 7:1), or with compound 9 at a dose of 20 mg/Kg of body weight. The following day mice were treated with either saline or Poly IC (50 ug/mouse) intraperitoneally. This treatment regimen was followed for four weeks. The appearance and growth of tumors were monitored twice every week. The greatest longitudinal diameter (length) and the greatest transverse diameter (width) of a palpable tumor were measured to the nearest 0.1 mm using a caliper. Tumor volume (mm) was calculated by the ellipsoidal formula Tumor volume=length×width)/2.

Mice were euthanized once control tumors reached the termination point, as indicated by compromised health or tumor end point. As observed in FIG. 12, a significant reduction in tumor growth and volume was observed in mice receiving the combination treatment (compound 9+poly IC) as compared to control or compound 9 or poly IC alone. No significant decrease in tumor burden was observed in compound 9-treated groups as compared to vehicle control. Two way ANOVA with Tukey's multiple comparison test was performed. (****P<0.0001 versus control). Decrease in tumor burden was accompanied by massive tumor destruction and scabbing at the tumor site. Compound 9 sensitizes tumor cells to death ligands. However by itself it is not a potent inducer of apoptosis of tumor cells. It is likely that the suboptimal doses of poly IC is able to activate signaling pathways leading to activation of caspases, NK cells activation, and Interferon (IFN) production culminating in destruction of compound 9 sensitized tumor cells and its subsequent regression.

Example 24

This example provides a comparison of the activities of compound 1 with the Smac mimetics birinapant, GDC-0152, and LCL-161 and with the Bcl-2 antagonists ABT-199 and ABT-737 for sensitization of renal carcinoma and melanoma cells to TRAIL apoptosis.

The results for compound 1 are shown graphically in FIGS. 13A-22A. The results for Smac mimetics birinapant, GDC-0152, and LCL-161 are shown graphically in FIGS. 13B-22B. The results for Bcl-2 antagonists ART-199 and ABT-737 are shown graphically in FIGS. 13C-22C. FIGS. 13A-22A, 13B-22B, and 13C-22C depict the percentage decrease in cell number as a function of concentration. For FIGS. 13B-22B and 13C-22C, the dose response curve was obtained for one of the listed agents. All of Smac mimetics birinapant, GDC-0152, and LCL-161 and Bcl-2 antagonists ABT-199 and ABT-737 exhibited very similar dose responses in the absence of TRAIL and showed little to no response due to concentration.

As is apparent from the results depicted in FIGS. 13A-17A, 13B-17B, and 13C-17C, compound 1 was a superior sensitizer in the renal carcinoma cell lines than either the Smac mimetics birinapant. GDC-0152, and LCL-161 or the Bcl-2 antagonists ABT-199 and ABT-737 (both of which are currently in clinical trials).

For the melanoma cells, Smac mimetics were the best sensitizer, compound 1 still had significant activity, whereas Bcl-2 antagonists had little activity.

Example 25

This example demonstrates the activities of combinations of compound 1 and Smac mimetics birinapant, GDC-015, and LCL-161 and Bcl-2 antagonists ABT-737 and venetoclax for sensitization of renal carcinoma and melanoma cells to TRAIL apoptosis.

The renal carcinoma cells ACHN and UO-31 at 5000 c/well were incubated with various concentrations of compound 1 and 1000 nM or other compounds with and without TRAIL, The viable cell number was determined using the MTS assay.

The results for ACHN cells are shown graphically in FIGS. 23A and 23B. The results for UO-31 cells are shown graphically in FIGS. 24A and 24B. Data points indicated by A are for compound 1 alone. Data points indicated by B-F are for compound 1 in combination with the corresponding Smac mimetic or Bcl-2 antagonist. The x axis indicates the concentration of compound 1 and the y axis indicates the percent reduction in cell number.

As is apparent from the results depicted in FIGS. 23A and 23B and 24A and 24B, the percentage reduction in cell number exhibited by combinations of compound 1 and the tested Smac mimetics and Bcl-2 antagonists with TRAIL, was significantly greater than exhibited by compound 1 alone or the Smac mimetics and Bcl-2 antagonists alone, demonstrating a synergistic effect in sensitization to TRAIL exhibited by the combination of compound 1 and Smac mimetics or Bcl-2 antagonists.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate, value is incorporated into the specification as if it were individually recited herein. All methods described heroin can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of synergistically enhancing the response of cancer cells in a mammal to treatment with an apoptosis inducing ligand or of inducing apoptosis in cancer cells in a mammal that are resistant to treatment with an apoptosis inducing ligand comprising administering to the mammal a therapeutically effective amount of a compound of the formula:

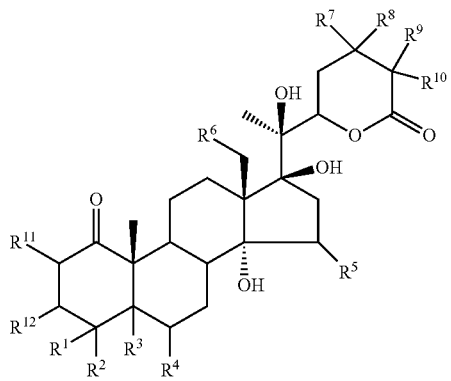

wherein $R^1$ is H and $R^2$ is selected from $C_1$-$C_6$ acyloxy, heteroarylcarbonyloxy, a group of the formula:

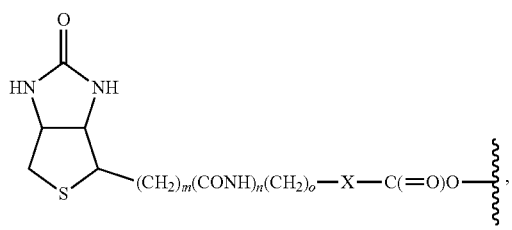

or, $R^1$ and $R^2$ taken together, form =O,

X is NH or is absent, m and o are integers of from 1 to about 10, n is 0 or 1, $R^3$ and $R^4$ are independently OH or $C_1$-$C_6$ alkoxy or, taken together, form a double bond or an epoxy ring, $R^5$ is H or $C_1$-$C_6$ acyloxy, $R^6$ is H, OH, or $C_1$-$C_6$ acyloxy, $R^7$ and $R^9$ are independently $CH_3$ or $CH_2OH$, $R^8$ and $R^{10}$, taken together with the carbon atoms to which they are attached, form a double bond, and $R^{11}$ and $R^{12}$ are both H, $R^{11}$ is H and $R^{12}$ is —$OSO_3H$, $R^{11}$ is H and $R^{12}$ is imidazolyl, or $R^{11}$ and $R^{12}$ taken together with the carbon atoms to which they are attached, form a double bond, and administering an effective amount of an apoptosis-inducing ligand, whereby a synergistic enhancement of the response is obtained or whereby apoptosis is induced in the cancer cells.

2. The method according to claim 1, wherein $R^{11}$ and $R^{12}$, taken together, form a double bond, $R^3$ and $R^4$, taken together, form an epoxy ring, $R^5$ is H, $R^7$ and $R^9$ are $CH_3$, and $R^8$ and $R^{19}$, taken together, form a double bond.

3. The method according to claim 2, wherein $R^1$ is H and $R^2$ is $C_1$-$C_6$ acyloxy.

4. The method according to claim 3, wherein the compound is of the formula:

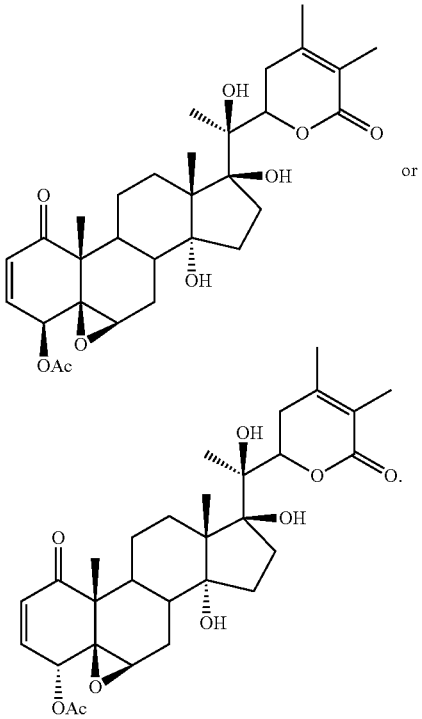

5. The method according to claim 2, wherein the compound is of the formula:

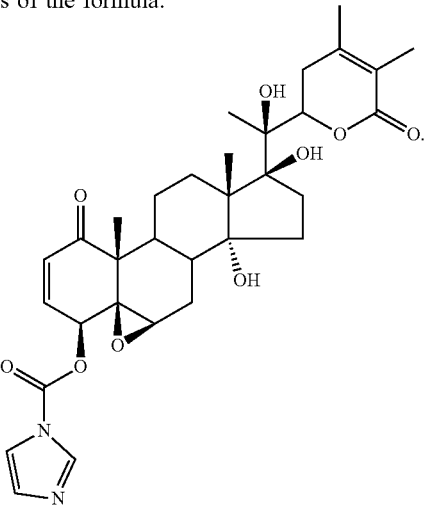

6. The method according to claim 2, wherein $R^1$ is H and $R^2$ is a group of the formula:

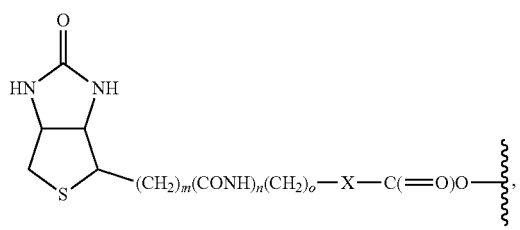

wherein m and o are integers of from 1 to about 10, and n is 0 or 1.

7. The method according to claim 6, wherein the compound is of the formula:

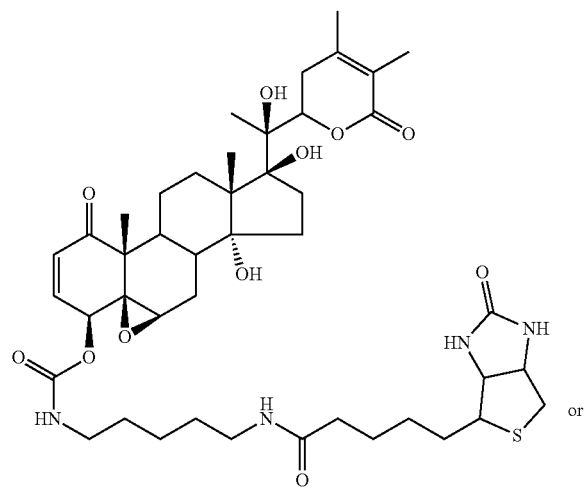 or

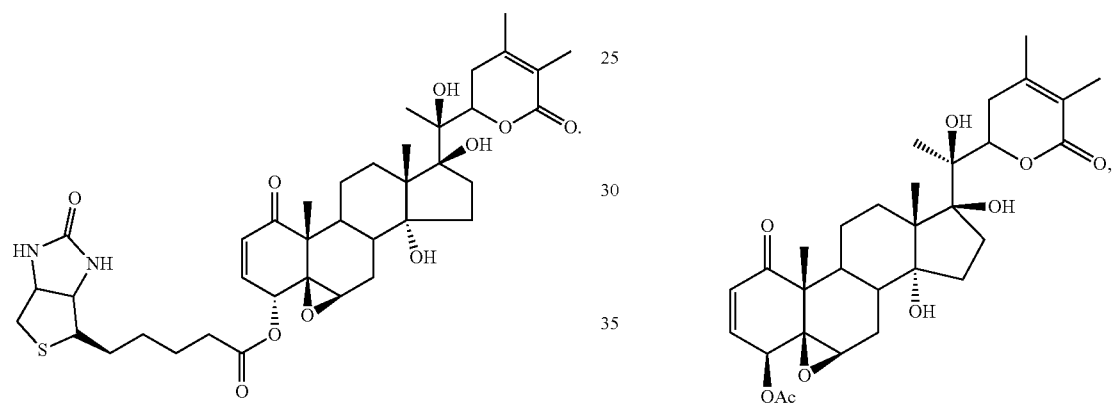

8. The method according to claim 1, wherein the compound is of the formula:

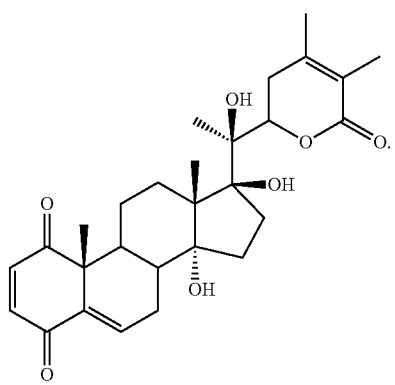 [SMILES: CC1=C(C)C(=O)OC([C@](C)(O)[C@]2(O)CC[C@@]3(O)C4CC=C5C(=O)C=CC(=O)[C@]5(C)C4CC[C@]23C)C1]

9. The method according to claim 1, wherein the cancer cells express a TNF receptor or a toll-like receptor.

10. The method according to claim 1, wherein the apoptosis-inducing ligand is selected from TRAIL, TNF-α, FasL, an anti-DR4 antibody, an anti-DR5 antibody, and poly IC.

11. The method according to claim 1, further comprising administering to the mammal an Smac mimetic which is birinapant, GDC-015, or LCL-161, a Bcl-2 antagonist which is ABT-199, ABT-737, or venetoclax, or a combination thereof.

12. The method according to claim 1, wherein the cancer cells are associated with a cancer selected from glioma, thyroid carcinoma, breast carcinoma, small-cell lung carcinoma, non-small-cell lung carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, skin carcinoma, melanoma, basal cell carcinoma, squamous cell carcinoma, anaplastic large-cell lymphoma, multiple myeloma, leukemia, lymphoma, cervical carcinoma, and mesothelioma, follicular thyroid carcinoma, colorectal cancer, myeloid leukemia, hepatic cancer, hepatocellular carcinoma, cholangiocarcinoma, cervical and ovarian cancer, cancers of glial origin, and combinations thereof.

13. The method according to claim 1, wherein the compound is of the formula:

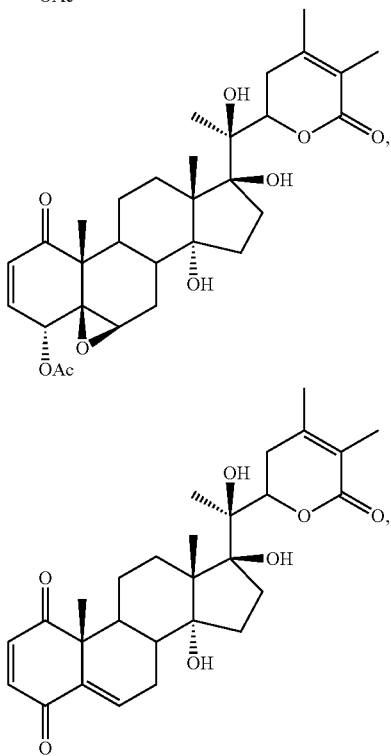

-continued

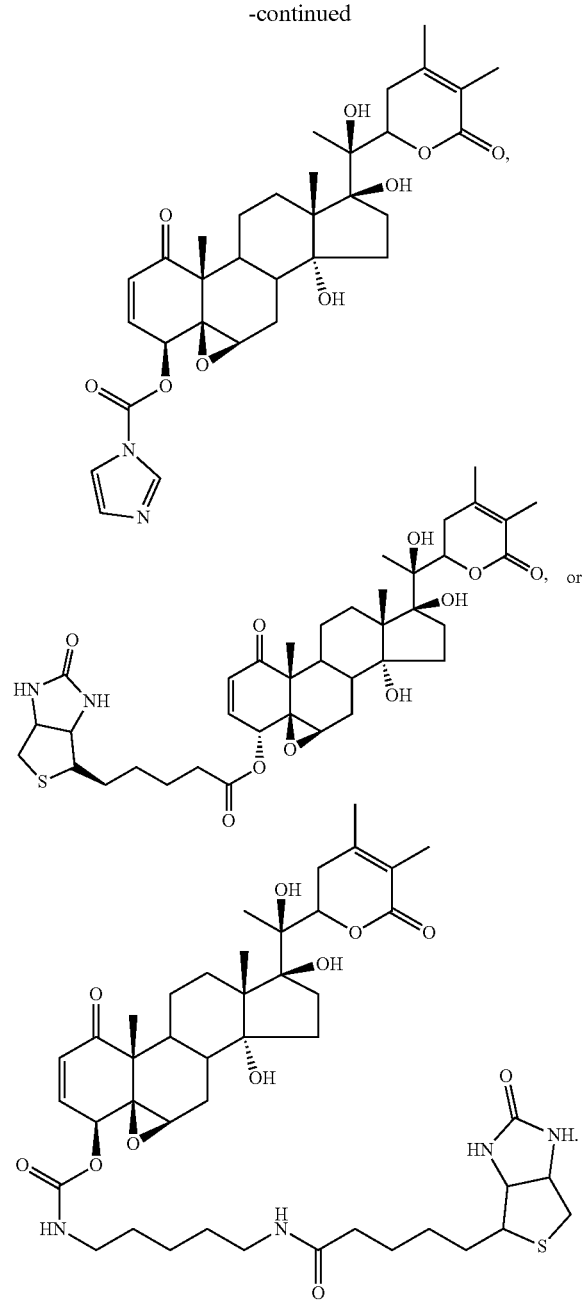

14. A compound of the formula:

wherein $R^1$ is H and $R^2$ is a group of the formula:

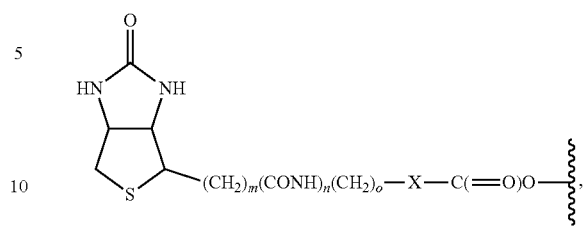

X is NH or is absent,
m and o are integers of from 1 to about 10,
n is 0 or 1,
$R^3$ and $R^4$, taken together, form an epoxy ring,
$R^5$ is H,
$R^6$ is H, OH, or $C_1$-$C_6$ acyloxy,
$R^7$ and $R^9$ are $CH_3$,
$R^8$ and $R^{19}$, taken together with the carbon atoms to which they are attached, form a double bond, and
$R^{11}$ and $R^{12}$ taken together with the carbon atoms to which they are attached, form a double bond.

15. The compound of claim 14, wherein the compound is of the formula:

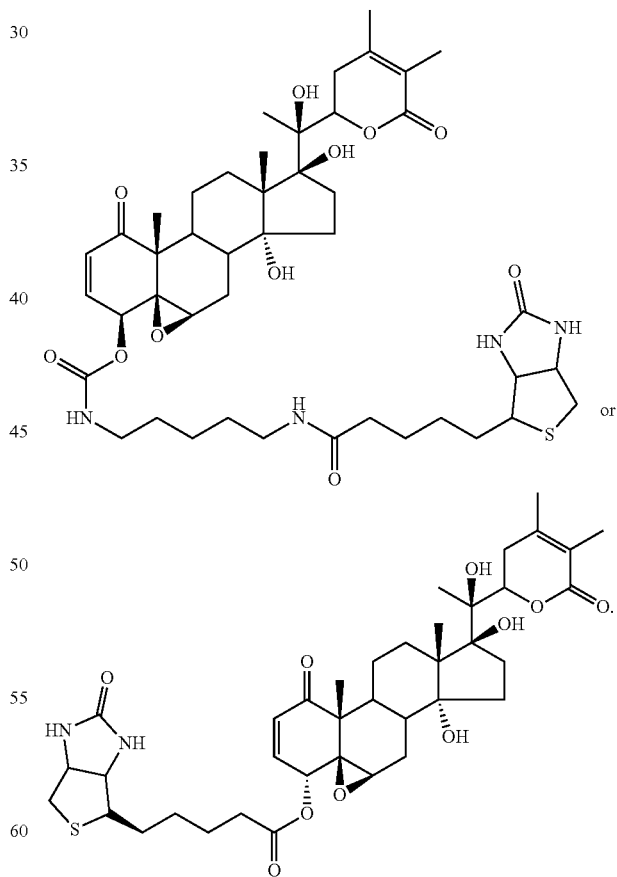

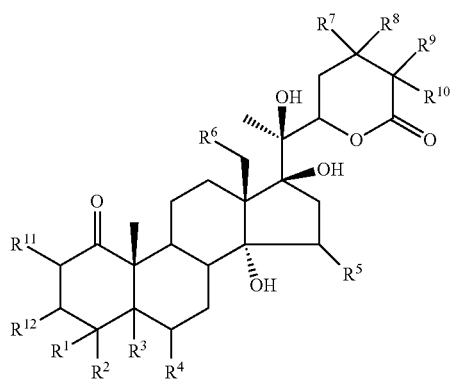

16. A method of synergistically enhancing the response of cancer cells in a mammal to treatment with an apoptosis inducing ligand or of inducing apoptosis in cancer cells in a mammal that are resistant to treatment with an apoptosis inducing ligand comprising administering to the mammal a therapeutically effective amount of a compound of the formula:

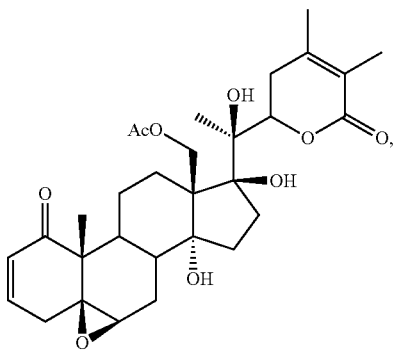 [SMILES: CC(=O)OC[C@]12CCC3C(C[C@H]4O[C@]45CC=CC(=O)[C@]35C)[C@]1(O)CC[C@@]2(O)[C@@](C)(O)C1CC(C)=C(C)C(=O)O1]

and administering an effective amount of an apoptosis-inducing ligand, whereby a synergistic enhancement of the response is obtained or whereby apoptosis is induced in the cancer cells, and wherein the apoptosis-inducing ligand is TNF-α, FasL, or poly IC.

17. The method of claim 16, wherein the cancer cells are associated with a cancer selected from glioma, thyroid carcinoma, breast carcinoma, small-cell lung carcinoma, non-small-cell lung carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, skin carcinoma, melanoma, basal cell carcinoma, squamous cell carcinoma, anaplastic large-cell lymphoma, multiple myeloma, leukemia, lymphoma, cervical carcinoma, and mesothelioma, follicular thyroid carcinoma, colorectal cancer, myeloid leukemia, hepatic cancer, hepatocellular carcinoma, cholangiocarcinoma, cervical and ovarian cancer, cancers of glial origin, and combinations thereof.

18. The method according to claim 16, further comprising administering to the mammal an Smac mimetic which is birinapant, GDC-015, or LCL-161, a Bcl-2 antagonist which is ABT-199, ABT-737, or venetoclax, or a combination thereof.

\* \* \* \* \*